US011136578B2

(12) United States Patent
Rana

(10) Patent No.: US 11,136,578 B2
(45) Date of Patent: *Oct. 5, 2021

(54) IN VIVO GENE SILENCING BY CHEMICALLY MODIFIED AND STABLE SIRNA

(71) Applicant: UNIVERSITY OF MASSACHUSETTS, Boston, MA (US)

(72) Inventor: Tariq M. Rana, San Diego, CA (US)

(73) Assignee: UNIVERSITY OF MASSACHUSETTS, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/106,997

(22) Filed: Aug. 21, 2018

(65) Prior Publication Data

US 2019/0085328 A1     Mar. 21, 2019

Related U.S. Application Data

(63) Continuation of application No. 14/661,810, filed on Mar. 18, 2015, now Pat. No. 10,087,441, which is a continuation of application No. 13/561,357, filed on Jul. 30, 2012, now Pat. No. 9,012,623, which is a continuation of application No. 10/672,069, filed on Sep. 25, 2003, now abandoned.

(60) Provisional application No. 60/493,095, filed on Aug. 5, 2003, provisional application No. 60/458,051, filed on Mar. 26, 2003, provisional application No. 60/426,982, filed on Nov. 15, 2002, provisional application No. 60/413,529, filed on Sep. 25, 2002.

(51) Int. Cl.
| | |
|---|---|
| *C07H 21/04* | (2006.01) |
| *C12N 15/113* | (2010.01) |
| *C07D 213/69* | (2006.01) |
| *C07D 495/04* | (2006.01) |
| *C12N 15/11* | (2006.01) |
| *A61K 38/00* | (2006.01) |
| *A61K 48/00* | (2006.01) |

(52) U.S. Cl.
CPC .......... *C12N 15/113* (2013.01); *C07D 213/69* (2013.01); *C07D 495/04* (2013.01); *C12N 15/111* (2013.01); *C12N 15/1137* (2013.01); *C12Y 207/11022* (2013.01); *A01K 2217/075* (2013.01); *A61K 38/00* (2013.01); *A61K 48/00* (2013.01); *C12N 2310/14* (2013.01); *C12N 2310/31* (2013.01); *C12N 2310/315* (2013.01); *C12N 2310/322* (2013.01); *C12N 2310/33* (2013.01); *C12N 2310/335* (2013.01); *C12N 2310/3341* (2013.01); *C12N 2310/3513* (2013.01); *C12N 2310/53* (2013.01); *C12N 2320/51* (2013.01)

(58) Field of Classification Search
None
See application file for complete search history.

(56) References Cited

U.S. PATENT DOCUMENTS

| | | | |
|---|---|---|---|
| 5,672,695 A | 9/1997 | Eckstein et al. | |
| 6,355,787 B1 * | 3/2002 | Beckvermit | ........... C07H 19/06 536/23.1 |
| 6,358,932 B1 | 3/2002 | Monia | |
| 6,506,559 B1 | 1/2003 | Fire et al. | |
| 2003/0084471 A1 * | 5/2003 | Beach | ............... C12N 15/1034 800/278 |
| 2003/0143732 A1 | 7/2003 | Fosnaugh et al. | |
| 2004/0029275 A1 | 2/2004 | Brown et al. | |
| 2004/0192626 A1 | 9/2004 | McSwiggen et al. | |
| 2004/0248299 A1 | 12/2004 | Jayasena et al. | |
| 2005/0026160 A1 | 2/2005 | Allerson et al. | |
| 2005/0186586 A1 | 8/2005 | Zamore et al. | |

FOREIGN PATENT DOCUMENTS

| | | |
|---|---|---|
| CA | 2459532 A1 | 8/2003 |
| WO | 1994/001550 A1 | 1/1994 |
| WO | 2002/016620 A2 | 2/2002 |
| WO | 2002/044321 A2 | 6/2002 |

(Continued)

OTHER PUBLICATIONS

US 5,782,242 A, 02/1999, Monia (withdrawn)
Amaral et al. (What Role Does CFTR Play in Development, Differentiation, Regeneration and Cancer?. International journal of molecular sciences 21.9 (2020): 3133).*
Burgess, Kevin, et al., "Photolytic Mass Laddering for Fast Characterization of Oligomers on Single Resin Beads," J. Org. Chem., vol. 62:5662-5663 (1997).
Caplen, Natasha J., et al., "Specific inhibition of gene expression by small double-stranded RNAs in invertebrate and vertebrate systems," PNAS, vol. 98(17):9742-9747 (2001).

(Continued)

*Primary Examiner* — Kimberly Chong
(74) *Attorney, Agent, or Firm* — Lathrop GPM LLP; James H. Velema, Esq.

(57) ABSTRACT

The present invention provides compositions for RNA interference and methods of use thereof. In particular, the invention provides small interfering RNAs (siRNAs) having modification that enhance the stability of the siRNA without a concomitant loss in the ability of the siRNA to participate in RNA interference (RNAi). The invention also provides siRNAs having modification that increase targeting efficiency. Modifications include chemical crosslinking between the two complementary strands of an siRNA and chemical modification of a 3' terminus of a strand of an siRNA. Preferred modifications are internal modifications, for example, sugar modification, nucleobase modification and/or backbone modifications. Such modifications are also useful, e.g., to improve uptake of the siRNA by a cell. Functional and genomic and proteomic methods are featured. Therapeutic methods are also featured.

12 Claims, 42 Drawing Sheets

Specification includes a Sequence Listing.

(56) References Cited

FOREIGN PATENT DOCUMENTS

| WO | 2003/070750 A2 | 8/2003 |
| WO | 2004/014933 A1 | 2/2004 |

OTHER PUBLICATIONS

Chiu, Y.L., et al., "RNAi in human cells: basic structural and functional features of small interfering RNA," Mol. Cell, vol. 10:549-561 (2002).
Chiu, Ya-Lin et al., "siRNA function in RNAi: A chemical modification analysis," RNA, vol. 9(9):1034-1048 (2003).
Cimino, G.D., et al., "Psoralens as photoactive probes of nucleic acid structure and function: organic chemistry, photochemistry, and biochemistry," Annu. Rev. Biochem., vol. 54:1151-1193 (1985).
Cummins, Lendell L., et al,. "Characterization of fully 2'-modified oligoribonucleotide hetero- and homoduplex hybridization and nuclease sensitivity," Nucleic Acids Research, vol. 23(11):2019-2024 (1995).
Elbashir, S.M., et al., "Duplexes of 21-nucleotide RNAs mediate RNA interferences in cultured mammalian cells," Nature, vol. 411:494-498 (2001).
Elbashir, S.M., et al., "Functional anatomy of siRNAs for mediateing efficient RNAi in *Drosophila melanogaster* embryo lysate," Embo. J., vol. 20:6877-6888 (2001).
Elbashir, Sayda M., et al., "RNA interference is mediated by 21- and 22-nucleotide RNAs," Genes & Development, vol. 15:188-200 (2001).
Harborth, Jens et al., "Sequence, Chemical, and Structural Variation of Small Interfering RNAs and Short Hairpin RNAs and the Effect on Mammalian Gene Silencing," Antisense and Nucleic Acid Development, vol. 13: 83-105 (2003).
Hearst, J.E., et al., "The reaction of the psoralens with deoxyribonucleic acid," Q. Rev. Biophys., vol. 17:1-44 (1984).
Holen, Torgeir et al., "Positional effects of short interfering RNAs targeting the human coagulation trigger Tissue Factor," Nucleic Acids Research, vol. 30(8):1757-1766 (2002).
Holmes, Christopher P., et al., "Strategies for Combinatorial Organic Synthesis: Solution and Polymer-Supported Synthesis of 4-Thiazolidinones and 4-Metathiazanones Derived from Amino Acids," J. Org. Chem., vol. 60:7328-7333 (1995).
Kanne, D., et al., "Psoralen-deoxyribonucleic acid photoreaction. Characterization of the monoaddition products from 8-methoxypsoralen and 4,5'8-trimethylpsoralen," Biochemistry, vol. 21:861-871 (1982).
Kaplan et al., "Spt5 and Spt6 are associated with active transcription and have characteristics of general elongation factors in D. melanogaster," Genes Dev, 14:2623-2634 (2000).
Lipardi, C., et al., "RNAi as random degradative PCR: siRNA primers convert mRNA into dsRNAs that are degraded to generate new siRNAs," Cell, vol. 107:297-307 (2001).
Lipson, S.E., et al., "Structure of M1 RNA as determined by psoralen cross-linking," Biochemistry, vol. 27:570-575 (1988).
Luy, B., et al., "Measurement and application of 1H-19F dipolar couplings in teh structure determination of 2'-fluorolabeled RNA," J. Biomol. NMR, vol. 20:39-47 (2001).
Luyten, I., et al., "Hybridization properties of base-modified oligonucleotides within the double and triple helix motif," Eur. J. Med. Chem., vol. 33:515-576 (1998).
Majlessi, M., et al., "Advantages of 2'-0-methyl oligoribonucleotide probes for detecting RNA targets," Nucleic Acids Res., vol. 26:2224-2229 (1998).
Neenhold, H.R., et al., "Major groove opening at the HIV-1 Tat binding site of TAR RNA evidenced by a rhodium probe," Biochemistry, vol. 34:6303-6309 (1995).
Nykanen, A., et al., "ATP requirements and small interfering RNA structure in the RNA interference pathway," Cell, vol. 107:309-321 (2001).
Parrish, S., et al., "Functional anatomy of a dsRNA trigger: differential requirement for the two trigger strands in RNA interference," Mol Cell., vol. 6:1077-1087 (2000).
Pierce Chemical Company, Instructions, "NHS-Esters-Maleimide Crosslinkere," pp. 1-8 (2001).
Saenger, W., ed, "Principles of Nucleic Acid Structure," New York, Springer-Verlag (1984).
Schwarz, Dianne S. et al., "Evidence that siRNAs Function as Guides, Not Primers, in the *Drosophila* and Human RNAi Pathways," Molecular Cell, vol. 10:537-548 (2002).
Sijen, T., et al., "On the role of RNA amplification in dsRNA-triggered gene silencing," Cell, vol. 107:465-476 (2001).
Stein, C.A., "Phosphorothioate antisense oligodeoxynucleotides: questions of specificity," Trends Biotechnol, vol. 14:147-149 (1996).
Thompson, J.F., et al., "Structure of *E. coli* 16S RNA elucidated by psoralen crosslinking," Cell, vol. 32:1355-1365 (1983).
Turner, S., et al., "Identification of sites of 4'-(hydroxymethyl)-4,5',8-trimethoxylpsoralen cross-linking in the *Escherichia coli* 23S ribosomal ribonucleic acid," Biochemistry, vol. 22:4159-4164 (1983).
Tuschl, Thomas, et al., "Small Interfering RNAs: A Revolutionary Tools for the Analysis of Gene Function and Gene Therapy," Molecular Interventions, vol. 2(3):158-167 (2002).
Weeks, K.M., et al., "Major Groove Accessibility of RNA.," Science, vol. 261:1574-1577 (1993).
Wianny, Florence, et al., "Specific interference with gene function by double-stranded RNA in early mouse development," Nature Cell Biology, vol. 2:70-75 (2000).
Wu-Baer et al.m "Role of the human homolog of the yeast transcription factor SPT5 in HIV-1 tat-activation," J. Mol. Biol., 277:179-197 (1998).
Canadian Office Action for Application No. 2,500,224, 3 pages, dated Jan. 11, 2012.
European Search Report for Application No. 03774498.4-2403, dated Sep. 12, 2007.
International Preliminary Examination Report Application No. PCT/US03/30480, dated Jun. 15, 2005.
International Search Report Application No. PCT/US03/30480, dated Jan. 5, 2005.
Supplementary Partial European Search Report for Application No. 03774498.4-2403, dated Jun. 21, 2007.
Doench et al. (2003) "siRNAs can function as miRNAs," Genes and Development 17:438-442.
U.S. Appl. No. 10/672,069, filed Sep. 25, 2003, Tariq M. Rana.
U.S. Appl. No. 13/561,357 U.S. Pat. No. 9,012,623, filed Jul. 30, 2013 Apr. 21, 2015, Tariq M. Rana.
U.S. Appl. No. 14/661,810 U.S. Pat. No. 10,087,441, filed Mar. 18, 2015 Oct. 2, 2018, Tariq M. Rana.

\* cited by examiner

FIG. 1A

| | | | |
|---|---|---|---|
| GFP ds siRNA | Sense strand (ss)<br>Antisense strand (as) | 5´ GCAGCACGACUUCUUCAAGdTdT<br>dTdTCGUCGUCGUGCUGAAGAAGUUC 5´ | (SEQ ID No. 1)<br>(SEQ ID No. 2) |
| GFP mRNA target site sequence | | AAGCAGCACGACUUCUUCAAG<br>238                          258 | (SEQ ID No. 3) |
| GFP mRNA | m7GpppG ———————————— Poly A | | |
| RFP mRNA | m7GpppG ———————————— Poly A | | |
| RFP mRNA target site sequence | | AAGUGGGAGCGCGUGAUGAAC<br>277                          297 | (SEQ ID No. 4) |
| RFP ds siRNA | Sense strand (ss)<br>Antisense strand (as) | 5´ GUGGGAGCGCGUGAUGAACdTdT<br>dTdTCACCCUCGCGCACUACUUG 5´ | (SEQ ID No. 5)<br>(SEQ ID No. 6) |

FIG. 1B

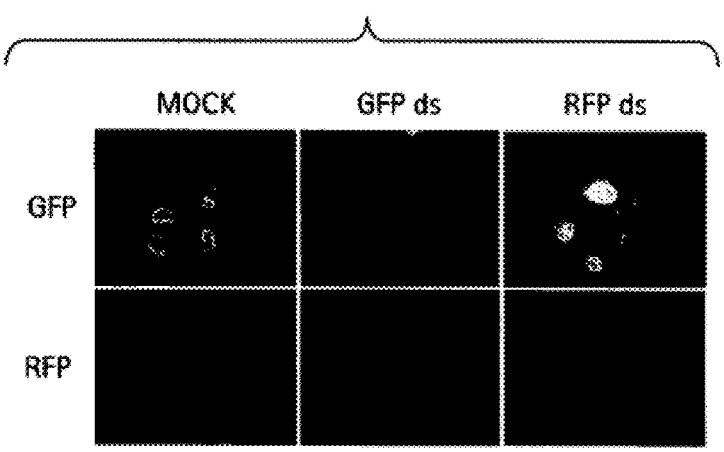

FIG. 2B

| | GFP siRNA | | |
|---|---|---|---|
| | ds (WT) | GCAGCACGACUUCUUCAAGdTdT | (SEQ ID No. 1) |
| | | dTdTCGUCGUGCUGAAGAAGUUC | (SEQ ID No. 2) |
| 5' Modified siRNA | 5'-N3ss/as | N3-GCAGCACGACUUCUUCAAGdTdT | (SEQ ID No. 7) |
| | | dTdTCGUCGUGCUGAAGAAGUUC | (SEQ ID No. 2) |
| | ss/5'-N3as | GCAGCACGACUUCUUCAAGdTdT | (SEQ ID No. 1) |
| | | dTdTCGUCGUGCUGAAGAAGUUC-N3 | (SEQ ID No. 8) |
| | 5'-N3ss/5'-N3as | N3-GCAGCACGACUUCUUCAAGdTdT | (SEQ ID No. 7) |
| | | dTdTCGUCGUGCUGAAGAAGUUC-N3 | (SEQ ID No. 8) |
| 3' Modified siRNA | ss3'-Pmn/as | GCAGCACGACUUCUUCAAGdTdT-Pmn | (SEQ ID No. 9) |
| | | dTdTCGUCGUGCUGAAGAAGUUC | (SEQ ID No. 2) |
| | ss/as3'-Pmn | GCAGCACGACUUCUUCAAGdTdT | (SEQ ID No. 1) |
| | | Pmn-dTdTCGUCGUGCUGAAGAAGUUC | (SEQ ID No. 10) |
| | ss3'-Pmn/as3'-Pmn | GCAGCACGACUUCUUCAAGdTdT-Pmn | (SEQ ID No. 9) |
| | | Pmn-dTdTCGUCGUGCUGAAGAAGUUC | (SEQ ID No. 10) |
| | ss/as3'-Biotin | GCAGCACGACUUCUUCAAGdTdT | (SEQ ID No. 1) |
| | | Biotin-dTdTCGUCGUGCUGAAGAAGUUC | (SEQ ID No. 11) |
| Bulge-containing siRNA | ss-bulge/as | GCAGCACGA UG CUUCUUCAAGdTdT | (SEQ ID No. 12) |
| | | dTdTCGUCGUGCU GAAGAAGUUC | (SEQ ID No. 2) |
| | ss/as-bulge | GCAGCACGA CUUCUUCAAGdTdT | (SEQ ID No. 1) |
| | | dTdTCGUCGUGCU GAAGAAGUUC CA | (SEQ ID No. 13) |
| | ss-bulge/as-bulge | GCAGCACGA UG CUUCUUCAAGdTdT | (SEQ ID No. 12) |
| | | dTdTCGUCGUGCU GAAGAAGUUC CA | (SEQ ID No. 13) |

5'-N3ss/5'-N3as ss/as3'-Biotin ss3'-Pmn/as ss/as3'-Pmn

Psoralen (HMT)

GFP ds siRNA

GCAGCACGACUUCUUCAAGdTdT    (SEQ ID No. 1)
dTdTCGUCGUGCUGAAGAAGUUC    (SEQ ID No. 2)

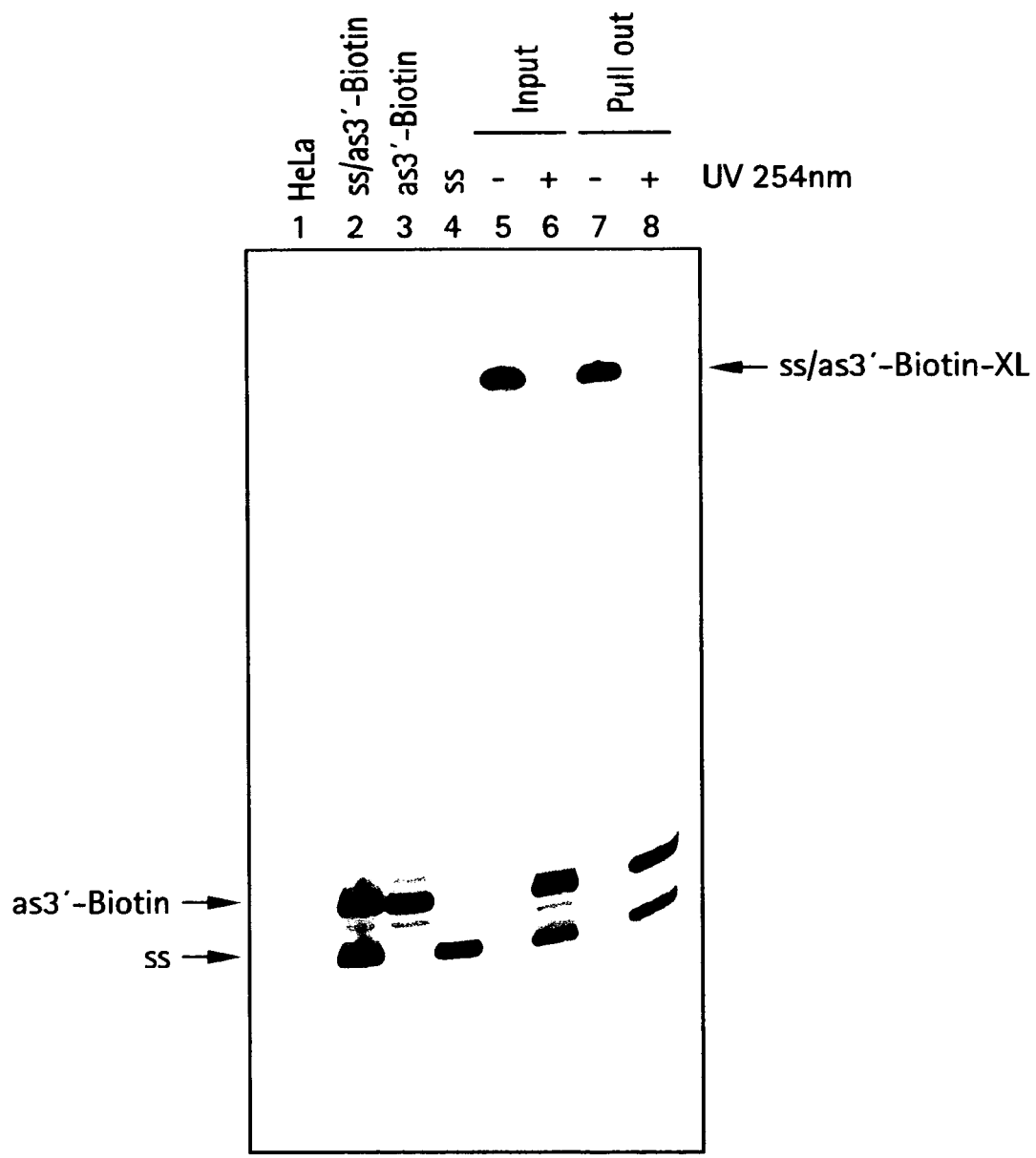

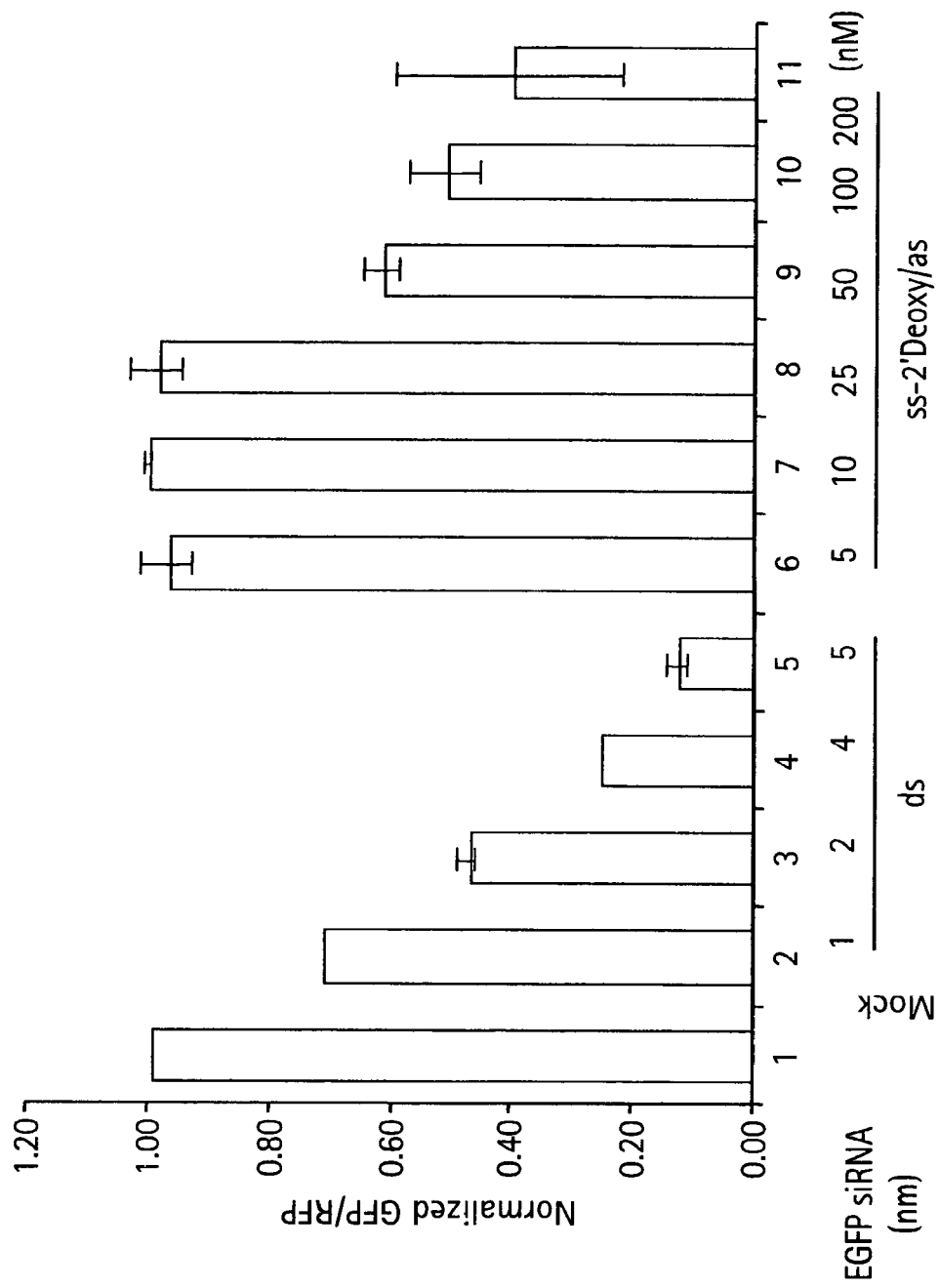

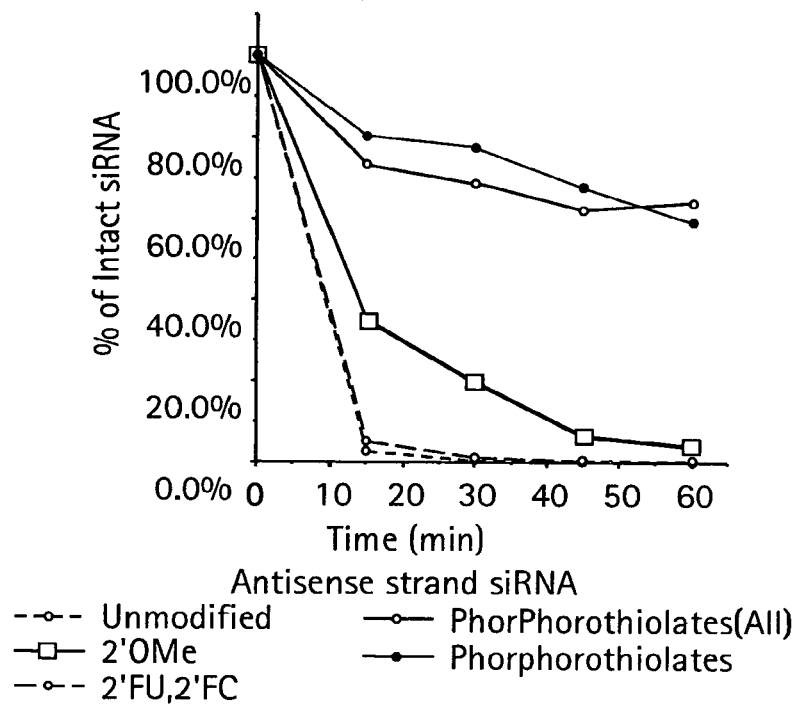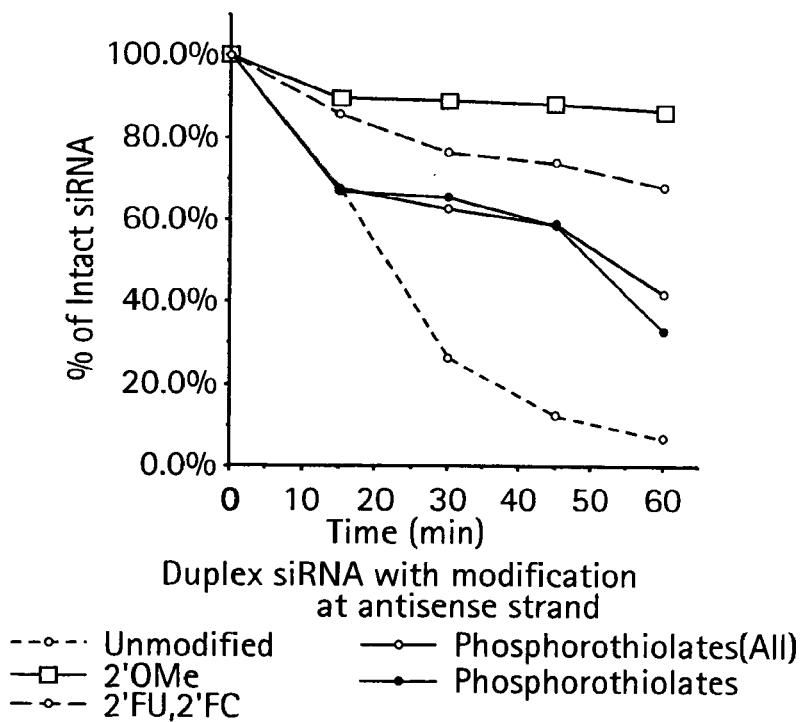

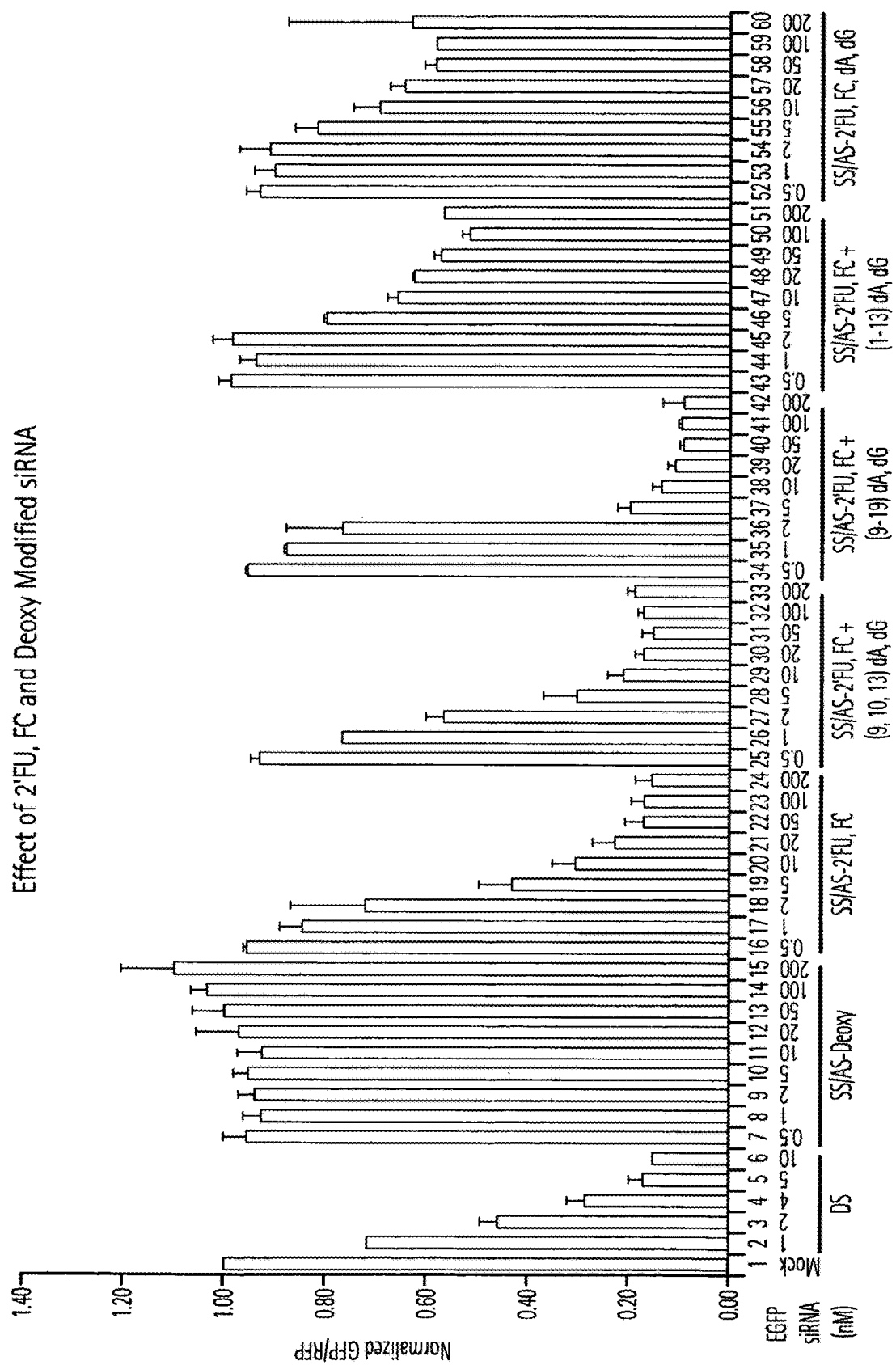

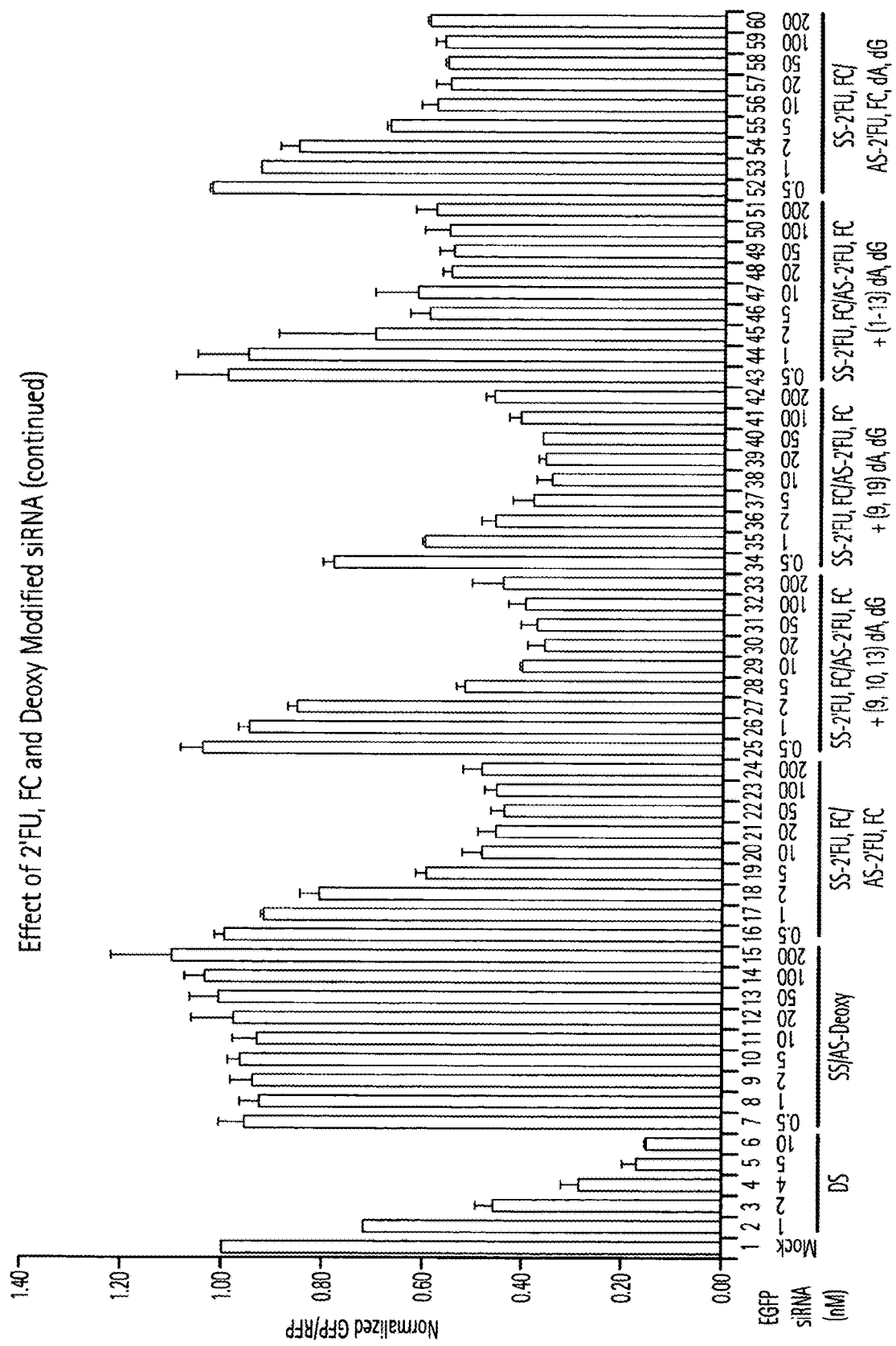
FIG. 13D Effect of 2'FU, FC and Deoxy Modified siRNA (continued)

FIG. 15A

GCAGCACGACUUCUUCAAGdTdT (SEQ ID No. 1)
dTdTCGUCGUGCUGAAGAAGUUC (SEQ ID No. 2)

GCAGCACGACUUCUUCAAGdTdT (SEQ ID No. 1)
dTdTCGUCGUGCUGAAGAAGUUC (SEQ ID No. 2)

GCAGCACGACUUCUUCAAGdTdT (SEQ ID No. 1)
dTdTCGUCGGUGCUGAAGAAGUUC (SEQ ID No. 23)

SS/AS-(18, 19)mm

GCAGCACGACUUCUUCAAGdTdT (SEQ ID No. 1)
dTdTCGUCGUGCUGAAGAAGUCU (SEQ ID No. 24)

SS/AS-(1, 2)mm

Photocleavable Biotin

SEQUENCE LISTING

```
<160> NUMBER OF SEQ ID NOS: 34

<210> SEQ ID NO 1
<211> LENGTH: 21
<212> TYPE: DNA
```

```
<213> ORGANISM: Artificial Sequence
<220> FEATURE:
<223> OTHER INFORMATION: Synthetic sequence: RNA molecule with
      deoxythymidines at positions 20 and 21

<400> SEQUENCE: 1
gcagcacgac uucuucaagt t                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidines at positions 20 and 21

<400> SEQUENCE: 2
cuugaagaag ucgugcugct t                                              21

<210> SEQ ID NO 3
<211> LENGTH: 21
<212> TYPE: RNA
<213> ORGANISM: Artificial Sequence
<220> FEATURE:
<223> OTHER INFORMATION: siRNA target sequence

<400> SEQUENCE: 3
aagcagcacg acuucuucaa g                                              21

<210> SEQ ID NO 4
<211> LENGTH: 21
<212> TYPE: RNA
<213> ORGANISM: Artificial Sequence
<220> FEATURE:
<223> OTHER INFORMATION: siRNA target sequence

<400> SEQUENCE: 4
aagugggagc gcgugaugaa c                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidines at positions 20 and 21

<400> SEQUENCE: 5
gugggagcgc gugaugaact t                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidines at positions 20 and 21

<400> SEQUENCE: 6
guucaucacg cgcucccact t                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic sequence: RNA molecule with
```

-continued

```
      deoxythymidines at positions 20 and 21
<220> FEATURE:
<221> NAME/KEY: modified_base
<222> LOCATION: (1)..(1)
<223> OTHER INFORMATION: 5'-aminopropyl-modified guanosine

<400> SEQUENCE: 7
gcagcacgac uucuucaagt t                                               21

<210> SEQ ID NO 8
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidines at positions 20 and 21
<220> FEATURE:
<221> NAME/KEY: modified_base
<222> LOCATION: (1)..(1)
<223> OTHER INFORMATION: 5'-aminopropyl-modified cytidine

<400> SEQUENCE: 8
cuugaagaag ucgugcugct t                                               21

<210> SEQ ID NO 9
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidine at positions 20
<220> FEATURE:
<221> NAME/KEY: modified_base
<222> LOCATION: (21)..(21)
<223> OTHER INFORMATION: 3'-Puromycin modified deoxythymidine

<400> SEQUENCE: 9
gcagcacgac uucuucaagt t                                               21

<210> SEQ ID NO 10
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidine at positions 20
<220> FEATURE:
<221> NAME/KEY: modified_base
<222> LOCATION: (21)..(21)
<223> OTHER INFORMATION: 3'-Puromycin-modified deoxythymidine

<400> SEQUENCE: 10
cuugaagaag ucgugcugct t                                               21

<210> SEQ ID NO 11
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidine at position 20 and 3'-Biotin-modified
      deoxythymidine at position 21
<220> FEATURE:
<221> NAME/KEY: modified_base
<222> LOCATION: (21)..(21)
<223> OTHER INFORMATION: 3'-Biotin-modified deoxythymidine

<400> SEQUENCE: 11
cuugaagaag ucgugcugct t                                               21
```

<210> SEQ ID NO 12
<211> LENGTH: 23
<212> TYPE: DNA
<213> ORGANISM: Artificial Sequence
<220> FEATURE:
<223> OTHER INFORMATION: Synthetic sequence: RNA molecule with
      deoxythymidines at positions 22 and 23

<400> SEQUENCE: 12
gcagcacgac uguucuucaa gtt                                           23

<210> SEQ ID NO 13
<211> LENGTH: 23
<212> TYPE: DNA
<213> ORGANISM: Artificial Sequence
<220> FEATURE:
<223> OTHER INFORMATION: Synthetic sequence: RNA molecule with
      deoxythymidines at positions 22 and 23

<400> SEQUENCE: 13
cuugaagaaa cgucgugcug ctt                                           23

<210> SEQ ID NO 14
<211> LENGTH: 21
<212> TYPE: DNA
<213> ORGANISM: Artificial Sequence
<220> FEATURE:
<223> OTHER INFORMATION: Synthetic sequence: RNA molecule with
      deoxynucleosides at positions 1-21

<400> SEQUENCE: 14
cuugaagaag ucgugcugct t                                             21

<210> SEQ ID NO 15
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidines at positions 20 and 21
<220> FEATURE:
<221> NAME/KEY: modified_base
<222> LOCATION: (1)..(12)
<223> OTHER INFORMATION: 2'-fluoro cytidine
<220> FEATURE:
<221> NAME/KEY: modified_base
<222> LOCATION: (2)..(3)
<223> OTHER INFORMATION: 2'-fluoro uridine

<400> SEQUENCE: 15
cuugaagaag ucgugcugct t                                             21

<210> SEQ ID NO 16
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidines at positions 20 and 21, deoxyadenosine at position
      9 and deoxyguanosine at positions 10 and 13
<220> FEATURE:
<221> NAME/KEY: modified_base
<222> LOCATION: (1)..(12)
<223> OTHER INFORMATION: 2'-fluoro cytidine
<220> FEATURE:
<221> NAME/KEY: modified_base
<222> LOCATION: (2)..(3)
<223> OTHER INFORMATION: 2'-fluoro uridine

<400> SEQUENCE: 16
cuugaagaag ucgugcugct t                                              21

<210> SEQ ID NO 17
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidines at positions 20 and 21, deoxyadenosine at position
      9 and deoxyguanosine at positions 10, 13, 15 and 18
<220> FEATURE:
<221> NAME/KEY: modified_base
<222> LOCATION: (1)..(12)
<223> OTHER INFORMATION: 2'-fluoro cytidine
<220> FEATURE:
<221> NAME/KEY: modified_base
<222> LOCATION: (2)..(3)
<223> OTHER INFORMATION: fluoro uridine

<400> SEQUENCE: 17
cuugaagaag ucgugcugct t                                              21

<210> SEQ ID NO 18
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidines at positions 20 and 21, deoxyadenosine at position
      5, 6, 8, 9 and deoxyguanosine at positions 4, 7, 10 and 13
<220> FEATURE:
<221> NAME/KEY: modified_base
<222> LOCATION: (1)..(12)
<223> OTHER INFORMATION: 2'-fluoro cytidine
<220> FEATURE:
<221> NAME/KEY: modified_base
<222> LOCATION: (2)..(3)
<223> OTHER INFORMATION: 2'-fluoro uridine

<400> SEQUENCE: 18
cuugaagaag ucgugcugct t                                              21

<210> SEQ ID NO 19
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidines at positions 20 and 21, deoxyadenosine at position
      5, 6, 8, 9 and deoxyguanosine at positions 4, 7, 10, 13, 15 and 18
<220> FEATURE:
<221> NAME/KEY: modified_base
<222> LOCATION: (1)..(12)
<223> OTHER INFORMATION: 2'-fluoro cytidine
<220> FEATURE:
<221> NAME/KEY: modified_base
<222> LOCATION: (2)..(3)
<223> OTHER INFORMATION: 2'-fluoro uridine

<400> SEQUENCE: 19
cuugaagaag ucgugcugct t                                              21

<210> SEQ ID NO 20
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidines at positions 20 and 21
<220> FEATURE:
<221> NAME/KEY: modified_base

```
<222> LOCATION: (2)..(5)
<223> OTHER INFORMATION: 2'-fluoro cytidine
<220> FEATURE:
<221> NAME/KEY: modified_base
<222> LOCATION: (11)..(12)
<223> OTHER INFORMATION: 2'-fluoro uridine

<400> SEQUENCE: 20
gcagcacgac uucuucaagt t                                              21

<210> SEQ ID NO 21
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidines at positions 20 and 21
<220> FEATURE:
<221> NAME/KEY: modified_base
<222> LOCATION: (11)..(11)
<223> OTHER INFORMATION: 3-methyl uridine

<400> SEQUENCE: 21
cuugaagaag ucgugcugct t                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidines at positions 20 and 21
<220> FEATURE:
<221> NAME/KEY: modified_base
<222> LOCATION: (2)..(3)
<223> OTHER INFORMATION: 3-methyl uridine

<400> SEQUENCE: 22
cuugaagaag ucgugcugct t                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidines at positions 20 and 21

<400> SEQUENCE: 23
cuugaagaag ucgugcucgt t                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidines at positions 20 and 21

<400> SEQUENCE: 24
ucugaagaag ucgugcugct t                                              21

<210> SEQ ID NO 25
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidines at positions 20 and 21
```

```
<400> SEQUENCE: 25
ucccuuccug auacuagaat t                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidines at positions 20 and 21

<400> SEQUENCE: 26
ucccuuccgu auacuagaat t                                              21

<210> SEQ ID NO 27
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidines at positions 20 and 21

<400> SEQUENCE: 27
ccaaagcuuc ccccuauaat t                                              21

<210> SEQ ID NO 28
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidines at positions 20 and 21

<400> SEQUENCE: 28
ccaaagcucu ccccuauaat t                                              21

<210> SEQ ID NO 29
<211> LENGTH: 23
<212> TYPE: DNA
<213> ORGANISM: Artificial Sequence
<220> FEATURE:
<223> OTHER INFORMATION: siRNA target sequence

<400> SEQUENCE: 29
aactgggcga gtattacatg att                                            23

<210> SEQ ID NO 30
<211> LENGTH: 23
<212> TYPE: DNA
<213> ORGANISM: Artificial Sequence
<220> FEATURE:
<223> OTHER INFORMATION: siRNA target sequence

<400> SEQUENCE: 30
aactgggcgg atattacatg att                                            23

<210> SEQ ID NO 31
<211> LENGTH: 21
<212> TYPE: DNA
<213> ORGANISM: Artificial Sequence
<220> FEATURE:
<223> OTHER INFORMATION: Synthetic sequence: RNA molecule with two
      deoxythymidines at positions 20 and 21

<400> SEQUENCE: 31
```

```
uuggucuccu ugaugcuuut t                                              21

<210> SEQ ID NO 32
<211> LENGTH: 21
<212> TYPE: DNA
<213> ORGANISM: Artificial Sequence
<220> FEATURE:
<223> OTHER INFORMATION: Synthetic sequence: RNA molecule with
      deoxythymidines at positions 20 and 21

<400> SEQUENCE: 32
gaaacguaga cagcgcagat t                                              21

<210> SEQ ID NO 33
<211> LENGTH: 40
<212> TYPE: DNA
<213> ORGANISM: Artificial Sequence
<220> FEATURE:
<223> OTHER INFORMATION: DNA primer

<400> SEQUENCE: 33
gcctaatacg actcactata ggacctacgg cgtgcagtgc                          40

<210> SEQ ID NO 34
<211> LENGTH: 40
<212> TYPE: DNA
<213> ORGANISM: Artificial Sequence
<220> FEATURE:
<223> OTHER INFORMATION: DNA primer

<400> SEQUENCE: 34
ttgatttagg tgacactata gatggtgcgc tcctggacgt                          40
```

IN VIVO GENE SILENCING BY CHEMICALLY MODIFIED AND STABLE SIRNA

RELATED APPLICATIONS

This application is a continuation of U.S. patent application Ser. No. 14/661,810, filed Mar. 18, 2015, which is a continuation of U.S. patent application Ser. No. 13/561,357, filed Jul. 30, 2012, now U.S. Pat. No. 9,012,623, which is a continuation of U.S. patent application Ser. No. 10/672,069, filed Sep. 25, 2003, which claims the benefit of: U.S. Provisional Patent Application Ser. No. 60/413,529, filed Sep. 25, 2002; U.S. Provisional Patent Application Ser. No. 60/426,982, filed Nov. 15, 2002; U.S. Provisional Patent Application Ser. No. 60/458,051, filed Mar. 26, 2003; and U.S. Provisional Patent Application Ser. No. 60/493,095, filed Aug. 5, 2003. The entire contents of the above-referenced patent applications are incorporated herein by this reference.

BACKGROUND OF THE INVENTION

RNA interference (RNAi) is the process whereby double-stranded RNA (dsRNA) induces the sequence-specific degradation of homologous mRNA. Although RNAi was first discovered in *Caenorhabditis elegans* (Fire et al., 1998), similar phenomena had been reported in plants (post-transcriptional gene silencing [PTGS]) and in *Neurospora crassa* (quelling) (reviewed in Hammond et al., 2001; Sharp, 2001). It has become clear that dsRNA-induced silencing phenomena are present in evolutionarily diverse organisms, e.g., nematodes, plants, fungi and trypanosomes (Bass, 2000; Cogoni and Macino, 2000; Fire et al., 1998; Hammond et al., 2001; Ketting and Plasterk, 2000; Matzke et al., 2001; Sharp, 2001; Sijen and Kooter, 2000; Tuschl, 2001; Waterhouse et al., 2001). Biochemical studies in *Drosophila* embryo lysates and S2 cell extracts have begun to unravel the mechanisms by which RNAi works (Bernstein et al., 2001; Tuschl et al., 1999; Zamore et al., 2000).

RNAi is initiated by an ATP-dependent, processive cleavage of dsRNA into 21- to 23-nucleotide (nt) short interfering RNAs (siRNAs) (Bernstein et al., 2001; Hamilton and Baulcombe, 1999; Hammond et al., 2000; Zamore et al., 2000) by the enzyme Dicer, a member of the RNase III family of dsRNA-specific endonucleases (Bernstein et al., 2001). These native siRNA duplexes containing 5' phosphate and 3' hydroxyl termini are then incorporated into a protein complex called RNA-induced silencing complex (RISC) (Hammond et al., 2000). ATP-dependent unwinding of the siRNA duplex generates an active complex, RISC* (the asterisk indicates the active conformation of the complex) (Nykanen et al., 2001). Guided by the antisense strand of siRNA, RISC* recognizes and cleaves the corresponding mRNA (Elbashir et al., 2001b; Hammond et al., 2000; Nykanen et al., 2001).

Recently, Tuschl and colleagues (Elbashir et al., 2001a) have demonstrated that RNAi can be induced in numerous mammalian cell lines by introducing synthetic 21-nt siRNAs. By virtue of their small size, these siRNAs avoid provoking an interferon response that activates the protein kinase PKR (Stark et al., 1998). Functional anatomy studies of synthetic siRNA in *Drosophila* cell lysates have demonstrated that each siRNA duplex cleaves its target RNA at a single site (Elbashir et al., 2001c). The 5' end of the guide siRNA sets the ruler for defining the position of target RNA cleavage (Elbashir et al., 2001c). 5' phosphorylation of the antisense strand is required for effective RNA interference in vitro (Nykanen et al., 2001). Mutation studies have shown that a single mutation within the center of an siRNA duplex discriminates between mismatched targets (Elbashir et al., 2001c). These experiments showed a more stringent requirement for the antisense strand of the trigger dsRNA as compared to the sense strand (Grishok et al., 2000; Parrish et al., 2000). Notably these phenomena were demonstrated in vitro or in cell culture systems.

There is a need for further study of such systems. Moreover, there exists a need for the development of reagents suitable for use in vivo, in particular for use in developing human therapeutics.

SUMMARY OF THE INVENTION

The present invention is based on the suprising discovery that siRNA molecules (i.e., duplex siRNA molecules) can be modified at internal residues such that properties important for in vivo applications, in particular, human therapeutic applications, are improved without compromising the RNAi activity of the siRNA molecules. In particular, the invention is based on the discovery of modifications which are tolerated in siRNA molecules, modifications which are not tolerated, and three-dimensional structural features that are or are not required in order for siRNA molecules to mediate RNAi. Accordingly, the present invention provides compositions for RNA interference and methods of use thereof. In particular, the invention provides small interfering RNAs (siRNAs) having modification or combination of modifications that enhance the stability of the siRNA without a comcommittent loss in the ability of the siRNA to participate in RNA interference (RNAi). The invention also provides siRNAs having modification that increase targeting efficiency.

Modifications include chemical crosslinking between the two complementary strands of an siRNA and chemical modification of a 3' terminus of a strand of an siRNA. Preferred modifications are internal modifications, for example, sugar modifications, nucleobase modifications and/or backbone modifications. Such modifications are also useful to improve uptake of the siRNA by a cell. Functional and genomic and proteomic methods are featured. Therapeutic methods are also featured.

BRIEF DESCRIPTION OF THE DRAWINGS

FIG. 1A-D depicts a dual fluorescence reporter assay system for RNAi analysis in HeLa cells. (A) Graphical representation of dsRNAs used for targeting GFP mRNA and RFP mRNA. GFP and RFP were encoded by the pEGFP-C1 and pDsRed1-N1 reporter plasmid, respectively. siRNAs were synthesized with 2-nt deoxythymidine overhangs at the 3' end. The position of the first nucleotide of the mRNA target site is indicated relative to the start codon of GFP mRNA or RFP mRNA. The sequence of the antisense strand of siRNA is exactly complementary to the mRNA target site. (B) Fluorescence images showing specific RNA interference effects in living HeLa cells. Fluorescence in living cells was visualized by fluorescence microscopy at 48 hours post transfection. Panels a and b, images of mock-treated cells (no siRNA added); panels c and d, images of GFP siRNA-treated cells; panels e and f, images of RFP siRNA-treated cells. (C) Quantitative analysis of RNAi effects in HeLa cells. Fluorescence emission spectra of GFP and RFP in total cell lysates were detected by exciting at 488 nm and 568 nm, respectively. (D) Kinetics of RNAi effects in HeLa cells. Ratios of normalized GFP to RFP fluorescence intensity over a 66-hour time course. The fluorescence intensity ratio of target (GFP) to control (RFP) protein was determined in the presence of double strand (ds) RNA (green bars) and normalized to the ratio observed in the presence of antisense strand (as) RNA (blue bars). Normalized ratios less than 1.0 indicate specific RNA interference. Maximal RNAi effect occurred at 42 hours post transfection.

FIG. 2A-B depicts the modification of GFP siRNA duplexes. (A) Structure of 5'-N3 (amino group with 3-carbon linker, red) and 3'-Pmn (puromycin, blue) modifications. (B) Classification and nomenclature of the modified siRNAs. Sense (top row, purple) and antisense (bottom row, black) strands of siRNA species are shown with their 5'-N3 (red) and 3'-Pmn or biotin (blue) modifications. A dinucleotide internal bulge structure (green) was introduced in sense, antisense, or duplex RNAs.

FIG. 7 depicts the isolation of psoralen-cross-linked siRNA from human cells. siRNA duplexes were conjugated with 3' biotin (ss/as3'-Biotin), psoralen cross-linked and purified as described in FIG. 6 and in Experimental Procedures. HeLa cells were cotransfected by lipofectamine with cross-linked siRNA (ss/as3'-Biotin-XL) and pEGFP-C1 plasmid, and siRNA were isolated by biotin pull out assay at 30 h post transfection as described in Experimental Procedures. Briefly, streptavidin-magnetic beads with biotinylated siRNA were subjected to phosphatase treatment and 5' end-labeled with $^{32}$P. RNA was resolved on 20% polyacrylamide-7M urea gels and visualized by phosphorimager analysis. Lane 1, RNA from HeLa cells without siRNA transfection. Lane 2, $^{32}$P-labeled noncross-linked siRNA duplex (ss/as3'-Biotin). Lane 3, $^{32}$P-labeled 3' biotinylated anti-sense strand siRNA (as3'-Biotin). Lane 4, $^{32}$P-labeled sense strand RNA (ss). Lane 5, $^{32}$P-labeled cross-linked siRNA duplex (ss/as3'-Biotin-XL). Lanes 7 and 8, siRNA isolated from HeLa cells treated with cross-linked siRNA duplex (ss/as3'-Biotin-XL). Lanes 6 and 8, UV-irradiation (254 nm) of cross-linked siRNA to photoreverse the psoralen cross-links.

FIG. 10A-E depicts a quantitative analysis of RNAi effects in HeLa cells transfected with modified duplex siRNAs. (A) depicts the results from cells treated with duplex siRNA with 2'-Deoxy modification at internal residues within the sense strand (ss-2'Deoxy/as, lanes 6-11). (B) depicts results from cells treated with duplex siRNA with 2'-O-Methyl modification at internal residues within the sense strand (ss-2'Ome/as, lanes 6-11) or the antisense strand (ss/as-2'-Ome, lanes 12-17). (C) depicts dual fluorescence assay data of 2'FU, FC siRNAs, modified only in the sense strand (ss-2'FU, 2'-FC/as, lanes 6-15), only in the antisense strand (ss/as-2'-FU,2'-FC, lanes 16-25), or in both strands (ds-2'FU,2'FC, lanes 26-35). (D) depicts results from cells treated with duplex siRNA with phosphorothioate modification at each backbone residue of the sense strand (ss-P-S-all/as, lanes 6-12), antisense strand (ss/as-P-S-all, lanes 13-22) and both strands (ds-P-S-all, lanes 23-31). (E) depicts results from cells treated with duplex siRNA with phosphorothioate modification at each backbone residue of both strands except for bases 9-12 of the antisense strand (ds-P-S, except center region, lanes 15-23).

FIG. 12A-E depicts the stability of duplex siRNA with 2'-Fluoro uridine and cytidine modification in HeLa cell lysates. (A) depicts a stability comparison of unmodified and modified antisense strand siRNA. (B) depicts a stability comparison of duplex siRNAs with unmodified and modified antisense strand. (C) depicts a stability comparison of duplex siRNAs containing modification at both strands. (D) shows the stability of the various 2'FU, FC modified siRNAs as compared to wild type siRNAs over time. (E) depicts the stability of P-S modified EGFP siRNAs.

FIG. 13A-D depicts a quantitative analysis of RNAi effects of duplex siRNAs with 2'-Fluoro uridine and cytidine modifications, and 2'-Fluoro uridine and cytidine modifications in combination with 2'-deoxy modifications, in HeLa cells. (A) depicts modified siRNA duplexes with modifications in the antisense strand at the 2' position of the sugar unit. (B) depicts data from cells treated with duplex siRNA with modified antisense strands. (C) depicts siRNA duplexes with modifications in both strands at the 2' position of the sugar unit. (D) results from cells treated with duplex siRNA with modifications in both strands as set forth in FIG. 13C.

FIG. 15A-C depicts a quantitative analysis of RNAi effects of duplex siRNAs with 2-nucleotide mismatches in the antisense strand in HeLa cells. (A) depicts results suggesting that a single cross-linking event occurring near the 3' end of the antisense strand still allowed for the initial unwinding of duplex siRNAs from the 5' end, freeing enough of the nucleotides in the antisense strand to hybridize to the target mRNA and induce RNAi, even if unwinding was not complete. The location of this crosslinking site is indicated by a bar in FIG. 15A. (B) depicts EGFP siRNAs with mismatched base pairs at either the 5' (nt 1, 2) or 3' (nt 18, 19) ends were introduced into the antisense strand. (C) depicts data of Example XIII, wherein 2'FU, FC plus dATPs, dGTPs were incorporated into the antisense strand siRNAs predominantly at the 5' end (nts 1-13) or predominantly at the 3' end (nts 9-19).

DETAILED DESCRIPTION OF THE INVENTION

Figure 1C:
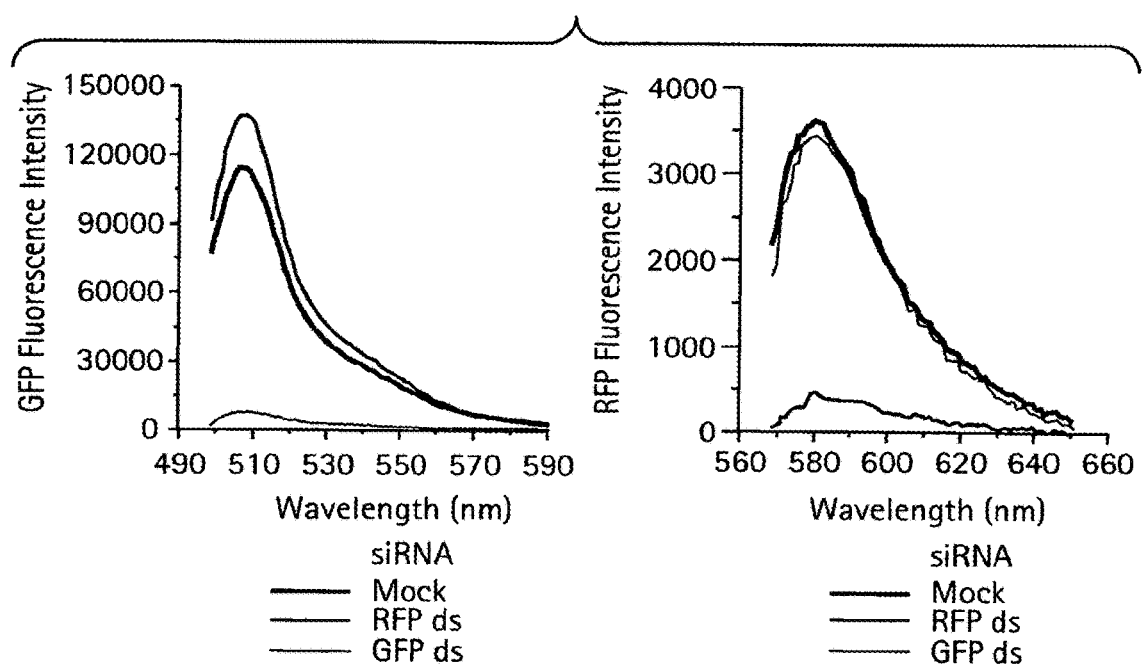

The present invention is based on the suprising discovery that siRNA molecules (i.e., duplex siRNA molecules) can be modified at internal residues such that properties important for in vivo applications, in particular, human therapeutic applications, are improved without compromising the RNAi activity of the siRNA molecules. The instant invention features siRNAs having significant modification to internal residues within the siRNA, providing new rules for designing effective and stable siRNAs for RNAi-mediated gene-silencing applications. Most remarkably, modifications at the 2' position of pentose sugars in siRNAs showed that 2'OH groups are not required for RNAi, indicating that the RNAi machinery does not require the 2'OH for recognition of siRNAs and that catalytic ribonuclease activity of RNA-induced silencing complexes (RISC) does not involve the 2'OH of the guide antisense RNA. In fact, the instant inventor was able to replace an entire siRNA strand with 2' deoxy- and 2' fluoro-nucleotides and still induce RNAi in human cells.

This is a significant finding for several reasons. First, it indicates that, mechanistically, the RNAi machinery does not require the 2' OH for recognition of siRNAs and that the catalytic ribonuclease activity of RISC does not involve 2' OH groups of the guide antisense RNA. This also means that a variety of chemical groups, including fluoro- or deoxy-groups, could substitute for the 2'OH in siRNAs and that no distinguishing chemical specificity was required for RNAi at the 2' position. This finding now directs attention to core structural elements, like the A-form helix and the major groove formed by the A-form helix at the cleavage site and not RNA itself, as being the essential determinants of RNAi. These findings are particularly useful in the design of effective siRNAs. It also explains why DNA-DNA or DNA-RNA hybrids are not recognized for RNAi. Differences between the miRNA-induced silencing mechanism and siRNA-mediated RNAi are further explained by these results in that what distinguishes whether one is induced over the other is the structure of the RNA-RNA helix. Still another important implication of these results is that alternate chemical groups at the 2' position that allow the A-form helix to be retained but help siRNAs evade recognition by RNases increased siRNA stability and prolonged RNAi effects induced in vivo.

Such modifications have the added feature of enhancing properties such as cellular uptake of the siRNAs and/or stability of the siRNAs. Preferred modifications are made at the 2' carbon of the sugar moiety of nucleotides within the siRNA. Also preferred are certain backbone modifications, as described herein. Also preferred are chemical modifications that stabilize interactions between base pairs, as described herein. Combinations of substitution are also featured. Preferred modifications maintain the structural integrity of the antisense siRNA-target mRNA duplex. Methods of mediating RNAi in mammals, preferably humans, are featured as are kits for such therapeutic use.

The present invention features modified siRNAs. siRNA modifications are designed such that properties important for in vivo applications, in particular, human therapeutic applications, are improved without compromising the RNAi activity of the siRNA molecules e.g., modifications to increase resistance of the siRNA molecules to nucleases. Modified siRNA molecules of the invention comprise a sense strand and an antisense strand, wherein the sense strand or antisense strand is modified by the substitution of at least one nucleotide with a modified nucleotide, such that, for example, in vivo stability is enhanced as compared to a corresponding unmodified siRNA, or such that the target efficiency is enhanced compared to a corresponding unmodified siRNA. Such modifications are also useful to improve uptake of the siRNA by a cell. Preferred modified nucleotides do not effect the ability of the antisense strand to adopt A-form helix conformation when base-pairing with the target mRNA sequence, e.g., an A-form helix conformation comprising a normal major groove when base-pairing with the target mRNA sequence.

Modified siRNA molecules of the invention (i.e., duplex siRNA molecules) can be modified at the 5' end, 3' end, 5' and 3' end, and/or at internal residues, or any combination thereof. Internal siRNA modifications can be, for example, sugar modifications, nucleobase modifications, backbone modifications, and can contain mismatches, bulges, or crosslinks. Also preferred are 3' end, 5' end, or 3' and 5' and/or internal modifications, wherein the modifications are, for example, cross linkers, heterofunctional cross linkers, dendrimer, nano-particle, peptides, organic compounds (e.g., fluorescent dyes), and/or photocleavable compounds.

In one embodiment, the siRNA molecule of the invention comprises one or more (e.g., about 1, 2, 3, 4, 5, 6, 7, 8, 9, 10, or more) end modifications. Modification at the 5' end is preferred in the sense strand, and comprises, for example, a 5'-propylamine group. Modifications to the 3' OH terminus are in the sense strand, antisense strand, or in the sense and antisense strands. A 3' end modification comprises, for example, 3'-puromycin, 3'-biotin and the like.

In another embodiment, the siRNA molecule of the invention comprises one or more (e.g., about 1, 2, 3, 4, 5, 6, 7, 8, 9, 10, or more) crosslinks, e.g., a crosslink wherein the sense strand is crosslinked to the antisense strand of the siRNA duplex. Crosslinkers useful in the invention are those commonly known in the art, e.g., psoralen, mitomycin C, cis-platin, chloroethylnitrosoureas and the like. A preferred crosslink of the invention is a psoralen crosslink. Preferably, the crosslink is present downstream of the cleavage site referencing the antisense strand, and more preferably, the crosslink is present at the 5' end of the sense strand.

In another embodiment, the siRNA molecule of the invention comprises one or more (e.g., about 1, 2, 3, 4, 5, 6, 7, 8, 9, 10, or more) sugar-modified nucleotides. Sugar-modifed nucleotides useful in the invention include, but are not limited to: 2'-fluoro modified ribonucleotide, 2'-OMe modified ribonucleotide, 2'-deoxy ribonucleotide, 2'-amino modified ribonucleotide and 2'-thio modified ribonucleotide. The sugar-modified nucleotide can be, for example, 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine or 2'-amino-butyryl-pyrene-uridine. A preferred sugar-modified nucleotide is a 2'-deoxy ribonucleotide. Preferably, the 2'-deoxy ribonucleotide is present within the sense strand and, for example, can be upstream of the cleavage site referencing the antisense strand or downstream of the cleavage site referencing the antisense strand. A preferred sugar-modified nucleotide is a 2'-fluoro modified ribonucleotide. Preferably, the 2'-fluoro ribonucleotides are in the sense and antisense strands. More preferably, the 2'-fluoro ribonucleotides are every uridine and cytidine.

In another embodiment, the siRNA molecule of the invention comprises one or more (e.g., about 1, 2, 3, 4, 5, 6, 7, 8, 9, 10, or more) nucleobase-modified nucleotides. Nucleobase-modified nucleotides useful in the invention include, but are not limited to: 5-bromo-uridine, 5-iodo-uridine, 5-methyl-cytidine, ribo-thymidine, 2-aminopurine, 5-fluoro-cytidine, and 5-fluoro-uridine, 2,6-diaminopurine, 4-thio-uridine; and 5-amino-allyl-uridine and the like.

In another embodiment, the siRNA molecule of the invention comprises one or more (e.g., about 1, 2, 3, 4, 5, 6, 7, 8, 9, 10, or more) backbone-modified nucleotides, for example, a backbone-modified nucleotide containing a phosphorothioate group. The backbone-modified nucleotide is within the sense strand, antisense strand, or preferably within the sense and antisense strands.

In another embodiment, the siRNA molecule of the invention comprises a sequence wherein the antisense strand and target mRNA sequences comprise one or more (e.g., about 1, 2, 3, 4, 5, 6, 7, 8, 9, 10, or more) mismatches. Preferably, the mismatch is downstream of the cleavage site referencing the antisense strand. More preferably, the mismatch is present within 1-6 nucleotides from the 3' end of the antisense strand. In another embodiment, the siRNA molecule of the invention comprises a bulge, e.g., one or more (e.g., about 1, 2, 3, 4, 5, 6, 7, 8, 9, 10, or more) unpaired bases in the duplex siRNA. Preferably, the bulge is in the sense strand.

In another embodiment, the siRNA molecule of the invention comprises any combination of two or more (e.g., about 2, 3, 4, 5, 6, 7, 8, 9, 10, or more) siRNA modifications as described herein. For example, a siRNA molecule can comprise a combination of two sugar-modified nucleotides, wherein the sugar-modified nucleotides are 2'-fluoro modified ribonucleotides, e.g., 2'-fluoro uridine or 2'-fluoro cytidine, and 2'-deoxy ribonucleotides, e.g., 2'-deoxy adenosine or 2'-deoxy guanosine. Preferably, the 2'-deoxy ribonucleotides are in the antisense strand, and, for example, can be upstream of the cleavage site referencing the antisense strand or downstream of the cleavage site referencing the antisense strand. Preferably, the 2'-fluoro ribonucleotides are in the sense and antisense strands. More preferably, the 2'-fluoro ribonucleotides are every uridine and cytidine.

The invention is also related to the discovery that certain characteristics of siRNA are necessary for activity and that modifications can be made to an siRNA to alter physicochemical characteristics such as stability in a cell and the ability of an siRNA to be taken up by a cell. Accordingly, the invention includes siRNA derivatives; siRNAs that have been chemically modified and retain activity in RNA interference (RNAi). The invention also includes a dual fluorescence reporter assay (DFRA) that is useful for testing the activity of siRNAs and siRNA derivatives.

Accordingly, the invention includes an siRNA derivative that includes an siRNA having two complementary strands of nucleic acid, such that the two strands are crosslinked, a 3' OH terminus of one of the strands is modified, or the two strands are crosslinked and modified at the 3'OH terminus. The siRNA derivative can contain a single crosslink (e.g., a psoralen crosslink). In some embodiments, the siRNA derivative has a biotin at a 3' terminus (e.g., a photocleavable biotin such as the novel photocleavable biotin of FIG. 8), a peptide (e.g., a Tat peptide), a nanoparticle, a peptidomimetic, organic compounds (e.g., a dye such as a fluorescent dye), or dendrimer.

The invention also includes a method of inhibiting expression of an RNA. The method includes the steps of introducing into a cell an siRNA derivative such as those described herein, and such that the siRNA derivative is targeted to the RNA.

The invention also includes a method that includes the step of contacting a cell with a concentration of an siRNA derivative sufficient to inhibit expression of a target gene. In some embodiments, the siRNA derivative is a crosslinked siRNA (e.g., contains a single crosslink), is modified at a 3' terminus, contains a biotin at a 3' terminus, contains a photocleavable biotin having the structure depicted in FIG. 8 at a 3' terminus, or contains a peptide (e.g., a Tat peptide), nanoparticle, peptidomimetic, organic molecule (e.g., a fluorescent dye), or dendrimer at a 3' terminus. In some embodiments of the method, the siRNA derivative inhibits expression of the target gene at least 30%. The cell can be a mammalian cell (e.g., human cell). In some cases, the concentration of the siRNA derivative administered to the cell or within the cell does not completely inhibit expression of the target gene. In some embodiments, the modified siRNA is carried out in the absence of a transfection reagent.

Figure 20:
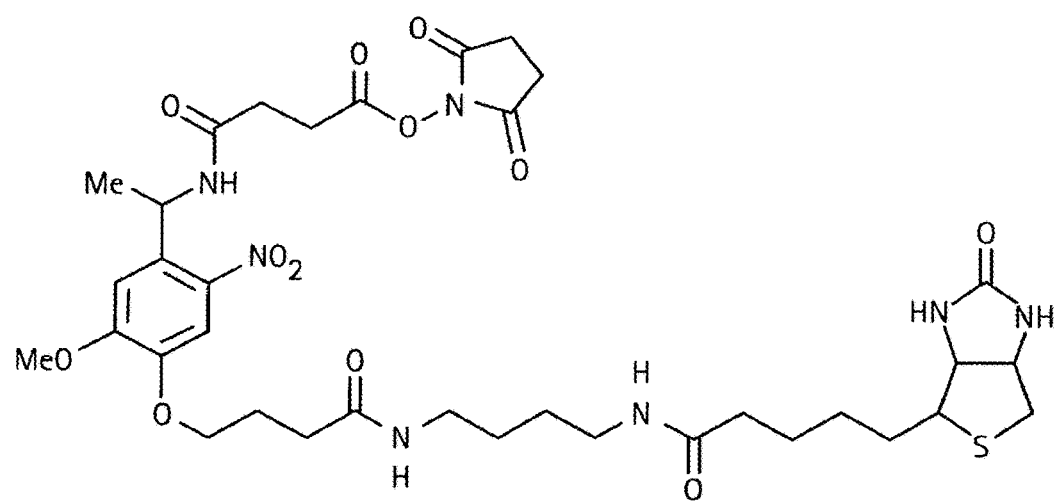
FIG. 20 is a drawing of the structure of a novel photocleavable biotin.

The invention includes a novel photocleavable biotin of the formula depicted in FIG. 20, and the method of synthesizing the compound.

Exemplary siRNAs to be modified according to the methodologies described herein are siRNAs targeting transcription elongation factors (TEFs), in particular, DSIF and P-TEFb, as well as siRNAs targeting subunits of said TEFs, in particular, CycT1, CDK9 and Spt5. siRNAs targeting TEFs are described in detail herein and in PCT/US03/24610. All combinations of modifications described herein and siRNAs (and other RNAi agents) described, for example, in PCT/US03/24610, are the intended scope of the instant patent application. Methods as described herein and, for example, in PCT/US03/24610, featuring modified siRNAs (or RNAi agents) as described herein are further the intended scope of the instant patent application.

So that the invention may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference.

The term "nucleotide analog", also referred to herein as an "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function.

The term "oligonucleotide" refers to a short polymer of nucleotides and/or nucleotide analogs. The term "RNA analog" refers to an polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phophoroamidate, and/or phosphorothioate linkages. Exemplary RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

A siRNA having a "sequence sufficiently complementary to a target mRNA sequence to direct target-specific RNA interference (RNAi)" means that the siRNA has a sequence sufficient to trigger the destruction of the target mRNA by the RNAi machinery or process.

The term "cleavage site" refers to the residues, e.g. nucleotides, at which RISC* cleaves the target RNA, e.g., near the center of the complementary portion of the target RNA, e.g., about 8-12 nucleotides from the 5' end of the complementary portion of the target RNA. The term "upstream of the cleavage site" refers to residues, e.g., nucleotides or nucleotide analogs, 5' to the cleavage site. Upstream of the cleavage site with reference to the antisense strand refers to residues, e.g. nucleotides or nucleotide analogs 5' to the cleavage site in the antisense strand.

The term "downstream of the cleavage site" refers to residues, e.g., nucleotides or nucleotide analogs, located 3' to the cleavage site. Downstream of the cleavage site with reference to the antisense strand refers to residues, e.g., nucleotides or nucleotide analogs, 3' to the cleavage site in the antisense strand.

The term "mismatch" refers to a basepair consisting of noncomplementary bases, e.g. not normal complementary G:C, A:T or A:U base pairs.

The term "phosphorylated" means that at least one phosphate group is attached to a chemical (e.g., organic) compound. Phosphate groups can be attached, for example, to proteins or to sugar moieties via the following reaction: free hydroxyl group+phosphate donor→phosphate ester linkage. The term "5' phosphorylated" is used to describe, for example, polynucleotides or oligonucleotides having a phosphate group attached via ester linkage to the C5 hydroxyl of the 5' sugar (e.g., the 5' ribose or deoxyribose, or an analog of same). Mono-, di-, and triphosphates are common. Also intended to be included within the scope of the instant invention are phosphate group analogs which function in the same or similar manner as the mono-, di-, or triphosphate groups found in nature (see e.g., exemplified analogs.)

As used herein, the term "isolated" molecule (e.g., isolated nucleic acid molecule) refers to molecules which are substantially free of other cellular material, or culture medium when produced by recombinant techniques, or substantially free of chemical precursors or other chemicals when chemically synthesized.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

A target gene is a gene targeted by a compound of the invention (e.g., a siRNA (targeted siRNA), candidate siRNA derivative, siRNA derivative, modified siRNA, etc.), e.g., for RNAi-mediated gene knockdown. One portion of an siRNA is complementary (e.g., fully complementary) to a section of the mRNA of the target gene.

A gene "involved" in a disorder includes a gene, the normal or aberrant expression or function of which effects or causes a disease or disorder or at least one symptom of said disease or disorder The phrase "examining the function of a gene in a cell or organism" refers to examining or studying the expression, activity, function or phenotype arising therefrom.

Various methodologies of the instant invention include step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing a siRNA of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

A cell or culture that has not been contacted with a modified siRNA or an siRNA derivative is a control cell or control culture. The control cell or control culture generally contains one or more reporter genes that are expressed or one or more endogenous genes of interest, e.g., for RNAi-mediated knockdown. In some embodiments of the invention, the control cell or control culture contains an siRNA targeted to a reporter gene or to an endogenous gene of interest. In some cases, the control cell or control culture contains an introduced control sequence such as an antisense strand corresponding to the antisense strand of an siRNA or modified siRNA.

A test cell or test culture contains one or more reporter genes that are expressed or one or more expressed endogenous genes of interest, e.g., for RNAi-mediated gene knockdown, and also contains a modified siRNA or siRNA derivative targeted to a reporter gene or to an endogenous gene of interest.

Various aspects of the invention are described in further detail in the following subsections.

I. siRNA Molecules

The present invention features "small interfering RNA molecules" ("siRNA molecules" or "siRNA"), methods of making said siRNA molecules and methods (e.g., research and/or therapeutic methods) for using said siRNA molecules. An siRNA molecule of the invention is a duplex consisting of a sense strand and complementary antisense strand, the antisense strand having sufficient complementarity to a target mRNA to mediate RNAi. Preferably, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. Preferably, the siRNA molecule has a length from about 10-50 or more nucleotides, i.e., each strand comprises 10-50 nucleotides (or nucleotide analogs). More preferably, the siRNA molecule has a length from about 15-45 nucleotides. Even more preferably, the siRNA molecule has a length from about 18-25 nucleotides. The siRNA molecules of the invention further have a sequence that is "sufficiently complementary" to a target mRNA sequence to direct target-specific RNA interference (RNAi), as defined herein, i.e., the siRNA has a sequence sufficient to trigger the destruction of the target mRNA by the RNAi machinery or process.

The target RNA cleavage reaction guided by siRNAs (e.g., by siRNAs) is highly sequence specific. In general, siRNA containing a nucleotide sequences identical to a portion of the target gene are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Moreover, not all positions of a siRNA contribute equally to target recognition. Mismatches in the center of the siRNA are most critical and essentially abolish target RNA cleavage. Mismatches upstream of the center or upstream of the cleavage site referencing the antisense strand are tolerated but significantly reduce target RNA cleavage. Mismatches downstream of the center or cleavage site referencing the antisense strand, preferably located near the 3' end of the antisense strand, e.g. 1, 2, 3, 4, 5 or 6 nucleotides from the 3' end of the antisense strand, are tolerated and reduce target RNA cleavage only slightly.

Sequence identity may determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) *Nucleic Acids Res.* 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, *CABIOS* (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 90% sequence identity, e.g., 91%, 92%, 93%, 94%, 95%, 96%, 97%, 98%, 99% or even 100% sequence identity, between the siRNA and the portion of the target gene is preferred. Alternatively, the siRNA may be defined functionally as a nucleotide sequence (or oligonucleotide sequence) that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm (° C.)=2(# of A+T bases)+4(# of G+C bases). For hybrids between 18 and 49 base pairs in length, Tm (° C.)=81.5+ 16.6(log 10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3-6.4, incorporated herein by reference. The length of the identical nucleotide sequences may be at least about 10, 12, 15, 17, 20, 22, 25, 27, 30, 32, 35, 37, 40, 42, 45, 47 or 50 bases.

In a preferred aspect, the invention features small interfering RNAs (siRNAs) that include a sense strand and an antisense strand, wherein the antisense strand has a sequence sufficiently complementary to a target mRNA sequence to direct target-specific RNA interference (RNAi) and wherein the sense strand and/or antisense strand is modified by the substitution of internal nucleotides with modified nucleotides, such that in vivo stability is enhanced as compared to a corresponding unmodified siRNA. As defined herein, an "internal" nucleotide is one occurring at any position other than the 5' end or 3' end of nucleic acid molecule, polynucleotide or oligonucleoitde. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In yet another embodiment, the modified nucleotides are present only in the antisense strand. In yet another embodiment, the modified nucleotides are present only in the sense strand. In yet other embodiments, the modified nucleotides are present in both the sense and antisense strand.

Preferred modified nucleotides or nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' moiety is a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Preferred are 2'-fluro, 2'-amino and/or 2'-thio modifications. Particularly preferred modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine; and/or 5-amino-allyl-uridine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides can be used within modified siRNAs of the instant invention, but are preferably included within the sense strand of the siRNA duplex. 2'-OMe nucleotides are less preferred. Additional modified residues have been described in the art and are commercially available but are less preferred for use in the modified siRNAs of the instant invention including, deoxy-abasic, inosine, N3-methyl-uridine, N6, N6-dimethyl-adenosine, pseudouridine, purine ribonucleoside and ribavirin. Modification of the linkage between nucleotides or nucleotide analogs is also preferred, e.g., substitution of phosphorothioate linkages for phosphodiester linkages.

Also possible are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable.

It should be noted that all modifications described herein may be combined. In a preferred embodiment, 2'-fluoro modified ribonucleotides and 2'-deoxy ribonucleotides are combined and both are present within the antisense strand.

Preferably, an siRNA molecule of the invention will have a three-dimensional structure resembling A-form RNA helix. More preferably, an siRNA molecule of the invention will have an antisense strand which is capable of adopting an A-form helix when in association with a target RNA (e.g., an mRNA). For this reason, 2'-fluro-modified nucleotides are preferred, as siRNA made with such modified nucleotides adopts an A-form helix confirmation. In particular, it is important that an siRNA be capable of adopting an A-form helix in the portion complementary to the target cleavage site as it has been discovered that the major groove formed by the A-form helix at the cleavage site, and not the RNA itself, is an essential determinant of RNAi. More preferably, a siRNA molecule will have exhibit increased cellular uptake when contacted with a cell, e.g., a human cell, as compared to an unmodified siRNA molecule. Even more preferably, a siRNA molecule will exhibit increased stability (i.e, resistance to cellular nucleases) as compared to an unmodified siRNA molecule.

II. siRNA Derivatives

Discoveries have been made that elucidate certain mechanisms of RNAi. These discoveries indicate that the status of the 5' hydroxyl terminus of the antisense strand of an siRNA determines RNAi activity, whereas a 3' terminus block is well tolerated in living cells. Furthermore, isolation of siRNA from human cells has revealed that 5' hydroxyl termini of the antisense strands are phosphorylated. It has also been discovered that biotin, chemically linked to the 3' terminus of an siRNA (e.g., a type of siRNA derivative), is not efficiently removed and that siRNAs having such 3' biotins are effective in RNAi. In addition, it has been found that there is no requirement for a perfect A-form helix in siRNA for interference effects, but an A-form structure is required for antisense-target RNA duplexes. Strikingly, crosslinking of the siRNA duplex by psoralen does not completely block RNA interference, indicating that complete unwinding of the siRNA helix is not necessary for RNAi activity in vivo. These results highlight the importance of 5' hydroxyl in the antisense strand of siRNA, which is essential to initiate the RNAi pathway. Contrary to current beliefs, these data show that RNA amplification by RNA-dependent RNA polymerase is not essential for RNAi in mammalian (e.g., human) cells.

Based on these discoveries, the invention includes modifications to siRNA to create corresponding siRNA derivatives. The siRNA to be modified can be naturally occurring or synthetic. Modifications include altering a 3' OH end of an siRNA to create a corresponding siRNA derivative with a new property such as increased stability or a label. In some embodiments, siRNA is modified by crosslinking between one or more pairs of nucleotides in an siRNA, thereby creating another type of siRNA derivative. The invention also includes a novel photocleavable biotin that is, for example, useful for labeling a 3' OH terminus of an siRNA.

In some aspects the invention relates to siRNA derivatives. An siRNA derivative is a double-stranded RNA-based structure that is 15-30 nucleotides in length (e.g., 15-25 or in some cases, 21-25 nucleotides in length), has certain features in common with a corresponding siRNA (an siRNA targeted to the same sequence as the siRNA derivative) such as the ability to inhibit expression of a target sequence. The sequence of the antisense strand of an siRNA or an siRNA derivative is exactly complementary to at least a portion of the target mRNA. An siRNA typically has a 2-3 nucleotide 3' overhanging end, a 5' phosphate (upon extraction from a cell) and a 3' hydroxyl terminus. In addition, an siRNA derivative has at least one of the following which is not a feature of siRNA: a label at the 3' terminus (e.g., biotin or a fluorescent molecule, the 3' terminus is blocked, the 3' terminus has a covalently linked group or compound (e.g., a nanoparticle or a peptide), the siRNA derivative does not form a perfect A-form helix, but the antisense strand of the siRNA derivative duplex does form an A-form helix with target RNA, or the siRNA derivative is crosslinked (e.g., by psoralen). Methods of synthesizing RNAs and modifying RNAs are known in the art (e.g., Hwang et al., 1999, Proc. Nat. Acad. Sci. USA 96:12997-13002; and Huq and Rana, 1997, Biochem. 36:12592-12599).

In some embodiments of the invention, an siRNA derivative also exhibits a relatively low level of toxicity. For example, a concentration of an siRNA derivative that inhibits expression of a targeted sequence has relatively low toxicity when at least 50% of the cells in a culture treated with the siRNA derivative are viable when expression of the targeted sequence is decreased by 50% compared to expression in a cell that is not treated with the siRNA derivative. Low toxicity may be associated with greater cell viability, e.g., at least 60%, 75%, 85%, 90%, 95%, or 100%. Methods of measuring cell viability are known in the art and include trypan blue exclusion.

RNAi provides a new approach for elucidation of gene function and for inhibiting expression of undesirable genes, which is also known as "gene knockdown." RNAi-mediated gene knockdown is useful for, e.g., genome-wide analysis of gene function, target validation of potentially therapeutic genes, and therapies based on the elimination, reduction, or elimination of expression of a specific gene product. In addition, siRNAs are useful tools for cell biologists studying mammalian gene function. For example, siRNAs are useful for the analysis of general cell biological mechanisms such as mitosis, processing and trafficking of RNA transcripts, the formation of cellular junctions, and membrane trafficking. Reagents that can be used for such analyses (e.g., modified siRNAs with increased stability or functional groups that endow an siRNA with additional properties) have commercial value for use in such research.

The invention provides siRNAs that have been chemically modified. Certain modifications confer useful properties to siRNA. For example, increased stability compared to an unmodified siRNA or a label that can be used, e.g., to trace the siRNA, to purify an siRNA, or to purify the siRNA and cellular components with which it is associated. Certain modifications can also increase the uptake of the siRNA by a cell.

RNAi-mediated gene knockdown can cause a phenotype that is lethal or toxic for a cell or the siRNA used to target a gene for knockdown may affect multiple pathways in the cell. Therefore, chemically modified siRNAs (siRNA derivatives) that are less efficient than the corresponding siRNA are still useful in some applications of RNAi. SiRNA derivatives containing certain functional groups such as biotin are useful for affinity purification of proteins and molecular complexes involved in the RNAi mechanism. The invention also includes methods of testing modified siRNAs for retention of the ability to act as an siRNA (e.g., in RNAi) and methods of using siRNA derivatives.

A. Crosslinked siRNA Derivatives

Some embodiments include the use of siRNAs that contain one or more crosslinks between nucleic acids in the complementary strands of the siRNA. Crosslinks can be introduced into an siRNA using methods known in the art. In addition to crosslinking using psoralen (e.g., Example 1 and Example 9, infra; Wang et al., 1996, J. Biol. Chem. 271:16995-16998) other methods of crosslinking can be used. In some embodiments, photocrosslinks are made containing thiouracil (e.g., 4-thiouridine) or thioguanosine bases. In other embodiments, —SH linkers can be added to the bases or sugar backbones, which are used to make S—S crosslinks. In some cases, sugar backbones or amino groups at the C5 position of U, C can be labeled with benzophenone and other photo crosslinkers or with chemical crosslinkers. Methods of making such crosslinks are known in the art (e.g., Wang and Rana, 1998, Biochem. 37:4235-4243; Bio-Mosaics, Inc., Burlington, Vt.). In general, the stability in a cell or a cell-free system of a crosslinked siRNA derivative is greater than that of the corresponding siRNA. In some cases, the crosslinked siRNA derivative has less activity than the corresponding siRNA. The ability of a crosslinked siRNA to inhibit expression of a target sequence can be assayed using methods known in the art for testing the activity of an siRNA or by methods disclosed herein such as a dual fluorescence reporter gene assay.

In general, an siRNA derivative that is crosslinked contains one crosslink between two nucleotides of a dsRNA sequence. In some embodiments, there are two or more crosslinks. Crosslinks are generally located near the 3' terminus of the antisense strand, e.g., within about 10 nucleotides of the 3' terminus of the antisense strand, and generally within about 2-7 nucleotides of the 3' terminus of the antisense strand. A crosslink is to be distinguished from ligation that joins the ends of the two strands of an siRNA. A mixture of crosslinked siRNA derivatives that contains some molecules crosslinked at loci near the middle of the siRNA or near the 5' terminus of the antisense strand can also be useful. Such mixtures can have less activity than a mixture of siRNA derivative that is crosslinked exclusively near the 3' terminus, but retain sufficient activity to affect expression of a targeted sequence.

B. 3' Modifications of siRNA

It has been discovered that the 3' terminus of siRNA is not critical for activity in RNAi. Therefore, modifications can be made to an siRNA to create an siRNA derivative. For example, molecules that are used for affinity purification or as detectable tags can be covalently linked to the 3' terminus of an RNAi to create an siRNA derivative. Such RNAi derivatives are useful, e.g., for assaying an siRNA by transfecting a cell with an siRNA derivative of the siRNA containing a detectable tag at the 3' end and detecting the tag using methods known in the art. Examples of such tags that can be used for detection or affinity purification of derivative siRNAs include biotin.

Methods that can be used to modify an siRNA are known in the art. For example, crosslinkers can be attached using amino-allyl coupling methods, e.g., isothiocyanate, N-hydroxysuccinimide (NHS) esters (Amersham Biosciences Corp., Piscataway, N.J.). A number of different types of molecules can be attached to a 3' terminus using such methods including dyes (e.g., Dyomics, Germany; Integrated DNA Technologies, Coralville, Iowa, ATTO-TEC, Siegen, Germany), dendrimers (e.g., Dendritech, Midland, Mich.), and nanoparticles. Crosslinkers can be attached to amino-allyl uridine or amino groups at sugars using similar chemistry.

The invention includes conjugation of compounds to an siRNA. Primary amines are the principal targets for NHS esters. For example, NHS esters of biotin can be conjugated to free amino groups at the 3'-end of an siRNA duplex as described in the Examples.

In some embodiments, photocrosslinkers (e.g., thiouracil, thioguanosine, psoralens, benzophenones) are attached at 3' terminus of an siRNA to create an siRNA derivative. Methods of synthesizing such modifications are known in the art. Such an siRNA derivative can be crosslinked to the target cellular machinery in vitro and in vivo.

Other heterofunctional linkers can be used to modify the 3' termini of siRNAs, for example, to link a peptide or a peptidomimetic oligomer to an siRNA (e.g., Tamilarasu et al., 2001, Bioorganic & Medicinal Chemistry Letters 11:505-507). For example, one end of the pair to be linked (siRNA and peptide) can be made amine reactive and the other thiol reactive. SiRNA that has been modified in this fashion can be deprotected and linked to structures that, e.g., improve cellular uptake of the resulting siRNA derivative compared to uptake of the corresponding siRNA, are useful for tracing the siRNA derivative in the cell, or improve the stability of the siRNA derivative compared to the corresponding siRNA. Example 18 illustrates the use of such a modification in which a deprotected and purified modified siRNA was linked to Tat peptides, thereby improving cellular uptake of the siRNA. Such methods of attaching peptides, including Tat peptides, are known in the art (e.g., Wang et al., 2001, Biochemistry 40:6458-6464). Methods of synthesizing peptides and peptidomimetics are known in the art and can generally be obtained from commercial sources (e.g., AnaSpec, San Jose, Calif.).

In another embodiment, the 3' terminus of siRNA is labeled with dendrimer and/or nanoparticle structures that can enhance cellular targeting activities without causing any known toxic effects. In addition, certain dendrimers are useful for facilitating uptake of molecules into cells, thus covalent linkage of such a dendrimer to the 3' terminus of an siRNA can increase the efficiency of uptake into a cell of the resulting dendrimer siRNA derivative.

In other embodiments, a dyes can be linked to 3' termini of an siRNA. Such dyes include those that are useful for energy transfer and functional assays, e.g., of helicase activity. For example, a fluorescent donor dye such as isothiocyanate-fluorescein can be attached to the 3' end of the antisense strand of an siRNA. An acceptor dye (e.g., isothiocyanate rhodamine) can be attached to the 5' end. RNA-containing amino groups at the 3' or 5' end can be obtained from commercial sources or appropriate dyes can be purchased and the molecules synthesized (Integrated DNA Technologies, Coralville, Iowa). Such a modified siRNA can be incubated with RISC complex that contains helicase. Fluorescence resonance energy transfer (FRET) signals will be altered when the RNA helix of the modified siRNA is unwound.

Modification of the 3' end can also include attachment of photocleavable compounds such as biotin. This is illustrated in Example 19. RNAi derivatives with photocleavable compounds attached to the 3' terminus are useful, e.g., for isolating proteins and other molecular complexes that bind to an siRNA. For example, photocleavable biotin can be attached to an siRNA. The resulting derivative is incubated with a cell lysate or transfected into cells. After a suitable incubation time, the biotin siRNA derivative is retrieved using avidin attached to a substrate (e.g., beads). After washing, the biotin is photocleaved from the siRNA, thus releasing the siRNA and its interacting proteins. These proteins can then be subjected to further analysis using methods known in the art.

C. Photocleavable Biotin

The invention includes a method of synthesizing a novel photocleavable biotin that is depicted in FIG. 8. The novel photocleavable biotin is useful for methods in which photocleavable biotins are presently used such as the biotin pull out assay described in Examples 1 and 5. The advantage of this novel photocleavable biotin is its increased sensitivity compared to other photocleavable biotins that are presently known and commercially available. The advantages of the new photocleavable biotin disclosed herein include the following features of having a photolabile linker that is more efficiently cleaved, the compound contains a longer chain between the biotin and photolabile aromatic ring, and it makes an amide link with the target protein or other compound of interest. The novel photocleavable compound is an oxygenated nitrobenzyl system (in contrast to compounds having only a nitrobenzyl system) and cleaves efficiently when irradiated at 360 nm (J. Org. Chem., 1995, 60, 7328-7333; Burgess et al., 1997, *J. Org. Chem.* 62:5662-5663).

The synthesis of probe 6 (novel photocleavable biotin) consists of six reaction steps, which are depicted in the following scheme.

Scheme 1: Synthesis of the photolabile biotin probe

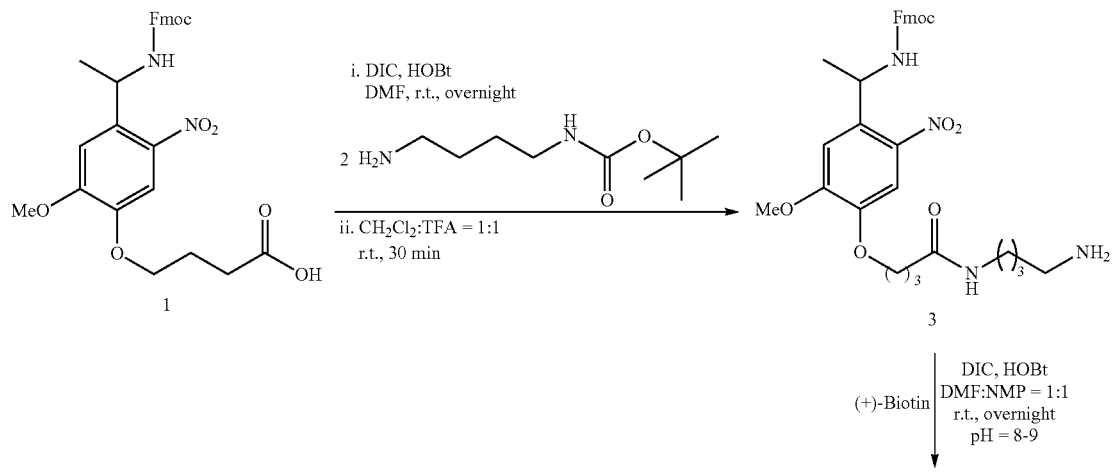

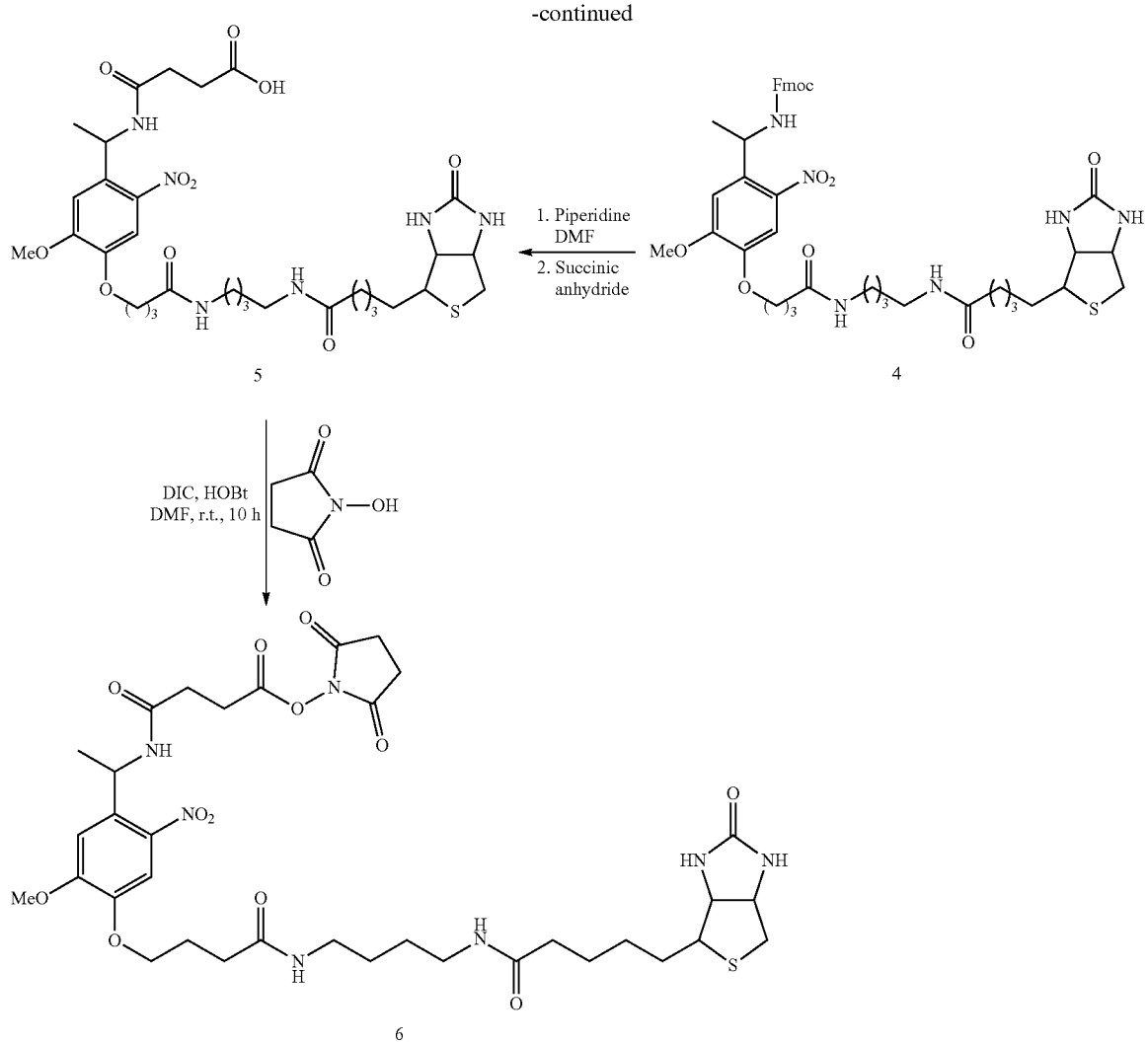

Synthesis of the amine 3: To prepare amine 3, a stirred solution of 0.50 g (0.96 mmol) of the photo-linker 1 in 5 ml of anhydrous DMF, was added 0.15 ml (0.96 mmol) of diisopropylcarbodiimide and 0.13 g (0.96 mmol) of HOBt. A solution of 0.18 g (0.96 mmol) of compound 2 was then added in 2 ml of DMF dropwise. The reaction mixture was then stirred overnight at room temperature. After the completion of the reaction (checked by TLC analysis), the solvent was evaporated at reduced pressure. Flash column chromatography on silica gel with 85:15=EtOAC:MeOH afforded 0.64 g (96.5%) of the pure product. To the product thus obtained, 25 ml of 1:1 $CH_2Cl_2$:TFA was added and the mixture was stirred at room temperature for 30 minutes. The solvent was evaporated and the crude product was co-evaporated twice in anhydrous DMF. This material is used for further coupling reactions.

Synthesis of the Biotinylated Product 4:

To synthesize biotinylated product 4, a mixture of 0.54 g (0.91 mmol) of compound 3, 0.15 ml (0.91 mmol) of diisopropylcarbodiimide, and 0.13 g (0.91 mmol) of HOBt in 5 ml of 1:1 DMF:NMP, was added to a solution of 0.23 g (0.91 mmol) of (+)-Biotin in 2 ml of NMP. The reaction mixture was then stirred at room temperature for 10 hours. After the completion of the reaction (as analyzed by HPLC), the solvent was removed under reduced pressure. Excess reagents and impurities were then removed by precipitating the product 4 in a mixture of 90:10 $CH_2Cl_2$:MeOH to afford 0.69 g (92.5%) of the pure product.

Synthesis of the Acid 5:

To a stirred solution of 0.69 g (0.85 mmol) of 4 in 10 ml of anhydrous DMF, was added 0.17 ml (1.68 mmol) of piperidine. The reaction mixture was stirred at room temperature for 3 hours and concentrated at rotavapor under reduced pressure.

Excess reagents and side products were then removed by adding $CH_2Cl_2$, while the biotinylated amine precipitated out. It was then collected by filtering through a sintered funnel and vacuum dried.

To the amine thus obtained, was added 0.13 g (1.28 mmol) of succinic anhydride in 5 ml of DMF and the reaction mixture was stirred at room temperature for 5 hours. It was then concentrated and the product 5 was precipitated by $CH_2Cl_2$ to afford 0.48 g (82%) of the pure (HPLC pure) product.

Synthesis of the Succinimidyl Ester 6:

To a stirred solution of 95 mg (0.14 mmol) of 5, 22 μL (0.14 mmol) of diisopropylcarbodiimide and 20 mg (0.14 mmol) of HOBt in 2 ml of anhydrous DMF, was added 16 mg (0.14 mmol) of N-hydroxysuccinimide in 0.5 ml of DMF. The pH of the reaction mixture was brought up to between 8 and 9 and it was stirred overnight at room temperature. Concentration at reduced pressure and HPLC purification using a preparative column afforded 90 mg (84%) of 6 in pure form.

This novel photocleavable biotin is useful, e.g., for labeling siRNA as described herein.

D. Use of an siRNA Derivative for Affinity Purification of RNAi Components

An siRNA derivative can be used to affinity purify proteins involved in RNAi and to determine characteristics of molecules that participate in RNAi. An siRNA derivative can be used for affinity purification of RNAi proteins from various organisms, e.g., worms (such as *Caenorhabditis elegans*), insects (such as *Drosophila melanogaster*), and mammals (e.g., mice, rats, domestic animals, and humans). For example, an siRNA derivative that has been modified by the addition of a molecule at a 3' terminus that can be used for crosslinking the siRNA derivative to a solid substrate is useful for, e.g., recovering an siRNA containing such a modification from a cell (see the biotin pull out assay in Examples 1 and 5) or for isolating components of the RNAi machinery such as RISC that bind to the siRNA derivative. Such molecules provide insight into the mechanism of RNAi in mammalian cells and additional targets for compounds that inhibit or enhance RNAi activity. Methods for attaching a compound to a substrate for use in purification methods and methods for affinity purification of proteins are known in the art.

III. Efficacy Assays

The invention further features assaying compounds of the invention that have been altered in at least one of the features described herein whose efficacy for modulating expression of a target RNA is not established. In one embodiment, the invention features methods of assaying the ability of a compound of the invention (e.g., a siRNA, candidate RNAi derivative, modified siRNA, etc.) to modulate (e.g., inhibit) expression of a target RNA using a dual fluorescence system. Other assay systems known in the art that measure the efficacy of an siRNA can be used to evaluate whether a modified siRNA is an siRNA derivative. In general, the ability of an siRNA derivative to inhibit detectable expression of a target RNA is at least 10%, 20%, or 30% compared to expression of the target in the absence of the RNAi derivative. In some cases, expression of the target sequence is inhibited 50%, 75%, 85%, 90%, or 100%.

A compound of the invention (e.g., a siRNA, candidate RNAi derivative, modified siRNA, etc.) can be tested for its ability to inhibit expression of a targeted gene. For example, candidate RNAi derivatives that can inhibit such expression are identified as siRNA derivatives. Any system in which RNAi activity can be detected can be used to test the activity of a compound of the invention (e.g., a siRNA, candidate RNAi derivative, modified siRNA, etc.). In general, a system in which RNAi activity can be detected is incubated in the presence and absence of a compound of the invention (e.g., a siRNA, candidate RNAi derivative, modified siRNA, etc.

The invention includes a dual fluorescence reporter gene assay (DFRG assay) that can be used to test a compound of the invention (e.g., a siRNA, candidate RNAi derivative, modified siRNA, etc.). The DFRG assay can also be used, for example, to test the ability of these and other types of compounds to inhibit expression of a targeted gene (i.e., RNAi inhibitors).

In the DFRG assay, cells are used that have RNAi activity and contain at least two reporter genes that encode and can express at least two different fluorescent proteins. Alternatively, at least one of the reporter genes can encode hybrid proteins comprising a portion that corresponds to a reporter protein and a portion that corresponds to a protein of interest (i.e., is translated from an mRNA that is targeted by the siRNA or modified siRNA used in the assay). The fluorescence emission spectra of the two proteins are such that they can be distinguished when expressed simultaneously, e.g., red fluorescent protein (RFP) and green fluorescent protein (GFP). One reporter gene is used as a reference. The reporter cell is transfected with a compound of the invention (e.g., a siRNA, candidate RNAi derivative, modified siRNA, etc.), for example, an siRNA that has been chemically modified at 3' terminus, contains at least one crosslink between the two strands of the siRNA, or both. The compound of the invention (e.g., a siRNA, candidate RNAi derivative, modified siRNA, etc.) is targeted to one of the reporter gene sequences. In some cases, the cell is co-transfected with the reporter genes and the compound of the invention (e.g., a siRNA, candidate RNAi derivative, modified siRNA, etc.). The cell is incubated for a time sufficient to produce detectable reporter proteins in the absence of the compound of the invention (e.g., a siRNA, candidate RNAi derivative, modified siRNA, etc.). After incubation, the level of fluorescence is measured using methods known in the art. Generally, after incubation, the cell is lysed and the lysate is cleared and protein concentration determined. An aliquot of the lysate is then assayed for fluorescence intensity.

The ratio of fluorescence emission intensities between the two reporter genes is compared to a control to standardize the ratio. Normalized ratios of less than one (i.e., less fluorophore expression in the cell contacted with the compound of the invention (e.g., a siRNA, candidate RNAi derivative, modified siRNA, etc.) than in the control cell) indicate target sequence-specific interference.

In one embodiment, the invention includes a method of determining whether a candidate siRNA derivative is an siRNA derivative. The method includes the steps of obtaining a reporter cell comprising two different fluorescent reporter genes, transfecting the reporter cell with a candidate siRNA derivative targeted to one of the fluorescent reporter genes, thus creating a test cell; incubating the test cell for a time sufficient for a reporter cell to express detectable levels of the fluorescent reporter proteins encoded by the fluorescent reporter genes; determining the fluorescence intensity of each fluorescent reporter protein in the test cell; and determining the ratio of the level of fluorescence intensity between the two fluorescent reporter proteins in the test cell and normalizing the ratio to the ratio of fluorescence intensity in a control reporter cell that was not transfected with the candidate siRNA derivative, such that a normalized ratio of less than one indicates that the candidate siRNA derivative is an siRNA derivative. In some embodiments of this method, the control reporter cell is transfected with an antisense sequence that is complementary to the targeted reporter gene. In some embodiments, the candidate siRNA derivative is a crosslinked siRNA (e.g., the modified siRNA contains a single crosslink), the candidate siRNA derivative is psoralen crosslinked, the candidate siRNA derivative is modified at a 3' terminus (e.g., the modified siRNA comprises a biotin at a 3' terminus), or the modified siRNA contains a photocleavable biotin having the structure depicted in FIG. 20 at a 3' terminus. The candidate siRNA derivative can contain a peptide (e.g., a Tat peptide), nanoparticle, peptidomimetic, organic molecule (e.g., a fluorescent dye) or dendrimer at a 3' terminus. In some cases, the two reporter proteins are Green Fluorescent Protein (GFP) and Red Fluorescent Protein (RFP). In some cases, the normalized ratio is at least 0.3.

The control ratio used for normalization is determined by transfecting a cell with the two reporter genes, incubating, and determining the ratio of fluorescence intensities from the two cells as described above for a test cell. In some embodiments, the control cell is transfected with the reporter genes and with an antisense RNA that is specific for the reporter gene that is targeted by the compound of the invention (e.g., a siRNA, candidate RNAi derivative, modified siRNA, etc.). Methods of designing and selecting siRNAs are known in the art. In some cases, the targeted region in the mRNA and the sequence in the siRNA duplex are chosen using the following guidelines. The targeted sequence is generally selected from the open reading frame region from the cDNA sequence of the targeted gene. In general the target site is at least 75-100 nucleotides downstream from the start codon. Neither the 5' nor 3' untranslated regions and regions near the start codon are generally used for targeting because these may be richer in regulatory protein binding sites. After locating the first AA dimer located about 100 bases downstream from the start codon, the next 19 nucleotides following the AA dimer are recorded The percentage of guanosines and cytidines (G/C content) of the AA-N19-21 base sequence is determined. The G/C content of this short sequence must be less than 70% and greater than 30% for use as siRNA. In general, the G/C content of the sequence is about 50%. If the selected sequence does not meet these criteria, the search continues downstream to the next AA dimer until the G/C conditions are met. To ensure that only one gene is targeted by the sequence, the selected sequence (generally about 21 nucleotides) is subjected to a BLAST search (NCBI database) against EST libraries.

In some embodiments of the invention, proteins from the lysates are prepared as described above and analyzed using Western blotting. Briefly, the proteins prepared from the transfected cells (control cells and test cells) are subjected to SDS-PAGE (e.g., in a 10% gel) and transferred to a membrane suitable for Western blotting (for example, a PVDF membrane). The membrane is immunoblotted using methods known in the art to detect the fluorescent reporter proteins. In general, a protein that can be used as a control for protein loading (such as a housekeeping protein) is also detected. Less expression of the targeted protein compared to control indicates that the test sequence (e.g. modified siRNA) is effective for target sequence-specific interference.

Cells to be used in a DFRG assay are generally cultured mammalian cells, e.g., human cells. The cells can be immortal, primary, or secondary cells. Cells from other organisms that exhibit RNAi or RNAi-type activity such as quelling can also be used. Such cells include those from fungi, plants, invertebrates (e.g., Drosophila melanogaster and Caenorhabditis elegans), and vertebrates (e.g., zebrafish and mouse). Fluorescent molecules that can be used in DFRG assays are pairs of fluorescent molecules whose emission spectra can be distinguished when there is simultaneous emission. Examples of such pairs include Green Fluorescent Protein (GFP) and Red Fluorescent Protein (RFP). Additional examples can be selected, e.g., from those shown in Table 1.

TABLE I

LIVING COLORS FLUORESCENT PROTEINS

| Fluor. Protein | Excit./Emiss. Maxima (nm) | Extinction Coefficient | Quantum Yield | Reference |
|---|---|---|---|---|
| DsRed | 558/583 | 22,600 | 0.23 | Matz et al., 1999 |
| EGFP | 488/507 | 56,000 | 0.60 | D. W. Piston, |
| EYFP | 513/527 | 84,000 | 0.61 | Vanderbilt |
| ECFP | 433/475 | 28,000 | 0.40 | University, |
| EBFP | 380/440 | 31,000 | 0.18 | Personal comm. |

IV. Production

RNA may be produced enzymatically or by partial/total organic synthesis, any modified ribonucleotide can be introduced by in vitro enzymatic or organic synthesis. In one embodiment, a siRNA is prepared chemically. Methods of synthesizing RNA molecules are known in the art, in particular, the chemical synthesis methods as de scribed in Verma and Eckstein (1998) *Annul Rev. Biochem.* 67:99-134. In another embodiment, a siRNA is prepared enzymatically. For example, a ds-siRNA can be prepared by enzymatic processing of a long ds RNA having sufficient complementarity to the desired target mRNA. Processing of long ds RNA can be accomplished in vitro, for example, using appropriate cellular lysates and ds-siRNAs can be subsequently purified by gel electrophoresis or gel filtration. ds-siRNA can then be denatured according to art-recognized methodologies. In an exemplary embodiment, RNA can be purified from a mixture by extraction with a solvent or resin, precipitation, electrophoresis, chromatography, or a combination thereof. Alternatively, the RNA may be used with no or a minimum of purification to avoid losses due to sample processing. Alternatively, the single-stranded RNAs can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) *Methods Enzymol.* 180:51-62). The RNA may be dried for storage or dissolved in an aqueous solution. The solution may contain buffers or salts to inhibit annealing, and/or promote stabilization of the single strands.

In one embodiment, siRNAs are synthesized either in vivo, in situ, or in vitro. Endogenous RNA polymerase of the cell may mediate transcription in vivo or in situ, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the siRNA. Inhibition may be targeted by specific transcription in an organ, tissue, or cell type; stimulation of an environmental condition (e.g., infection, stress, temperature, chemical inducers); and/or engineering transcription at a developmental stage or age. A transgenic organism that expresses siRNA from a recombinant construct may be produced by introducing the construct into a zygote, an embryonic stem cell, or another multipotent cell derived from the appropriate organism.

V. Targets

In one embodiment, the target mRNA of the invention specifies the amino acid sequence of a cellular protein (e.g., a nuclear, cytoplasmic, transmembrane, or membrane-associated protein). In another embodiment, the target mRNA of the invention specifies the amino acid sequence of an extracellular protein (e.g., an extracellular matrix protein or secreted protein). As used herein, the phrase "specifies the amino acid sequence" of a protein means that the mRNA sequence is translated into the amino acid sequence according to the rules of the genetic code. The following classes of proteins are listed for illustrative purposes: developmental proteins (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogene-encoded proteins (e.g., ABLI, BCLI, BCL2, BCL6, CBFA2, CBL, CSFIR, ERBA, ERBB, EBRB2, ETSI, ETSI, ETV6, FGR, FOS, FYN, HCR, HRAS, JUN, KRAS, LCK, LYN, MDM2, MLL, MYB, MYC, MYCLI, MYCN, NRAS, PIM I, PML, RET, SRC, TALI, TCL3, and YES); tumor suppressor proteins (e.g., APC, BRCA1, BRCA2, MADH4, MCC, NF I, NF2, RB I, TP53, and WTI); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextriinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases).

In a preferred aspect of the invention, the target mRNA molecule of the invention specifies the amino acid sequence of a protein associated with a pathological condition. For example, the protein may be a pathogen-associated protein (e.g., a viral protein involved in immunosuppression of the host, replication of the pathogen, transmission of the pathogen, or maintenance of the infection), or a host protein which facilitates entry of the pathogen into the host, drug metabolism by the pathogen or host, replication or integration of the pathogen's genome, establishment or spread of infection in the host, or assembly of the next generation of pathogen. Alternatively, the protein may be a tumor-associated protein or an autoimmune disease-associated protein.

In one embodiment, the target mRNA molecule of the invention specifies the amino acid sequence of an endogenous protein (i.e., a protein present in the genome of a cell or organism). In another embodiment, the target mRNA molecule of the invention specified the amino acid sequence of a heterologous protein expressed in a recombinant cell or a genetically altered organism. In another embodiment, the target mRNA molecule of the invention specified the amino acid sequence of a protein encoded by a transgene (i.e., a gene construct inserted at an ectopic site in the genome of the cell). In yet another embodiment, the target mRNA molecule of the invention specifies the amino acid sequence of a protein encoded by a pathogen genome which is capable of infecting a cell or an organism from which the cell is derived.

By inhibiting the expression of such proteins, valuable information regarding the function of said proteins and therapeutic benefits which may be obtained from said inhibition may be obtained.

VI. Targeting Transcription Elongation Factors

Positive transcription elongation factor complex b (P-TEFb), which is composed of two subunits, CDK9 and cyclin T1 (CycT1) (Garber et al., Genes & Dev., 12:3512-3527 (1998)), allows the transition to productive elongation, producing longer mRNA transcripts (Price (2000), supra). Two negative transcription elongation factors, DSIF (DRB sensitivity-inducing factor; DRB is 5,6-dichloro-1-β-D-ribofuranosylbenzimidazole) and NELF (negative elongation factor), have been identified and characterized (Wada et al., Genes Dev. 12:343-56 (1998); Yamaguchi et al., *Cell* 97:41-51 (1999)). DSIF is composed of at least two subunits, one 14-kDa and one 160-kDa, which are homologs of the *Saccharomyces cerevisiae* transcription factors Spt5 and Spt4, respectively (Hartzog et al., Genes Dev. 12:357-369 (1998)). NELF is composed of five polypeptides, named as NELF-A to -E, and contains a subunit identical to RD, a putatitive RNA-binding protein (containing arginine-aspartic acid (RD) dipeptide repeats) of unknown function. DSIF and NELF function cooperatively and strongly repress RNA pol II elongation (Yamaguchi et al., supra). In the absence of P-TEFb, DSIF plays the role of a negative regulator in transcription (Wada et al., EMBO J. 17:7395-7403 (1998)). DSIF subunit Spt5 also has a positive elongation activity in Tat transactivation (Wu-Baer et al., J. Mol. Biol. 277:179-197 (1998); Kim et al., Mol. Cell. Biol. 19:5960-598 (1999)). Another transcription elongation factor, Spt6, has been identified which is functionally related to Spt5; Spt5 and Spt6 have been shown to colocalize at regions of active transcription as well as at certain stress response genes induced by heat shock (Kaplan et al., Genes Dev. 14:2623-2634 (2000); Andrulis et al., Genes Dev. 14: 2635-2649 (2000)).

Among the genes regulated in this manner are several protooncogenes (c-myc, c-myb, c-fos); c-fms, the gene encoding macrophage colony stimulating factor 1 (CSF-1) receptor; the gene encoding adenosine deaminase; a collection of stress response genes including hsp70; and genes involved in replication and pathogenesis of HIV-1 and HIV-2.

One elegant example of transcription elongation control is the mechanism of HIV-1 gene expression (reviewed in: Cullen 1998 Cell 93:685-92; Emerman and Malin 1998 *Science* 280:1880-4; Jeang et al. 1999 *J Biol Chem* 274: 28837-40; Jones 1997 *Genes Dev* 11:2593-2599; Karm 1999 *J Mol Biol.* 293:235-254; Taube et al. 1999 Virology 264: 245-253). The HIV-1 transcriptional activation mechanism requires Tat interactions with the human Cyclin T1 (hCycT1) subunit of P-TEFb that recruits the kinase complex to the pol II elongation machinery (Bieniasz et al. 1998 *EMBO J.* 17:7056-65; Herrmann and Rice 1995 *J. Virol.* 69:1612-1620; Herrmann and Rice 1993 Virology 197:601-608; Isel and Karn 1999 *J. Mol Biol.* 290:929-941; Jones 1997 *Genes Dev.* 11:2593-2599; Mancebo et al. 1997 *Genes Dev* 11:2633-2644; Taube et al. 1999 Virology 264: 245-253; Wei et al. 1998 Cell 92:451-62; Yang et al. 1997 *Proc Natl Acad Sci USA* 94:12331-12336; Zhu et al. 1997 *Genes Dev.* 11:2622-32). The pol II CTD, and Spt5 are also intimately connected to this regulation of HIV gene expression by Tat and P-TEFb. During HIV transcription, P-TEFb, which is initially found as a component of the pol II preinitiation complex (PIC), travels with the transcription elongation complex (TEC) as it moves along the HIV transcription unit (Ping and Rana 1999 *J Biol Chem* 274: 7399-7404). In contrast, DSIF and NELF are not present in the PIC, but associate with the TEC at promoter proximal positions and then travel with the TECs down the template (Ping and Rana 2001 *J Biol Chem* 276:12951-12958).

Based, at least in part, on the findings presented in Examples XX-XXXIII, the present invention relates to methods of modulating (e.g., decreasing) the activity of transcription elongation factors (TEFs) and more specifically to ribonucleic acid interference (RNAi) of TEFs (e.g., positive transcription elongation factors or P-TEFs) or subunits thereof (e.g., the P-TEFb subunits CDK9 and CycT1).

In one embodiment, RNA interference (RNAi) methods (e.g., featuring siRNAs, siRNA derivative, a modified siRNA, etc., as described herein) are used to specifically silence one or more TEFs, e.g., P-TEFb, DSIF and/or Spt6. These RNAi methods can be used to reduce HIV infectivity and to regulate genes involved in cell proliferation and differentiation, e.g., genes that have been correlated with diseases and disorders characterized by unwanted or aberrant cellular proliferation or differentiation, such as cancer. In one embodiment, the unwanted cellular proliferation is cancer, for instance, carcinomas, sarcomas, metastatic disorders, and hematopoietic neoplastic disorders.

In one embodiment, the target region of the mRNA sequence is located from 100 to 300 nucleotides downstream (3') of the start of translation of the TEF mRNA. In another embodiment, the target region of the mRNA sequence is located in a 5' untranslated region (UTR) or a 3' UTR of the mRNA of a TEF, e.g., CDK9, CycT1, Spt4, Spt5, or Spt6.

In another aspect, the invention features methods of treating a subject having a disorder characterized by unwanted cellular proliferation, e.g., cancer, e.g., carcinomas, sarcomas, metastatic disorders and hematopoietic neoplastic disorders (e.g., leukemias), or proliferative skin disorders, e.g., psoriasis, by administering to the subject an amount of a nucleic acid composition, e.g., a therapeutic composition, of the invention, effective to inhibit TEF activity. As used herein, inhibiting P-TEF activity refers to a reduction in the activity of TEF, e.g., by 10%, 20%, 30%, 40%, 50%, 60%, 70%, 80%, 90%, or 100%.

In another aspect, the invention provides a method of treating a subject infected with HIV by administering to the subject an amount of the nucleic acid compositions, e.g., the therapeutic compositions, of the invention, effective to inhibit TEF expression or activity. In another aspect, the invention features a method of treating a subject having a disorder characterized by aberrant or unwanted expression of a gene whose expression is regulated by a TEF, e.g., CDK9, CycT1, Spt4, Spt5 and/or Spt6, by administering to the subject an amount of the nucleic acid compositions, e.g., the therapeutic compositions, of the invention, effective to inhibit TEF expression or activity.

In another aspect, the invention features a method of treating a subject having a disorder characterized by aberrant or unwanted expression or activity of a TEF, e.g., CDK9, CycT1, Spt4, Spt5 and/or Spt6 by administering to the subject an amount of the nucleic acid compositions, e.g., the therapeutic compositions, of the invention, effective to inhibit TEF expression or activity. In one embodiment, the disorder is HIV/AIDS. In another embodiment, the disorder is cancer, e.g., carcinomas, sarcomas, metastatic disorders and hematopoietic neoplastic disorders, e.g., leukemia.

1. TEF Nucleic Acid Targets

In one aspect, the invention features compositions (e.g., siRNAs, siRNA derivatives, modified siRNAs, etc.) that are targeted to a CDK9, CycT1, Spt4, Spt5, or Spt6 RNA.

The mRNA sequence of CDK9 can be any ortholog of CDK9, such as sequences substantially identical to the *S. cerevisiae*, human, *C. elegans, D. melanogaster*, or mouse CDK9, including but not limited to GenBank Accession Nos. NM_001261 (GI:17017983) (SEQ ID NO:2) (corresponding protein sequence: NP_001252) (human); P50750 (human); NP_570930 (mouse); BA C40824 (mouse); NP_477226 (fruit fly); NP_492906 (*C. elegans*); or NP_492907 (*C. elegans*). The mRNA sequence of CycT1 can be any ortholog of CycT1, such as sequences substantially identical to the *S. cerevisiae*, human, or mouse CycT1, including but not limited to GenBank Accession Nos. AF048730 (GI:2981195) (corresponding protein sequence: AAC39664) (human); NM_001240 (GI:17978465) (corresponding protein sequence: NP_001231) (human); AAN73282 (chimpanzee); NP_033963 (mouse); AAD17205 (mouse); QDQWV9 (mouse); AAM74155 (goat); or AAM74156 (goat).

The mRNA sequence of Spt4 can be any ortholog of Spt4, such as sequences substantially identical to the *S. cerevisiae*, human, or mouse Spt4, including but not limited to GenBank Accession Nos. NM_003168 (GI:4507310) (human Spt4); U38817 (GI:1401054) (humanSpt4); U38818 (GI:1401052) (human Spt4); U43923 (GI:1297309)(human Spt4); NM_009296 (GI:6678180) (mouse Spt4); U43154 (GI:1401065) (mouse Spt4) or M83672 (*S. cerevisiae* Spt4). The mRNA sequence of Spt5 can be any ortholog of Spt5, such as sequences substantially identical to the *S. cerevisiae*, human, or mouse Spt5, including but not limited to GenBank Accession Nos. BCO2403 (GI: 18848307) (human Spt5), NM 003169 (GI:20149523) (human Spt5); AB000516 (GI:2723379) (human Spt5); AF 040253 (GI: 4104823) (human Spt5); U56402 (GI:1845266) (human Spt5); NM013676 (GI:22094122) (mouse Spt5); U888539 (mouse Spt5); or M 62882 (*S. cerevisiae* Spt5). The mRNA sequence of Spt6 can be any ortholog of Spt6, such as sequences substantially identical to the *S. cerevisiae* or mouse Spt6, including but not limited to NM_009297 (GI: 6678182) (mouse Spt6) or M34391 (*S. cerevisiae* Spt6).

2. siRNA Molecules

The compositions (e.g., siRNAs, siRNA derivatives, modified siRNAs, etc.) of the invention include dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA of CDK9, CycT1, Spt4, Spt5, or Spt6, and the other strand is identical or substantially identical to the first strand. The compositions of the invention can be chemically synthesized, or can be transcribed in vitro from a DNA template, or in vivo from, e.g., shRNA. The dsRNA molecules can be designed using any method known in the art, for instance, by using the following protocol:

A. Beginning with the AUG start codon, look for AA dinucleotide sequences; each AA and the 3' adjacent 16 or more nucleotides are potential siRNA targets (see FIGS. 15, 16, 34, 35, 36). siRNAs taken from the 5' untranslated regions (UTRs) and regions near the start codon (within about 75 bases or so) may be less useful as they may be richer in regulatory protein binding sites, and UTR-binding proteins and/or translation initiation complexes may interfere with binding of the siRNP or RISC endonuclease complex. Thus, in one embodiment, the nucleic acid molecules are selected from a region of the cDNA sequence beginning 50 to 100 nt downstream of the start codon. Further, siRNAs with lower G/C content (35-55%) may be more active than those with G/C content higher than 55%. Thus in one embodiment, the invention includes nucleic acid molecules having 35-55% G/C content. In addition, the strands of the siRNA can be paired in such a way as to have a 3' overhang of 1 to 4, e.g., 2, nucleotides. Thus in another embodiment, the nucleic acid molecules can have a 3' overhang of 2 nucleotides, such as TT. The overhanging nucleotides can be either RNA or DNA.

B. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at the National Center for Biotechnology Information web site of the National Institutes of Health.

C. Select one or more sequences that meet your criteria for evaluation.

Further general information about the design and use of siRNA can be found in "The siRNA User Guide," available at the web site of the laboratory of Dr. Thomas Tuschl at Rockefeller University.

Negative control siRNAs should have the same nucleotide composition as the selected siRNA, but without significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

The nucleic acid compositions of the invention include both unmodified TEF siRNAs and modified TEF siRNAs as known in the art, such as crosslinked siRNA derivatives as described in U.S. Provisional Patent Application 60/413,529, which is incorporated herein by reference in its entirety. Crosslinking can be employed to alter the pharmacokinetics of the composition, for example, to increase half-life in the body. Thus, the invention includes siRNA derivatives that include siRNA having two complementary strands of nucleic acid, such that the two strands are crosslinked. For example, a 3' OH terminus of one of the strands can be modified, or the two strands can be crosslinked and modified at the 3'OH terminus. The siRNA derivative can contain a single crosslink (e.g., a psoralen crosslink). In some embodiments, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying SiRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The nucleic acid compositions of the invention can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles; and Godard et al., Eur. J. Biochem. 232(2):404-10 (1995) (describes nucleic acids linked to nanoparticles).

The nucleic acid molecules of the present invention can also be labeled using any method known in the art; for instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^3$H, $^{32}$P, or other appropriate isotope. The dsRNA molecules of the present invention can comprise the following sequences as one of their strands, and the corresponding sequences of allelic variants thereof:

```
hCycT1 ds
                                        (SEQ ID NO: 25)
5'-UCCCUUCCUGAUACUAGAAdTdT-3'

HcycT1 mm (neg. ctrl)
                                        (SEQ ID NO: 26)
5'-UCCCUUCCGUAUACUAGAAdTdT-3'

CDK9 ds
                                        (SEQ ID NO: 27)
5'-CCAAAGCUUCCCCCUAUAAdTdT-3'

CDK9 mm (neg. ctrl)
                                        (SEQ ID NO: 28)
5'-CCAAAGCUCUCCCCUAUAAdTdT-3'

Spt5 ds
                                        (SEQ ID NO: 29)
5'- AACTGGGCGAGTATTACATGAdTdT-3'

Spt5 mm (neg. ctrl)
                                        (SEQ ID NO: 30)
5'- AACTGGGCGGATATTACATGAdTdT-3'
```

The above sequences (e.g., sense sequences) correspond to targeted portions of their target mRNAs, as described herein. Reverse complementary sequences (e.g., antisense sequences) can be generated according to to art recognized principles. dsRNA molecules of the present invention preferably comprise one sense sequence or strand and one respective antisense sequence or strand.

Moreover, because RNAi is believed to progress via at least one single stranded RNA intermediate, the skilled artisan will appreciate that ss-siRNAs (e.g., the antisense strand of a ds-siRNA) can also be designed as described herein and utilized according to the claimed methodologies.

3. Methods of Treatment

The present invention provides for both prophylactic and therapeutic methods of treating a subject at risk of (or susceptible to) a disorder or having a disorder associated with aberrant or unwanted TEF expression or activity, e.g., CDK9, CycT1, Spt4, Spt5, or Spt6 activity. As used herein, the term "treatment" is defined as the application or administration of the siRNA compositions of the present invention to an individual, e.g., a patient or subject, or application or administration of a therapeutic composition including the siRNA compositions to an isolated tissue or cell line from an individual who has a disease, a symptom of a disease, or a predisposition toward a disease, with the purpose to cure, heal, alleviate, relieve, alter, remedy, ameliorate, improve, or affect the disease, the symptoms of disease, or the predisposition toward disease. The treatment can include administering siRNAs to one or more target sites on one or both of the P-TEFb subunits, e.g., CDK9 or CycT1, to one or more target sites on one or both of the DSIF subunits, e.g., Spt5 or Spt4, or to target sites on Spt6, as well as siRNAs to other TEFs. The mixture of different siRNAs can be administered together or sequentially, and the mixture can be varied over time.

With regards to both prophylactic and therapeutic methods of treatment, such treatments can be specifically tailored or modified, based on knowledge obtained from the field of genomics, particularly genomics technologies such as gene sequencing, statistical genetics, and gene expression analysis, as applied to a patient's genes. Thus, another aspect of the invention provides methods for tailoring an individual's prophylactic or therapeutic treatment with the siRNA compositions of the present invention according to that individual's genotype; e.g., by determining the exact sequence of the patient's CDK9, CycT1, Spt4, Spt5, and/or Spt6, and designing, using the present methods, an siRNA molecule customized for that patient. This allows a clinician or physician to tailor prophylactic or therapeutic treatments to patients to enhance the effectiveness or efficacy of the present methods. Also with regards to both prophylactic and therapeutic methods of treatment, such treatments can be specifically tailored or modified, based on knowledge obtained from the field of pharmacogenomics. In one aspect, the invention provides a method for treating a subject having a disease, disorder, or condition associated with an aberrant or unwanted TEF expression or activity, e.g. CDK9, CycT1, Spt4, Spt5, or Spt6 expression or activity, by administering to the subject a composition including a CDK9, CycT1, Spt4, Spt5, and/or Spt6 siRNA. Subjects having a disease which is caused or contributed to by aberrant or unwanted CDK9, CycT1, Spt4, Spt5, or Spt6 expression or activity can be identified by, for example, any or a combination of diagnostic or prognostic assays known in the art or as described herein. Administration of a composition including a CDK9, CycT1, Spt4, Spt5, or Spt6 siRNA can occur prior to the manifestation of symptoms characteristic of the CDK9, CycT1, Spt4, Spt5, or Spt6 aberrance, such that the disease, disorder, or condition is treated or inhibited.

In one aspect, the invention provides a method for preventing in a subject, a disease or condition associated with an aberrant or unwanted CDK9, CycT1, Spt4, Spt5, or Spt6 expression or activity, by administering to the subject a composition including a CDK9, CycT1, Spt4, Spt5, or Spt6 siRNA. Subjects at risk for a disorder caused or contributed to by aberrant or unwanted CDK9, CycT1, Spt4, Spt5, or Spt6 expression or activity can be identified by, for example, any or a combination of diagnostic or prognostic assays known in the art or as described herein. Administration of a prophylactic agent can occur prior to the manifestation of symptoms characteristic of the CDK9, CycT1, Spt4, Spt5, or Spt6 aberrance, such that a disease or disorder is prevented or, alternatively, delayed in its progression.

Additionally, TEF molecules, e.g. CDK9, CycT1, Spt4, Spt5, and/or Spt6 may play an important role in the etiology of certain viral diseases, including, but not limited to, Human Immunodeficiency Virus (HIV), Hepatitis B, Hepatitis C, and Herpes Simplex Virus (HSV). P-TEFb siRNA compositions can be used to treat viral diseases, and in the treatment of viral infected tissue or virus-associated tissue fibrosis. In particular, as described herein, TEF, e.g. CDK9, CycT1, Spt4, Spt5, and/or Spt6, siRNA compositions can be used to treat HIV infections. Also, TEF modulators can be used in the treatment and/or diagnosis of virus-associated carcinoma, including hepatocellular cancer.

4. Treating HIV Infection

Figure 11:
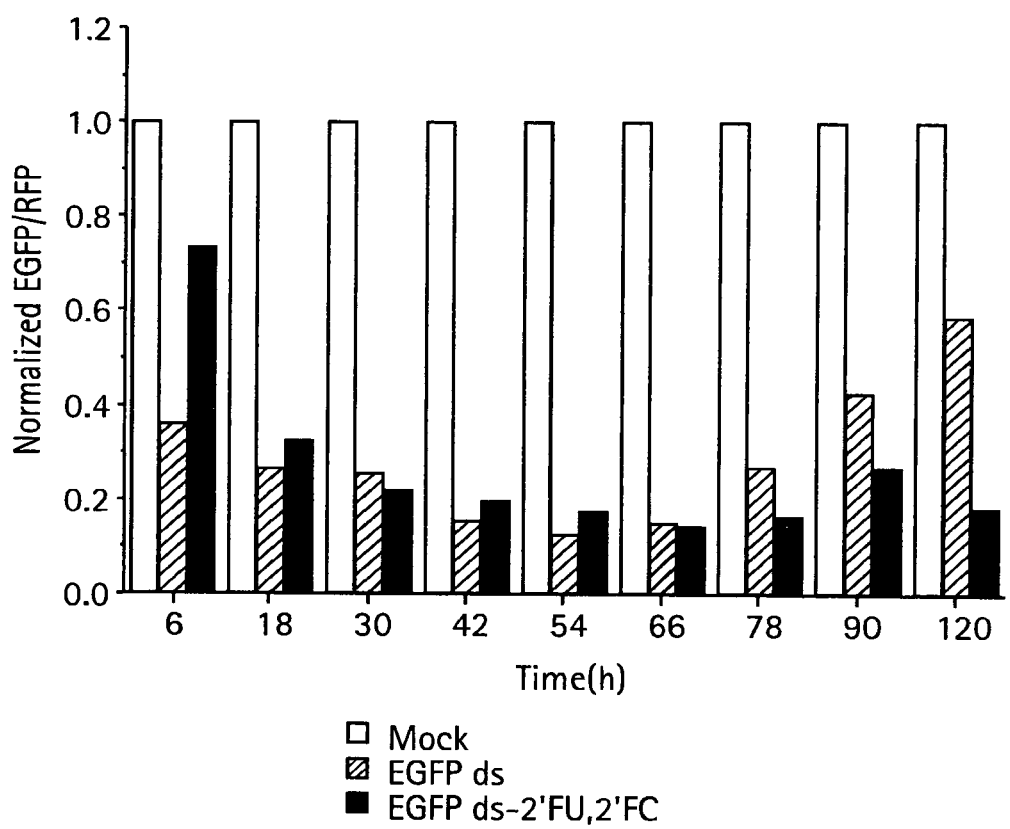
FIG. 11 depicts the kinetics of RNAi effects of duplex siRNA with 2'-Fluoro uridine and cytidine modification in HeLa cells.

In one aspect, the present invention is based on the discovery that specific reduction of TEF activity, e.g., CDK9, CycT1, Spt4, Spt5 or Spt6 activity, in human cells is non-lethal and can be used to control, e.g., inhibit, Tat transactivation and HIV replication in host cells. While not wishing to be bound by theory, one model for understanding HIV-1 gene regulation is depicted in FIG. 1A and FIG. 11. Briefly, RNA pol II containing nonphosphorylated C-terminal domain (CTD) of the largest subunit (IIA) assembles on the HIV LTR promoter to form a preinitiation complex. TFIIH binds to nonphosphorylated RNA pol II and plays a critical role in transcription initiation and promoter clearance. TFIIH phosphorylates the CTD of the largest subunit of RNA pol II and assists in promoter clearance. The TFIIH complex dissociates from TECs 30 to 50 nucleotides after initiation and is not part of the elongation complexes. P-TEFb, composed of CDK9 and cyclin T1, is a component of PICs, however, it may not be an active kinase at this stage. After promoter clearance, DSIF and NELF associate with the transcription complex during the early elongation complex. Under standard physiological conditions and in the case of non-HIV-1 LTR promoters, Spt5 is phosphorylated by CDK9 once DSIF/NELF associate with the early elongation complex, and this phosphorylation of Spt5 may sufficiently support regular transcription elongation. In the presence of DRB, the kinase activity of CDK9 is inhibited and Spt5 cannot be phosphorylated by P-TEFb. The unphosphorylated form of Spt5 acts as a negative regulator and causes inhibition of RNA pol II elongation. In contrast to cellular promoters, transcription from the HIV-1 LTR promoter is not efficient and CDK9 is activated by Tat protein. In the absence of Tat, elongation complexes which originated at the HIV-1 promoter meet DSIF and NELF, CDK9 is unable to efficiently phosphorylate Spt5 and, as a result, elongation is not processive. After the transcription of a functional TAR RNA structure, Tat binds to TAR and repositions P-TEFb in the vicinity of the CTD of RNA pol II and Spt5. Hyperphosphorylation of the CTD is carried out by P-TEFb after the formation of Tat-TAR-P-TEFb complexes. In addition to CTD phosphorylation, Tat also enhances the phosphorylation of Spt5 mediated by P-TEFb, and the phosphorylated form of Spt5 turns DSIF into a positive regulator of transcription elongation (Ping and Rana, *J. Biol. Chem.*, 276: 12951-12958 (2001)). Specific reduction in P-TEFb or DSIF activity can be achieved in a number of different ways, including RNAi, antisense, ribozymes, or small molecules targeted to one or both subunits of P-TEFb (e.g., CDK9 or CycT1) or DSIF (e.g., Spt4 or Spt5). Specific reduction in Spt6 activity can be achieved in a number of different ways, including RNAi, antisense, ribozymes, or small molecules targeted to Spt6.

5. Treating Cancer

In another aspect, the present invention is based in part on the discovery that specific reduction of transcription elongation factor activity in human cells is non-lethal and can be used to regulate the expression of genes correlated with diseases or disorders characterized by unwanted or aberrant cellular proliferation or differentiation, to decrease the growth of cancerous cells, and reduce the metastatic activity of cancerous cells. Examples of proliferative and/or differentiative disorders include cancer, e.g., carcinomas, sarcomas, metastatic disorders or hematopoietic neoplastic disorders, e.g., leukemias, as well as proliferative skin disorders, e.g., psoriasis or hyperkeratosis. Other myeloproliferative disorders include polycythemia vera, myelofibrosis, chronic myelogenous (myelocytic) leukemia, and primary thrombocythaemia, as well as acute leukemia, especially erythroleukemia, and paroxysmal nocturnal haemoglobinuria. Metastatic tumors can arise from a multitude of primary tumor types, including but not limited to those of prostate, colon, lung, breast and liver origin. Specific reduction in transcription elongation factors such as P-TEFb (CDK9/CycT1), DSIF (Spt4/Spt5) or Spt6, can be achieved in a number of different ways, including the introduction into a cell of RNAi, antisense, ribozyme, dominant negative mutation or sequences containing such mutation, or small molecules targeted to the factor, e.g., one or both subunits of P-TEFb (CDK9/CycT1), one or both subunits of DSIF (e.g., Spt5 or Spt4) or Spt6.

VII. Methods of Introducing RNAs, Vectors, and Host Cells

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell with the target gene may be derived from or contained in any organism. The organism may a plant, animal, protozoan, bacterium, virus, or fungus. The plant may be a monocot, dicot or gymnosperm; the animal may be a vertebrate or invertebrate. Preferred microbes are those used in agriculture or by industry, and those that are pathogenic for plants or animals. Fungi include organisms in both the mold and yeast morphologies. Plants include *arabidopsis*; field crops (e.g., alfalfa, barley, bean, corn, cotton, flax, pea, rape, nice, rye, safflower, sorghum, soybean, sunflower, tobacco, and wheat); vegetable crops (e.g., asparagus, beet, broccoli, cabbage, carrot, cauliflower, celery, cucumber, eggplant, lettuce, onion, pepper, potato, pumpkin, radish, spinach, squash, taro, tomato, and zucchini); fruit and nut crops (e.g., almond, apple, apricot, banana, black-berry, blueberry, cacao, cherry, coconut, cranberry, date, faJoa, filbert, grape, grapefr-uit, guava, kiwi, lemon, lime, mango, melon, nectarine, orange, papaya, passion fruit, peach, peanut, pear, pineapple, pistachio, plum, raspberry, strawberry, tangerine, walnut, and watermelon); and ornamentals (e.g., alder, ash, aspen, azalea, birch, boxwood, *camellia*, carnation, *chrysanthemum*, elm, fir, ivy, jasmine, juniper, oak, palm, poplar, pine, redwood, *rhododendron*, rose, and rubber). Examples of vertebrate animals include fish, mammal, cattle, goat, pig, sheep, rodent, hamster, mouse, rat, primate, and human; invertebrate animals include nematodes, other worms, *drosophila*, and other insects.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentarnycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of siRNA may result in inhibition in a smaller fraction of cells (e.g., at least 10%, 20%, 50%, 75%, 90%, or 95% of targeted cells). Quantitation of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

VIII. Methods of Treatment:

The present invention provides for both prophylactic and therapeutic methods of treating a subject at risk of (or susceptible to) a disorder or having a disorder associated with aberrant or unwanted target gene expression or activity. "Treatment", or "treating" as used herein, is defined as the application or administration of a therapeutic agent (e.g., a siRNA or vector or transgene encoding same) to a patient, or application or administration of a therapeutic agent to an isolated tissue or cell line from a patient, who has a disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted target gene expression or activity, by administering to the subject a therapeutic agent (e.g., a siRNA or vector or transgene encoding same). Subjects at risk for a disease which is caused or contributed to by aberrant or unwanted target gene expression or activity can be identified by, for example, any or a combination of diagnostic or prognostic assays as described herein. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject. The appropriate agent can be determined based on screening assays described herein.

2. Therapeutic Methods

Another aspect of the invention pertains to methods of modulating target gene expression, protein expression or activity for therapeutic purposes. Accordingly, in an exemplary embodiment, the modulatory method of the invention involves contacting a cell capable of expressing target gene with a therapeutic agent (e.g., a siRNA or vector or transgene encoding same) that is specific for the target gene or protein (e.g., is specific for the mRNA encoded by said gene or specifying the amino acid sequence of said protein) such that expression or one or more of the activities of target protein is modulated. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

3. Pharmacogenomics

The therapeutic agents (e.g., a siRNA or vector or transgene encoding same) of the invention can be administered to individuals to treat (prophylactically or therapeutically) disorders associated with aberrant or unwanted target gene activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11): 983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a target gene polypeptide of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a therapeutic agent of the present invention can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a therapeutic agent, as described herein.

Therapeutic agents can be tested in an appropriate animal model. For example, an siRNA (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent.

Alternatively, an agent can be used in an animal model to determine the mechanism of action of such an agent.

4. Disease Indications

The compositions of the invention can act as novel therapeutic agents for controlling one or more of cellular proliferative and/or differentiative disorders, disorders associated with bone metabolism, immune disorders, hematopoietic disorders, cardiovascular disorders, liver disorders, viral diseases, pain or metabolic disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer," "hyperproliferative," and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

In general, the compositions of the invention are designed to target genes associated with particular disorders. Examples of such genes associated with proliferative disorders that can be targeted include activated ras, p53, BRCA-1, and BRCA-2. Other specific genes that can be targeted are those associated with amyotrophic lateral sclerosis (ALS; e.g., superoxide dismutase-1 (SOD1)); Huntington's disease (e.g., huntingtin), Parkinson's disease (parkin), and genes associated with autosomal dominant disorders.

The compositions of the invention can be used to treat a variety of immune disorders, in particular those associated with overexpression of a gene or expression of a mutant gene. Examples of hematopoietic disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Examples of disorders involving the heart or "cardiovascular disorder" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, congestive heart failure, coronary artery disease, valvular disease, arrhythmias, and cardiomyopathies.

Disorders which may be treated by methods described herein include, but are not limited to, disorders associated with an accumulation in the liver of fibrous tissue, such as that resulting from an imbalance between production and degradation of the extracellular matrix accompanied by the collapse and condensation of preexisting fibers.

Additionally, molecules of the invention can be used to treat viral diseases, including but not limited to hepatitis B, hepatitis C, herpes simplex virus (HSV), HIV-AIDS, poliovirus, and smallpox virus. Molecules of the invention are engineered as described herein to target expressed sequences of a virus, thus ameliorating viral activity and replication. The molecules can be used in the treatment and/or diagnosis of viral infected tissue. Also, such molecules can be used in the treatment of virus-associated carcinoma, such as hepatocellular cancer.

IX. Pharmaceutical Compositions

The invention pertains to uses of the above-described agents for therapeutic treatments as described infra. Accordingly, the modulators of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

A therapeutically effective amount of a composition containing a compound of the invention (e.g., a siRNA, candidate siRNA derivative, modified siRNA, etc.) (i.e., an effective dosage) is an amount that inhibits expression of the polypeptide encoded by the target gene by at least 30 percent. Higher percentages of inhibition, e.g., 45, 50, 75, 85, 90 percent or higher may be preferred in certain embodiments. Exemplary doses include milligram or microgram amounts of the molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. The compositions can be administered one time per week for between about 1 to 10 weeks, e.g., between 2 to 8 weeks, or between about 3 to 7 weeks, or for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments.

It is furthermore understood that appropriate doses of a composition depend upon the potency of composition with respect to the expression or activity to be modulated. When one or more of these molecules is to be administered to an animal (e.g., a human) to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration.

X. Knockout and/or Knockdown Cells or Organisms

A further preferred use for the siRNA molecules of the present invention (or vectors or transgenes encoding same) is a functional analysis to be carried out in eukaryotic cells, or eukaryotic non-human organisms, preferably mammalian cells or organisms and most preferably human cells, e.g. cell lines such as HeLa or 293 or rodents, e.g. rats and mice. By administering a suitable siRNA molecules which is sufficiently complementary to a target mRNA sequence to direct target-specific RNA interference, a specific knockout or knockdown phenotype can be obtained in a target cell, e.g. in cell culture or in a target organism.

Thus, a further subject matter of the invention is a eukaryotic cell or a eukaryotic non-human organism exhibiting a target gene-specific knockout or knockdown phenotype comprising a fully or at least partially deficient expression of at least one endogenous target gene wherein said cell or organism is transfected with at least one vector comprising DNA encoding a siRNA molecule capable of inhibiting the expression of the target gene. It should be noted that the present invention allows a target-specific knockout or knockdown of several different endogenous genes due to the specificity of the siRNAi.

Gene-specific knockout or knockdown phenotypes of cells or non-human organisms, particularly of human cells or non-human mammals may be used in analytic to procedures, e.g. in the functional and/or phenotypical analysis of complex physiological processes such as analysis of gene expression profiles and/or proteomes. Preferably the analysis is carried out by high throughput methods using oligonucleotide based chips.

Using RNAi based knockout or knockdown technologies, the expression of an endogeneous target gene may be inhibited in a target cell or a target organism. The endogeneous gene may be complemented by an exogenous target nucleic acid coding for the target protein or a variant or mutated form of the target protein, e.g. a gene or a DNA, which may optionally be fused to a further nucleic acid sequence encoding a detectable peptide or polypeptide, e.g. an affinity tag, particularly a multiple affinity tag.

Variants or mutated forms of the target gene differ from the endogeneous target gene in that they encode a gene product which differs from the endogenous gene product on the amino acid level by substitutions, insertions and/or deletions of single or multiple amino acids. The variants or mutated forms may have the same biological activity as the endogeneous target gene. On the other hand, the variant or mutated target gene may also have a biological activity, which differs from the biological activity of the endogeneous target gene, e.g. a partially deleted activity, a completely deleted activity, an enhanced activity etc. The complementation may be accomplished by compressing the polypeptide encoded by the endogenous nucleic acid, e.g. a fusion protein comprising the target protein and the affinity tag and the double stranded RNA molecule for knocking out the endogeneous gene in the target cell. This compression may be accomplished by using a suitable expression vector expressing both the polypeptide encoded by the endogenous nucleic acid, e.g. the tag-modified target protein and the double stranded RNA molecule or alternatively by using a combination of expression vectors. Proteins and protein complexes which are synthesized de novo in the target cell will contain the exogenous gene product, e.g., the modified fusion protein. In order to avoid suppression of the exogenous gene product by the siRNAi molecule, the nucleotide sequence encoding the exogenous nucleic acid may be altered at the DNA level (with or without causing mutations on the amino acid level) in the part of the sequence which so is homologous to the siRNA molecule. Alternatively, the endogeneous target gene may be complemented by corresponding nucleotide sequences from other species, e.g. from mouse.

XI. Functional Genomics and/or Proteomics

Preferred applications for the cell or organism of the invention is the analysis of gene expression profiles and/or proteomes. In an especially preferred embodiment an analysis of a variant or mutant form of one or several target proteins is carried out, wherein said variant or mutant forms are reintroduced into the cell or organism by an exogenous target nucleic acid as described above. The combination of knockout of an endogenous gene and rescue by using mutated, e.g. partially deleted exogenous target has advantages compared to the use of a knockout cell. Further, this method is particularly suitable for identifying functional domains of the targeted protein. In a further preferred embodiment a comparison, e.g. of gene expression profiles and/or proteomes and/or phenotypic characteristics of at least two cells or organisms is carried out. These organisms are selected from: (i) a control cell or control organism without target gene inhibition, (ii) a cell or organism with target gene inhibition and (iii) a cell or organism with target gene inhibition plus target gene complementation by an exogenous target nucleic acid.

Furthermore, the RNA knockout complementation method may be used for is preparative purposes, e.g. for the affinity purification of proteins or protein complexes from eukaryotic cells, particularly mammalian cells and more particularly human cells. In this embodiment of the invention, the exogenous target nucleic acid preferably codes for a target protein which is fused to art affinity tag. This method is suitable for functional proteome analysis in mammalian cells, particularly human cells.

Another utility of the present invention could be a method of identifying gene function in an organism comprising the use of siRNA to inhibit the activity of a target gene of previously unknown function. Instead of the time consuming and laborious isolation of mutants by traditional genetic screening, functional genomics would envision determining the function of uncharacterized genes by employing the invention to reduce the amount and/or alter the timing of target gene activity. The invention could be used in determining potential targets for pharmaceutics, understanding normal and pathological events associated with development, determining signaling pathways responsible for postnatal development/aging, and the like. The increasing speed of acquiring nucleotide sequence information from genomic and expressed gene sources, including total sequences for the yeast, *D. melanogaster*, and *C. elegans* genomes, can be coupled with the invention to determine gene function in an organism (e.g., nematode). The preference of different organisms to use particular codons, searching sequence databases for related gene products, correlating the linkage map of genetic traits with the physical map from which the nucleotide sequences are derived, and artificial intelligence methods may be used to define putative open reading frames from the nucleotide sequences acquired in such sequencing projects. A simple assay would be to inhibit gene expression according to the partial sequence available from an expressed sequence tag (EST). Functional alterations in growth, development, metabolism, disease resistance, or other biological processes would be indicative of the normal role of the EST's gene product.

The ease with which RNA can be introduced into an intact cell/organism containing the target gene allows the present invention to be used in high throughput screening (HTS). Solutions containing siRNAs that are capable of inhibiting the different expressed genes can be placed into individual wells positioned on a microtiter plate as an ordered array, and intact cells/organisms in each well can be assayed for any changes or modifications in behavior or development due to inhibition of target gene activity. The amplified RNA can be fed directly to, injected into, the cell/organism containing the target gene. Alternatively, the siRNA can be produced from a vector, as described herein. Vectors can be injected into, the cell/organism containing the target gene. The function of the target gene can be assayed from the effects it has on the cell/organism when gene activity is inhibited. This screening could be amenable to small subjects that can be processed in large number, for example: arabidopsis, bacteria, drosophila, fungi, nematodes, viruses, zebrafish, and tissue culture cells derived from mammals. A nematode or other organism that produces a colorimetric, fluorogenic, or luminescent signal in response to a regulated promoter (e.g., transfected with a reporter gene construct) can be assayed in an HTS format.

The present invention may be useful in allowing the inhibition of essential genes. Such genes may be required for cell or organism viability at only particular stages of development or cellular compartments. The functional equivalent of conditional mutations may be produced by inhibiting activity of the target gene when or where it is not required for viability. The invention allows addition of siRNA at specific times of development and locations in the organism without introducing permanent mutations into the target genome.

XII. Screening Assays

The methods of the invention are also suitable for use in methods to identify and/or characterize potential pharmacological agents, e.g. identifying new pharmacological agents from a collection of test substances and/or characterizing mechanisms of action and/or side effects of known pharmacological agents.

Thus, the present invention also relates to a system for identifying and/or characterizing pharmacological agents acting on at least one target protein comprising: (a) a eukaryotic cell or a eukaryotic non-human organism capable of expressing at least one endogeneous target gene coding for said so target protein, (b) at least one siRNA molecule capable of inhibiting the expression of said at least one endogeneous target gene, and (c) a test substance or a collection of test substances wherein pharmacological properties of said test substance or said collection are to be identified and/or characterized. Further, the system as described above preferably comprises: (d) at least one exogenous target nucleic acid coding for the target protein or a variant or mutated form of the target protein wherein said exogenous target nucleic acid differs from the endogeneous target gene on the nucleic acid level such that the expression of the exogenous target nucleic acid is substantially less inhibited by the siRNA molecule than the expression of the endogeneous target gene.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.)).

In a preferred embodiment, the library is a natural product library, e.g., a library produced by a bacterial, fungal, or yeast culture. In another preferred embodiment, the library is a synthetic compound library.

XIII. Uses of siRNA Derivatives to Induce RNAi

An siRNA derivative, introduced into cells or whole organisms as described herein, will associate with endogenous protein components of the RNAi pathway to bind to and target a specific mRNA sequence for cleavage and destruction. In this fashion, the mRNA to be targeted by the siRNA derivative will be depleted from the cell or organism, leading to a decrease in the concentration of the protein encoded by that mRNA in the cell or organism.

For example, one may be seeking to discover a small molecule that reduces the activity of a kinase whose overexpression leads to unrestrained cell proliferation. This kinase is overexpressed in a variety of cancer cells. A key question to be determined is whether or not decreasing the activity of this kinase would have unexpected deleterious effects on a cell. By expressing an siRNA derivative that targets for destruction by the RNAi pathway the mRNA encoding the kinase in a cell, the deleterious effects of such a potential drug can be determined. That is, the method described here will allow rapid assessment of the suitability of the kinase as a drug target. One advantage of using an siRNA derivative over a conventional siRNA is that the siRNA derivative can be more stable, thus the effect of sustained exposure of a cell to a decrease in expression of a targeted gene can be assessed.

RNAi provides a new approach for elucidation of gene function. RNAi-mediated gene knockdown is useful for genome-wide analysis of gene function as well as target validation of potentially therapeutic genes. siRNAs are a useful tool for cell biologists studying mammalian gene function. For example, siRNAs are useful for the analysis of general cell biological mechanisms such as mitosis, processing and traffic of RNA transcripts, the formation of cellular junctions, and membrane trafficking. Reagents that can be used for such analyses (e.g. siRNA derivatives that have increased stability in a cell compared to their corresponding, unmodified siRNA) have commercial value for use in such research.

A selected gene can be knocked down by use of an siRNA and the resultant phenotype can be observed. However, knockdown of an essential gene could be lethal or toxic and may affect many pathways in the cell. Therefore, in some cases it is desirable to provide to the cell an siRNA that is not maximally efficient at knockdown (i.e., inhibiting expression of the protein translated from the targeted sequence). The adverse effects of an overly efficient knockdown can be modulated by contacting the cell with an siRNA derivative that has reduced RNAi activity compared to a corresponding siRNA. Suitable concentrations of an siRNA derivative used for this purpose include concentrations that do not maximally inhibit RNAi activity and ameliorate the undesirable effect of the siRNA. An amount of an siRNA derivative that can cause knockdown with less efficiency than a corresponding siRNA can be determined using the dual fluorescence assay described herein by incubating an amount of siRNA derivative targeted to a hybrid reporter gene and detecting the amount of inhibition of reporter gene expression. If desired, the level of fluorescence can be compared to that in a corresponding dual fluorescence reporter assay in which the corresponding siRNA was used instead of the siRNA derivative. In some cases, a useful siRNA derivative is one that inhibits RNAi by less than 100%. For example, an siRNA derivative that is useful for reducing the RNAi effect of an siRNA can inhibit RNAi activity by less than, e.g., 90%, 75%, 50%, 25%, or 10%.

This invention is further illustrated by the following examples which should not be construed as limiting. The contents of all references, patents and published patent applications cited throughout this application are incorporated herein by reference.

EXAMPLES

Examples I-VII demonstrate that the status of the 5' hydroxyl terminus of the antisense strand determines RNAi activity, whereas a 3' terminus block is well tolerated in vivo. Isolation of siRNA from human cells revealed that 5' hydroxyl termini of antisense strands were phosphorylated and 3' end biotin groups were not efficiently removed. There was no requirement for a perfect A-form helix in siRNA for interference effects, but an A-form structure was required for antisense-target RNA duplexes. Strikingly, cross-linking of the siRNA duplex by psoralen did not completely block RNA interference, indicating that complete unwinding of the siRNA helix is not necessary for RNAi activity in vivo. These results highlight the importance of 5' hydroxyl in the antisense strand of siRNA, which is essential to initiate the RNAi pathway, and suggest a model where RNA amplification by RNA-dependent RNA polymerase is not essential for RNAi in human cells.

Example I: Dual Fluorescence Reporter System for RNAi Analysis in Mammalian Cells To explore the functional anatomy of siRNA in mammalian cells, a dual fluorescence reporter system was established using HeLa cells as a model system. Two reporter plasmids were used: pEGFP-C1 and pDsRed1-N1, harboring enhanced green fluorescent protein (GFP) or coral (*Discosoma* spp.)-derived red fluorescent protein (RFP), respectively. The expression of these reporter genes was under cytomegalovirus promoter control and could be easily visualized by fluorescence microscopy in living cells. The siRNA sequence targeting GFP was from position 238-258 relative to the start codon, and the RFP siRNA sequence was from position 277-297 relative to the start codon (FIG. 1A). Using lipofectamine, HeLa cells were cotransfected with pEGFP-C1 and pDsRed1-N1 expression plasmids and siRNA duplex, targeting either GFP or RFP. Fluorescence imaging was used to monitor GFP and RFP expression levels. As shown in FIG. 1B (panels a and b), mock treatment (without siRNA) allowed efficient expression of both GFP and RFP in living cells. Transfection of cells with siRNA duplex targeting GFP (GFP ds) significantly reduced GFP expression (FIG. 1B, panel c), but had no effect on RFP expression (FIG. 1B, panel d) compared with mock-treated cells (FIG. 1B, panels a and b). By contrast, transfection of cells with siRNA duplex targeted to RFP (RFP ds) significantly interfered with the expression of RFP, but not GFP (FIG. 1B, panels e and f).

To quantify RNAi effects, lysates were prepared from siRNA duplex-treated cells at 42 hours post transfection. GFP and RFP fluorescence in clear lysates was measured on a fluorescence spectrophotometer. The peak at 507 nm (FIG. 1C, left panel) represents the fluorescence intensity of GFP, and the peak at 583 nm (FIG. 1C, right panel) represents the fluorescence intensity of RFP. GFP fluorescence intensity of GFP ds-treated cells (FIG. 1C, left panel, green line) was only 5% of mock-treated (black line) or RFP ds-treated cells (cyan line). In contrast to GFP fluorescence, RFP fluorescence intensity (FIG. 1C, right panel) significantly decreased only in cells treated with RFP ds (red line), indicating the specificity of the RNAi effect.

Figure 1D:
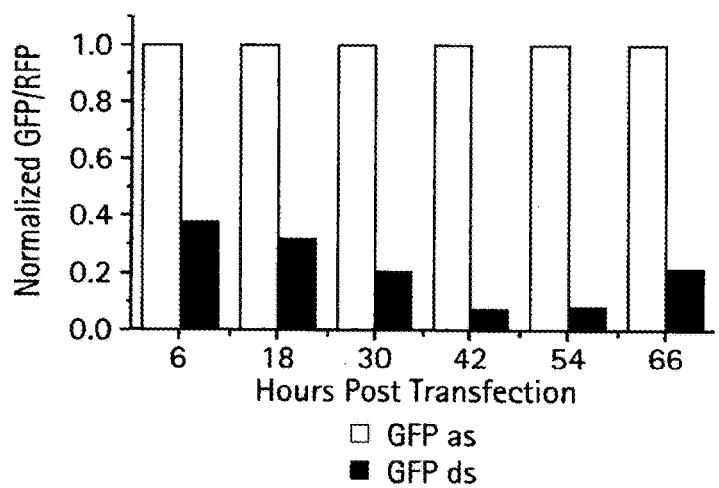
Figure 1E:
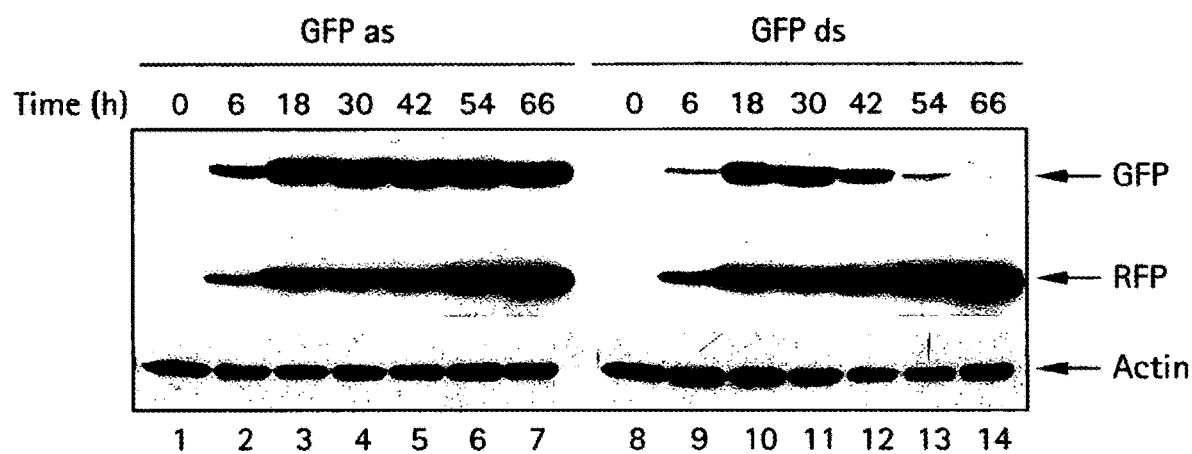
FIG. 1E-F depicts analysis of specific RNAi activities by Western blotting. Antisense and double strand RNA are indicated as as and ds, respectively. GFP as (E, left panel), GFP ds (E, right panel), RFP as (F, left panel) or RFP ds (F, right panel) were cotransfected with pEGFP-C1 and pDsRed1-N1 reporter plasmids into HeLa cells. Cells were harvested at various times, resolved on 10% SDS-PAGE, transferred onto PVDF membranes, and immunoblotted with antibodies against EGFP and DsRed1-N1. The membrane was stripped and re-probed with anti-actin antibody to check for equal loading of total proteins.
Figure 1F:
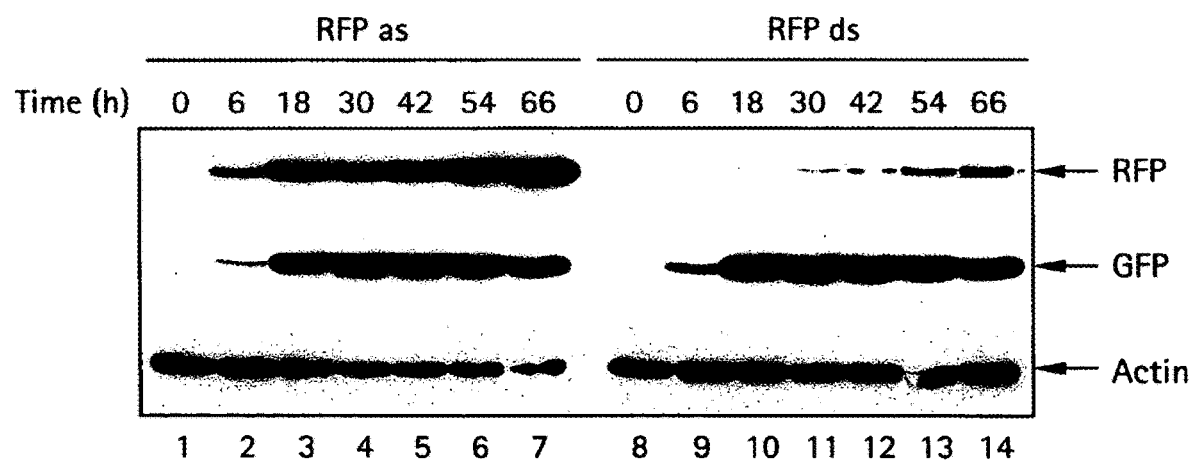

To confirm these findings on RNAi effects in living mammalian cells, Western blotting experiments were performed using anti-GFP and anti-RFP antibodies. Analysis of immunoblots revealed that the siRNA targeting GFP inhibited only GFP expression without affecting RFP levels (FIG. 1E, lanes 9-14); siRNA targeting RFP was similarly specific against RFP expression (FIG. 1F, lanes 9-14). This RNA interference effect depended on the presence of 21-nucleotide duplex siRNA, but not of the antisense strand siRNA (FIGS. 1E and F; compare right and left panels). These results demonstrate a reliable and quantitative system for studying specific RNA interference in HeLa cells.

Example II: Kinetics of RNA Interference in HeLa Cells

One of the many intriguing features of gene silencing by RNA interference is its unusually high efficiency—a few dsRNA molecules suffice to inactivate a continuously transcribed target mRNA for long periods of time. It has been demonstrated in plants (Cogoni and Macino, 1999; Dalmay et al., 2000) and worms (Grishok et al., 2000) that this inactivation can spread throughout the organism and is often heritable to the next generation. Mutations in genes encoding a protein related to RdRP affect RNAi-type processes in *Neurospora* (QDE-1; Cogoni and Macino, 1999), *C. elegans* (EGO-1; Smardon et al., 2000) and plants ([SGS2; Mourrain et al., 2000] and [SDE-1; Dalmay et al., 2000]). The involvement of RdRP in amplifying RNAi has been postulated (Lipardi et al., 2001).

Figure 1G:
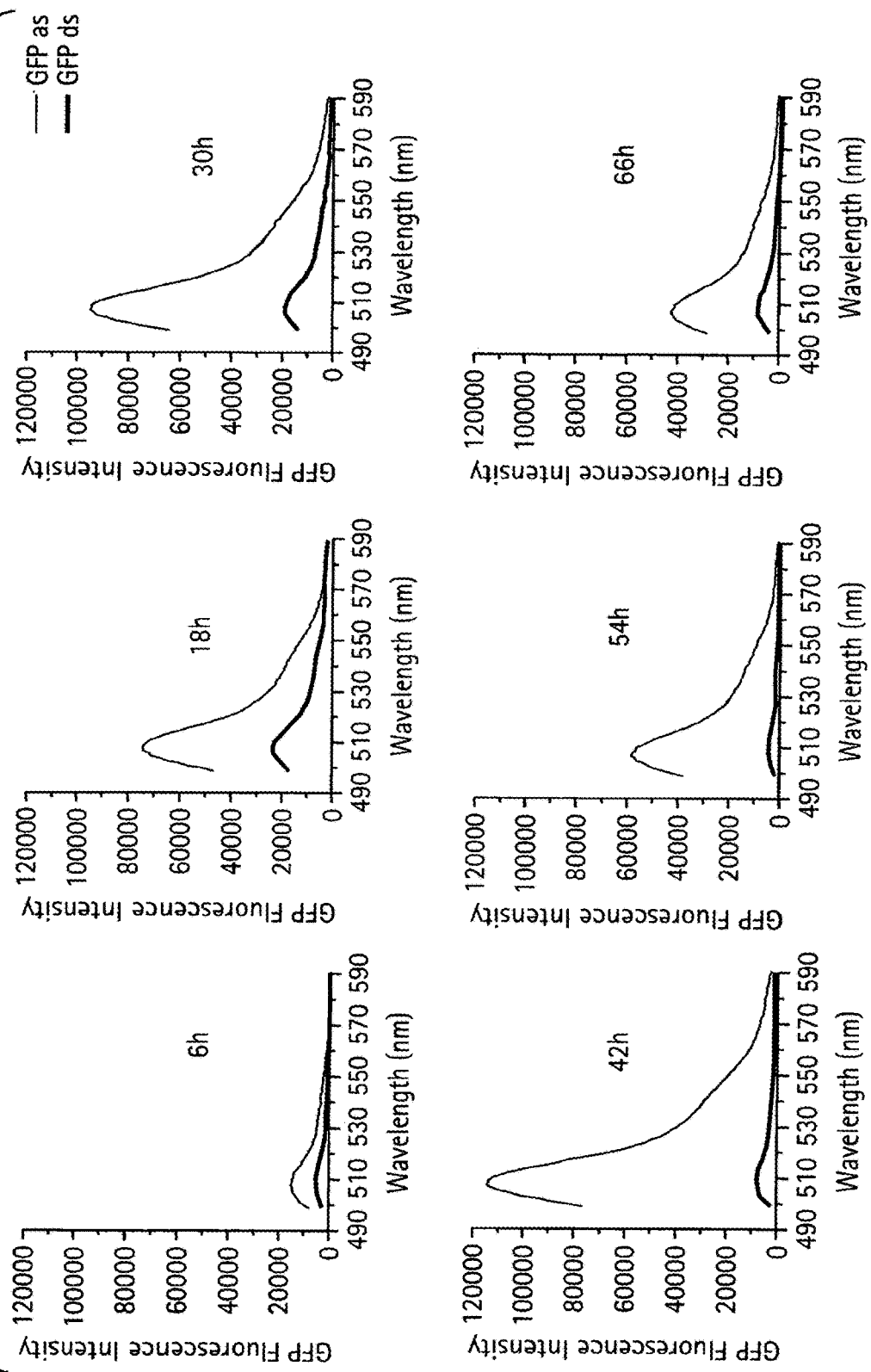
FIG. 1G depicts expression of GFP in HeLa cells treated with antisense or double-stranded siRNA targeting GFP. Transfected cells were harvested at various times after transfection and total cell lysates were analyzed by fluorescence spectroscopy. Fluorescence emission spectra of GFP and RFP were detected by exciting at 488 nm and 568 nm, respectively.

To understand the kinetics of gene suppression and persistence of RNA interference in HeLa cells, lysates were prepared from cells cotransfected with GFP siRNA and dual fluorescence reporter plasmids, pEGFP-C1 and pDsRed1-N1. In this experiment, GFP was the target of the duplex siRNA, while RFP was used as a control for transfection efficiency and specificity of RNA interference. Emission spectra of GFP in cell lysates at various times after transfection (FIG. 1G, Supplementary Material) show that siRNA duplex caused an RNA interference effect as early as 6 hours post transfection. This effect gradually increased with time, peaking at 42 hours, then started to decrease at 66 hours (FIG. 1G, green lines). As a control experiment, GFP expression in the presence of antisense strand was also monitored and showed no RNAi effects (FIG. 1G, blue lines). Thus, RNA interference can last for at least 66 hours in HeLa cells (FIG. 1G, green lines).

To quantify the kinetics of RNA interference, the fluorescence intensity ratio of target (GFP) to control (RFP) fluorophore in the presence of siRNA duplex (ds) was measured and normalized it to the ratio observed in the presence of antisense strand siRNA (as). Normalized ratios less than 1.0 indicate specific interference. As shown in FIG. 1D, at 6 hours post transfection GFP duplex siRNA (green bars) inhibits 60% of GFP expression compared to antisense strand siRNA (blue bars). RNA interference reached its maximum (92% inhibition) at 42 hours post transfection; only 8% of normal GFP expression was observed in duplex siRNA-treated cells. These results show that RNA interference can suppress target protein expression up to 66 h, although maximum activities were observed at 42-54 h post transfection.

Example III: Free 5' OH Groups on the Antisense Strand of the siRNA Duplex are Required for RNA Interference In Vivo Synthetic 21-nucleotide siRNA duplexes with 5' hydroxyl termini and 3' overhang have been shown to specifically suppress expression of endogenous and heterologous genes in *Drosophila* extracts (Elbashir et al., 2001b) and mammalian cell lines (Elbashir et al., 2001a). Nonetheless, native siRNA, processed by Dicer cleavage of dsRNA, contains 5' phosphate ends (Elbashir et al., 2001b). It has been demonstrated in vitro that *Drosophila* embryo lysates contain a potent kinase activity that phosphorylates the 5' hydroxyl termini of synthetic siRNAs (Nykanen et al., 2001). The 5' phosphate is required on the siRNA strand that guides target cleavage in RNA interference (Nykanen et al., 2001).

Figure 2A:
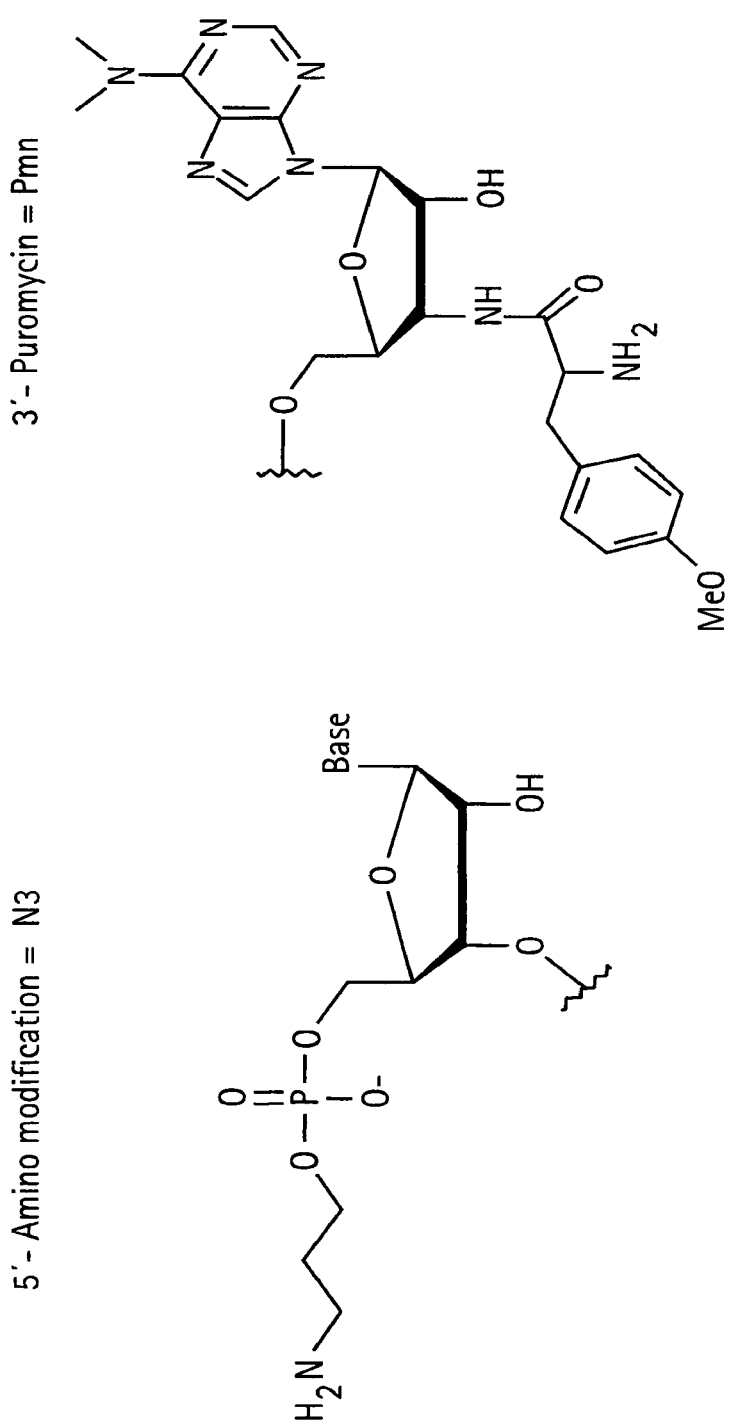
Figure 3A:
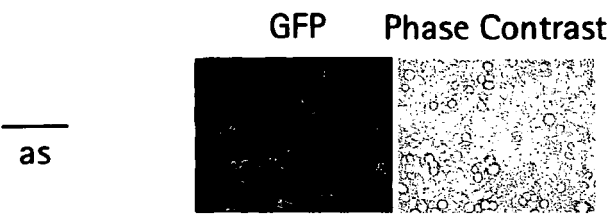
FIG. 3A-L depicts fluorescence images showing RNA interference effects in living HeLa cells transfected with modified siRNA duplexes. HeLa cells were cotransfected by lipofectamine with pEGFP-C1, pDsRed1-N1 reporter plasmids and siRNA with a 5' modification (panels C, D, and E), 3' modification (panels F, G, H, and I) or internal bulge (panels J, K, and L). Fluorescence in living cells was visualized at 48 hours post transfection. GFP fluorescence (left panels) and phase contrast images (right panels) are shown. RNA used in each experiment is indicated on the left of each pair of panels.
Figure 3B:
Figure 3C:
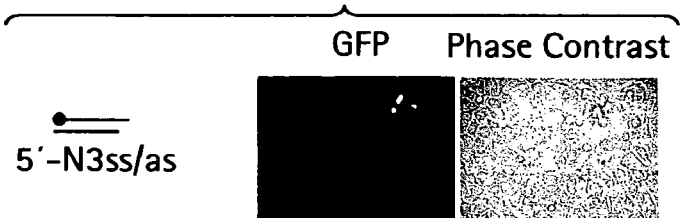
Figure 3D:
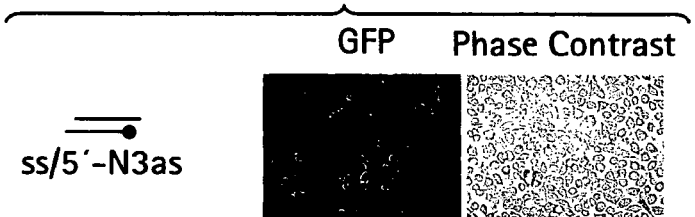
Figure 3E:
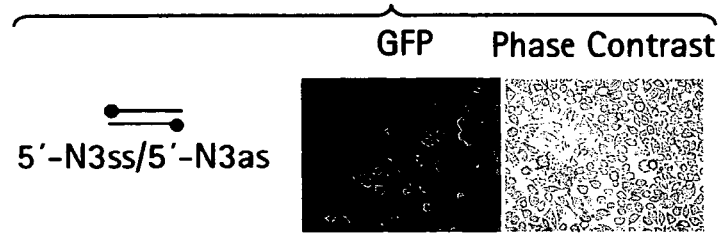
Figure 3F:
Figure 3G:
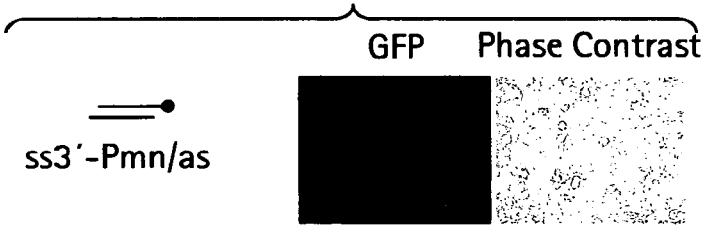
Figure 3H:
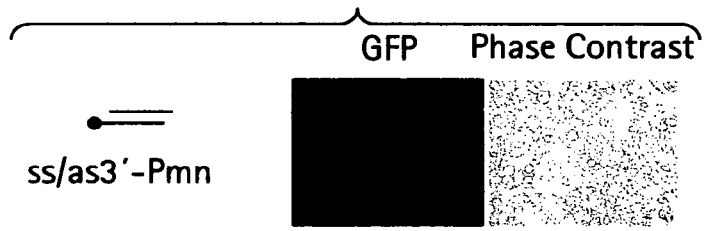
Figure 3I:
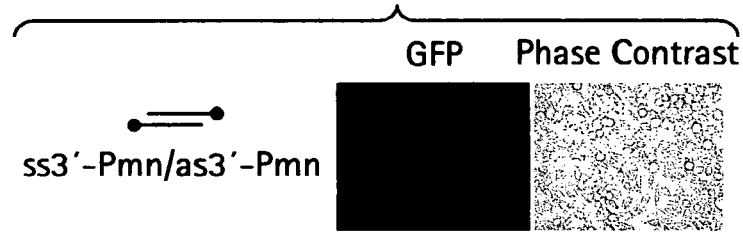
Figure 3J:
Figure 3K:
Figure 3L:
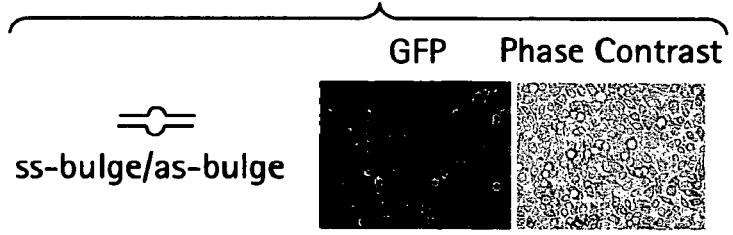
Figure 4A:
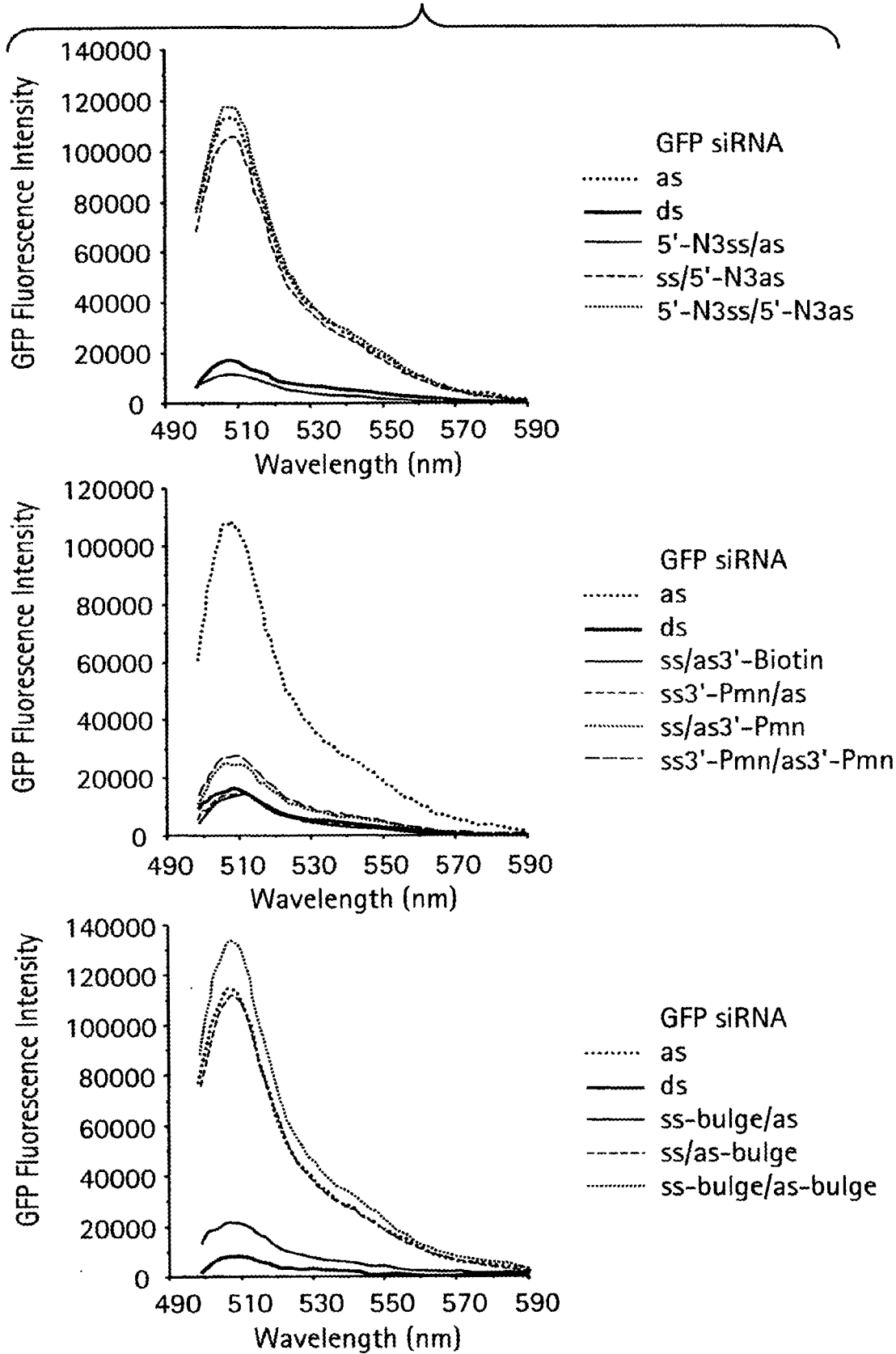
FIG. 4A-B depicts quantitative analysis of RNAi effects in HeLa cells transfected with modified siRNAs. pEGFP-C1 (as reporter), pDsRed1-N1 (as control) plasmids and 50 nM siRNA were cotransfected into HeLa cells by lipofectamine. Cells were harvested at various times after transfection. Fluorescence emission spectra of GFP and RFP in total cell lysates were detected by exciting at 488 nm and 568 nm, respectively. (A) GFP emission spectra of modified siRNAi-treated cells. Emission spectra of GFP in lysates from cells transfected with 5'-modified GFP siRNAs (upper panel), 3'-modified GFP siRNAs (middle panel) and bulge-containing GFP siRNAs (lower panel). For comparison, results from antisense- (as, red line) and unmodified duplex siRNA (ds, black line)-treated cells are included in each panel. (B) Ratios of normalized GFP to RFP fluorescence intensity in lysates from modified siRNA-treated HeLa cells over 66 hours. The fluorescence intensity ratio of target (GFP) to control (RFP) fluorophore was determined in the presence of 5'-modified GFP siRNAs (upper panel), 3'-modified GFP siRNAs (middle panel), and bulge-containing GFP siRNAs (lower panel) and normalized to the ratio observed in the presence of antisense strand siRNA. Normalized ratios less than 1.0 indicate specific RNA interference effects. For comparison, results from antisense RNA and duplex siRNA-treated cells are included in each panel (as, orange bars; ds, yellow bars).
Figure 4B:
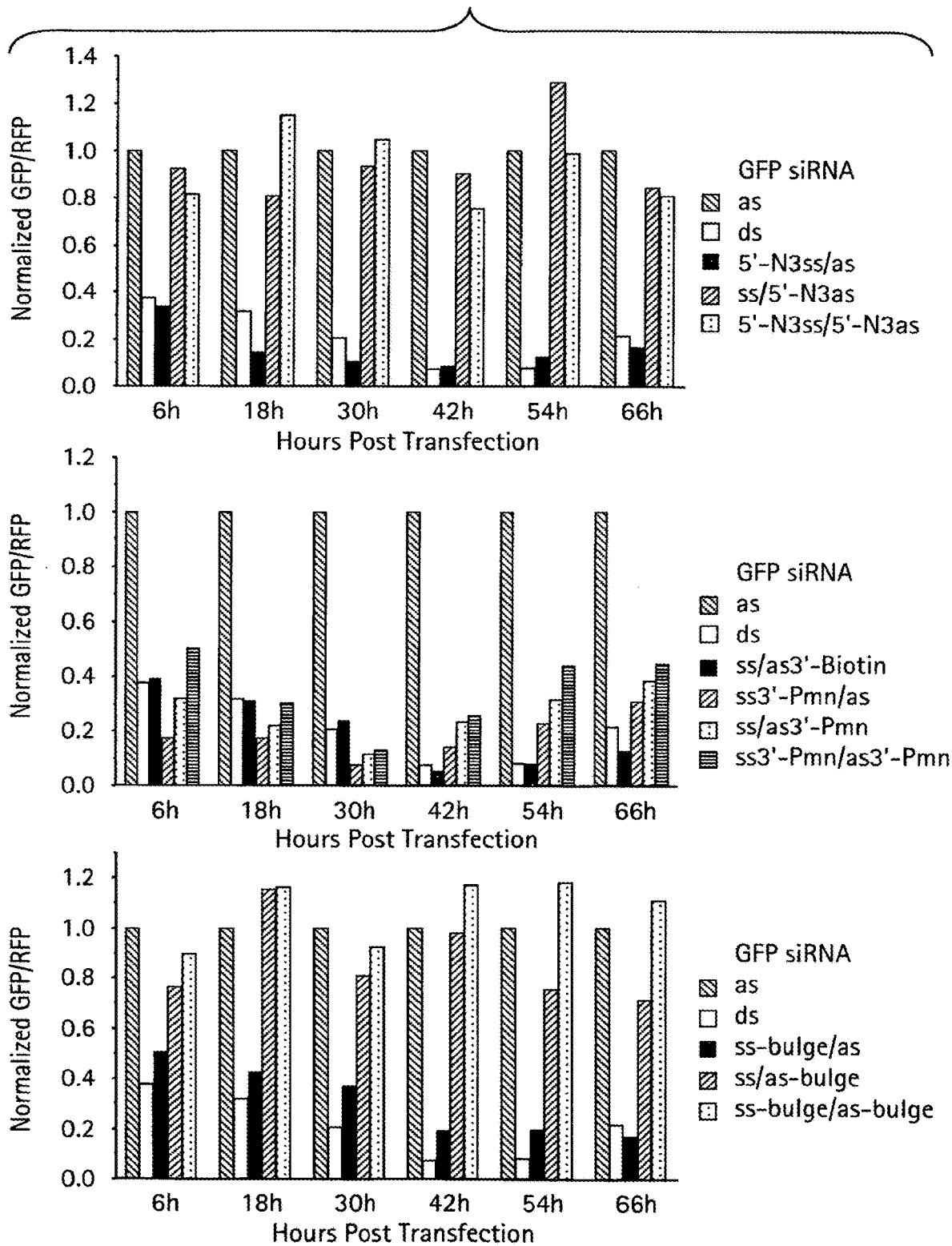

To examine the importance of 5' termini of siRNA in RNA interference in human cells, synthetic siRNAs targeting GFP were modified by using an amino group with a 3-carbon linker (5' N3, FIG. 2A) to block their 5' termini. Synthetic siRNAs with this modification lacked a hydroxyl group to be phosphorylated by kinases in vivo. This modification could also block access to siRNA by cellular factors that might require recognizing the 5' OH termini. Unmodified siRNA strands were annealed with 5'-modified strands, producing siRNA duplexes with 5' modification at only the sense strand (5'-N3ss/as), at only the antisense strand (ss/5'-N3as) or at both strands (5'-N3ss/5'-N3as) (FIG. 2B). RNAi effects of these siRNA duplexes were analyzed in the dual fluorescence reporter system as described in FIG. 1. 5' modification of the sense strand had no effect on RNAi activity (FIG. 3, compare panels b and c), whereas 5' modification of the antisense strand completely abolished the RNAi effect (FIG. 3, panels d and e; FIGS. 4A and 4B, upper panels). HeLa cells transfected with antisense strand (as) siRNA as control showed no RNAi activity (FIG. 3, panel a). These results demonstrate that the 5' OH in the antisense strand of the siRNA duplex is an important determinant of RNAi activity in human cells.

Figure 5:
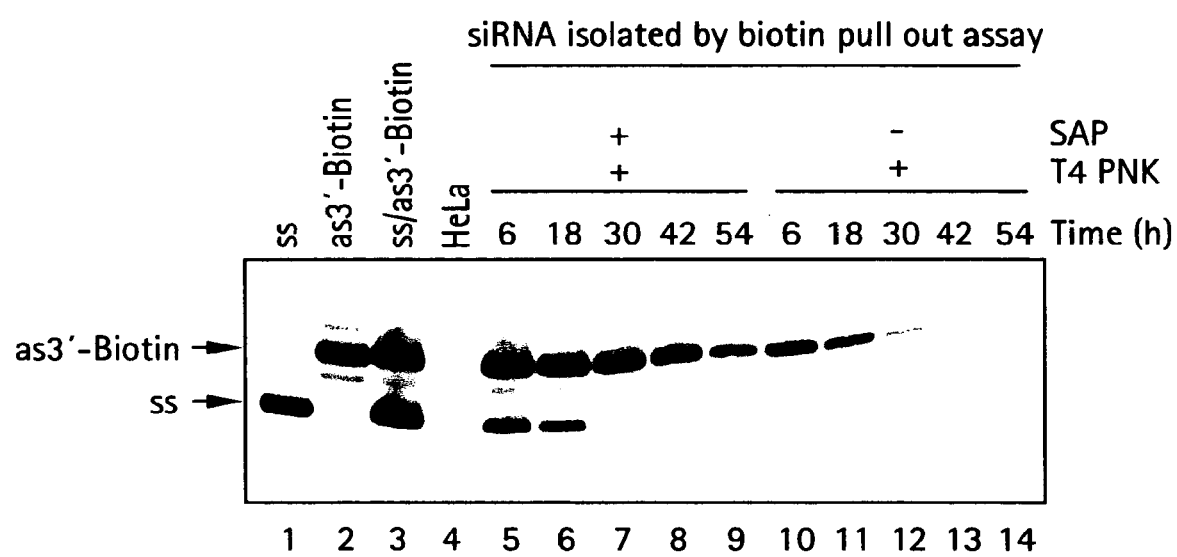
FIG. 5 depicts the isolation of 5' end phosphorylated and 3' end biotinylated siRNA from HeLa cells. HeLa cells were cotransfected with biotinylated GFP duplex siRNA (ss/as3'-Biotin) and pEGFP-C1 plasmid as described in Experimental Procedures. The siRNA was isolated by pull out assay and subjected to phosphatase and kinase reactions (see Experimental Procedures). Briefly, streptavidin magnetic beads were used to pull out biotinylated siRNAs from transfected cells, washed to remove unbound RNA, and split into two aliquots. One aliquot was dephosphorylated with shrimp alkaline phosphatase (SAP), and the RNA 5' ends labeled with $^{32}P$ by T4 polynucleotide kinase (PNK) reaction. The other aliquot was not dephosphorylated. RNA was resolved on 20% polyacrylamide-7M Urea gels and visualized by phosphorimager analysis. Lanes 1-3 (marker lanes) contain 5'-end-labeled RNA: lane 1, sense strand (ss); lane 2, 3' biotinylated antisense strand (as3'-Biotin); lane 3, heat denatured (10 min at 95° C.) siRNA duplex (ss/as3'-Biotin). Lanes 5-14, isolated biotinylated siRNA with SAP treatment (lanes 5-9) or without (lanes 10-14). Lane 4, RNA isolated as above from HeLa cells without siRNA transfection.

Example IV: Blocking the 3' End of siRNAs has Little Effect on RNA Interference In Vivo To determine the effect of 3' OH groups on RNAi activity, siRNA duplexes were synthesized containing a 3' end blocked with 3' puromycin (3'-Pmn, FIG. 2A) or biotin instead of 3' OH groups on the overhang deoxythymidine (FIG. 2B). These 3' end modifications would block any processing of the siRNA duplex that required a free 3' hydroxyl group. Three combinations of siRNA duplexes were prepared containing 3' puromycin: 3' blocked at only the sense strand (ss3'-Pmn/as), at only the antisense strand (ss/as3'-Pmn), or at both strands (ss3'-Pmn/as3'-Pmn) (FIG. 2B). A siRNA duplex containing biotin at the 3'-end of antisense strand (ss/as3'-Biotin) was also prepared. The RNAi activities of these siRNA duplexes were analyzed in our dual fluorescence reporter system. Results of these experiments indicate that a 3' block at either the sense or antisense strand of siRNA duplex had little effect on its RNA interference activity (FIG. 3, panels f-i; FIGS. 4A and 4B, middle panels). Furthermore, biotin pull out experiments showed that the 3' end biotin groups on the antisense strand were not efficiently removed during RNAi activities in HeLa cells (FIG. 5, see below). Modifications could be introduced in the 3' overhangs without affecting siRNA efficacy, suggesting that RNA interference in mammalian cells does not occur through the recently reported RdRP-dependent degradative PCR mechanism (Lipardi et al., 2001; Sijen et al., 2001), which requires a free 3' hydroxyl group.

Example V: A-Form Helix of siRNA is Absolutely Required for Effective RNA Interference In Vivo Synthetic and native siRNAs, generated from ATP-dependent cleavage of double strand RNA, have been proposed to act as "guide RNAs" that target an associated nuclease complex, the RISC (RNA-induced silencing complex), to the corresponding mRNA through strand complementarity (Hammond et al., 2000; Nykanen et al., 2001). How are these siRNA duplexes recognized and incorporated into the RISC protein complex? siRNA duplexes are readily characterized by their A-form helix, which can be distinguished from the structures of B-form helix DNA and single-stranded RNA in the cell. A single mismatch between a target mRNA and its guide strand siRNA completely prevents target RNA cleavage in *Drosophila* embryo lysates (Elbashir et al., 2001c). Although the mechanism of target recognition has not been experimentally demonstrated, this finding indicates that recognition requires exact complementarity between the guide strand and target mRNA.

These observations raise two fundamental questions regarding RNAi effects in vivo: (1) Is an A-form RNA helix required in the siRNA structure? (2) Is an A-form helix recognized by proteins after the antisense strand of siRNA duplex is hybridized with the target mRNA? To address these questions, three siRNA duplexes were designed containing internal bulge structures in the RNA helices (FIG. 2B). The A-form RNA helix has a deep, narrow major groove and a shallow, wide minor groove. More than one nucleotide bulge has been shown to distort RNA helical structures, widening the major groove and enhancing accessibility to its functional groups (Neenhold and Rana, 1995; Weeks and Crothers, 1991; Weeks and Crothers, 1993). 2-nt bulges were chosen to generate distorted A-form helices in siRNAs. Mutant siRNA were synthesized by introducing two extra nucleotides into the sense or antisense strand of siRNA duplexes. Combining these mutant siRNA strands with original siRNA sequences produced three siRNA duplexes with an internal bulge at only the sense strand (ss-bulge/as), at only the antisense strand (ss/as-bulge), or at both strands (ss-bulge/as-bulge) (FIG. 2B). This design of bulge-containing siRNAs could dissect the requirement for the A-form helix at two different steps of RNA interference: 1) siRNA recognition by RISC, and 2) RISC targeting of mRNA via the guiding siRNA. siRNA duplexes with an internal bulge at only the sense strand (ss-bulge/as) caused a structural change in the siRNA duplex (an imperfect A-form) without affecting the complementarity between target mRNA and the antisense strand, which acts as the guiding strand in the RNA interference pathway. RNA interference by these siRNA duplexes was analyzed and quantified in the dual fluorescence reporter system as described above.

Surprisingly, the siRNA duplex containing a bulge in its sense strand retained most of its RNA interference activity (FIG. 3, compare panels b and j; FIGS. 4A and 4B, lower panels, green line and bars), indicating that an A-form siRNA helix is not essential for effective RNA interference in vivo. However, bulges in the antisense strand or both strands of duplex siRNA completely abolished RNA interference ability (FIG. 3, panels k and l; FIGS. 4A and 4B, lower panels, dark and light blue line and bars), indicating that effective RNA interference in vivo absolutely requires A-form helix formation between target mRNA and its guiding antisense strand.

Example VI: 5' OH Groups on the Antisense Strand of the siRNA Duplex are Phosphorylated In Vivo To analyze the phosphorylation status of the 5' termini of siRNA and to probe the participation of siRNA 3' termini in the RNA interference pathway in vivo, HeLa cells were transfected with 21-nt RNAs containing biotin at the 3' terminal of the antisense strand (ss/as3'-Biotin) and isolated the biotinylated siRNA at various times after transfection (see Experimental Procedures). Briefly, streptavidin magnetic beads were used to pull out biotinylated siRNAs from transfected cells, washed to remove unbound RNA, and split into two aliquots. One aliquot was dephosphorylated with shrimp alkaline phosphatase (SAP), and the RNA 5' ends labeled with $^{32}$P by T4 polynucleotide kinase (PNK) reaction. The other aliquot was subjected to 5' end radiolabeling with polynucleotide kinase without prior dephosphorylation reaction with SAP. RNA was resolved on 20% polyacrylamide-7M urea gels and visualized by phosphorimager analysis. Cells without siRNA treatment showed no detectable signal after biotin pull out assay (FIG. 5, lane 4), indicating the absence of non-specific RNA-bead interactions. Efficient 5'-end radiolabeling was observed only when RNA was pretreated with phosphatase (compare lanes 5-9 and 10-14), indicating that the 5' termini of siRNA did not contain free OH groups in vivo. Although phosphorylating with SAP and quenching the phosphatase reaction by heating resulted in some RNA degradation, the efficiency of the kinase reaction after SAP treatment is obvious. These results indicate that 5' OH groups are phosphorylated in vivo for RNAi activities.

These experiments have three key findings. First, biotinylated-siRNA can be isolated from HeLa cells at 6 to 54 hours post transfection (FIG. 5, lanes 5-9). The amount of isolated siRNA decreased in a time-dependent manner, indicating the degradation of siRNA in vivo. The dual fluorescence assays showed that RNA interference mediated by 3' end biotinylated siRNA was as effective as unmodified siRNA (FIG. 3, panels f and b; FIGS. 4A and 4B, middle panel). RNA interference is seen as early as 6 hours post siRNA transfection and can be maintained for 42 hours post transfection. The ability to isolate biotin-RNA from cells after RNA interference had been initiated indicates that biotin was not removed from the RNA and rules out the possibility of siRNA 3' OH termini involvement in the RNA interference pathway in human cells.

Second, in this biotin pull out assay, only siRNA with 5' OH ends can be $^{32}$P-labeled by T4 PNK. As shown in FIG. 5, the siRNA without SAP treatment was not efficiently labeled by T4 PNK (e.g., compare lane 10 to lane 5 and lane 11 to lane 6), indicating that the 5' termini of siRNA did not contain free OH groups in vivo. These 5' terminal groups can be removed by alkaline phosphatase treatment for subsequent radiolabeling (FIG. 5, lanes 5-9), indicating that the 5' termini of the siRNA had been phosphorylated in vivo.

Third, only the antisense strand is recovered by biotin pull out assays. siRNA duplexes were 5'-end labeled with $^{32}$P by T4 PNK, heat denatured (10 min at 95° C.), and analyzed on a polyacrylamide-7M urea denaturing gel. As shown in FIG. 5 (lane 3), two single-stranded RNA species corresponding to the sense and biotinylated-antisense strands were observed indicating that the siRNA duplexes were fully denatured under these conditions. Denatured siRNA duplexes contained≈equal molar amounts of the sense and the antisense strands of RNA (FIG. 5, lane 3). The cells were transfected with duplex siRNA but the major products of the isolated siRNA (FIG. 5, lanes 5-9) by biotin pull out assay exhibited electrophoretic mobilities identical to the antisense strand (lane 3), indicating that only biotinylated antisense strands were being recovered. These results suggest that RISC melts the duplex siRNA and separates the antisense from the sense strand during RNA interference in vivo.

Example VII: Complete Unwinding of siRNA Duplex is not Necessary for RNA Interference Pathway In Vivo ATP-dependent unwinding of the siRNA duplex in the RISC has been proposed to activate the complex to generate RISC*, which is competent to mediate RNAi (Nykanen et al., 2001). Although unwinding of siRNA in *Drosophila* embryo lysates has been demonstrated in the presence of ATP, the efficiency of unwinding seems low since only 5% of unwound siRNA was detected (Nykanen et al., 2001).

Figures 6A, 6B:
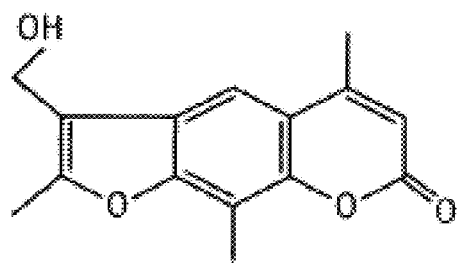
FIG. 6A-E depicts RNA interference activities of covalently photocross-linked duplex RNA in HeLa cells. (A) Structure of a psoralen derivative, 4'-hydroxymethyl-4,5',8-trimethylpsoralen (HMT), used to cross-link the duplex RNA. (B) Photocross-linking sites in GFP siRNA. Three preferred sites for psoralen addition to a duplex RNA are shown by cyan letters with red bars indicating the C-U cross-links formed by UV irradiation in the presence of HMT. (C) Psoralen photocross-linking of siRNA duplexes. Mixtures of siRNA duplex and psoralen were exposed to UV 360 nm and denatured. Cross-linked and noncross-linked siRNAs were resolved on 20% PAGE containing 7 M urea (lanes 2 and 3). UV-irradiated RNA bands were excised from the gel and purified. Purified cross-linked dsRNA (ds-XL) and noncross-linked dsRNA (ds*) are shown in lanes 6 and 5, respectively. To confirm the nature and purity of the cross-link, a portion of the 360 nm UV-irradiated sample (lane 3) was UV-irradiated at 254 nm. Photoreversal of psoralen cross-linked siRNA resulted in products with similar electrophoretic mobility to the siRNA duplex without HMT treatment (lane 4). (D) Fluorescence images showing RNA interference effects of psoralen photocross-linked siRNAs in living HeLa cells. Purified cross-linked ds siRNA (ds-XL, bottom panels) was cotransfected with reporter pEGFP-C1 and control pDsRed1-N1 plasmids into HeLa cells for dual fluorescence reporter assays. Fluorescence (left panels) and phase contrast (right panels) images of living cells were taken 48 hours post transfection. For comparison, images from noncross-linked ds siRNA (ds*, middle panels) and antisense siRNA (as, top panels) are also shown. (E) GFP emission spectra of psoralen photocross-linked siRNA duplex-treated cells. Cell lysates were prepared from HeLa cells treated with antisense siRNA (as), unmodified UV-irradiated duplex siRNA (ds*) and cross-linked ds siRNA (ds-XL) and analyzed by fluorescence spectroscopy. Fluorescence emission spectra of GFP and RFP were detected by exciting at 488 nm and 568 nm, respectively. GFP emission spectra are shown normalized to RFP expression.

To examine whether or not the siRNA duplex in human cells is completely unwound, RNA interference experiments were performed with siRNA duplexes covalently cross-linked by psoralen photochemistry. Psoralens are bifunctional furocoumarins that intercalate between the base pairs of double-stranded nucleic acids and can photoreact with pyrimidine bases to form monoadducts and cross-links (for review see (Cimino et al., 1985)). The structure of the psoralen derivative, 4'-(hydroxymethyl)-4,5',8-trimethylpsoralen (HMT) used in this study is shown in FIG. 6A. Psoralen cross-linking involves two successive photochemical reactions that take place at the 3,4 or 4',5' double bonds of psoralen (Cimino et al., 1985). Upon long wave UV irradiation (320-400 nm), the intercalated psoralen can photoreact with adjacent pyrimidine bases to form either furan-side or pyrone-side monoadducts, which are linked to only one strand of the helix (Cimino et al., 1985). By absorbing a second photon, the furan-side monoadducts can be driven into diadducts, which are covalently linked to both strands of the helix (Hearst et al., 1984; Kanne et al., 1982). Psoralen cross-link formation occurs only when psoralen adds to adjacent and opposite pyrimidine bases in the double helix. The reaction is primarily with uracil in native RNAs, but reactions with cytidine have also been reported (Lipson et al., 1988; Thompson and Hearst, 1983; Turner and Noller, 1983). Based on psoralen photoreactivity, three possible psoralen cross-link sites in the GFP siRNA duplex are shown in FIG. 6B. Note that there is no chance for all three sites to be cross-linked in one RNA.

Figure 6C:
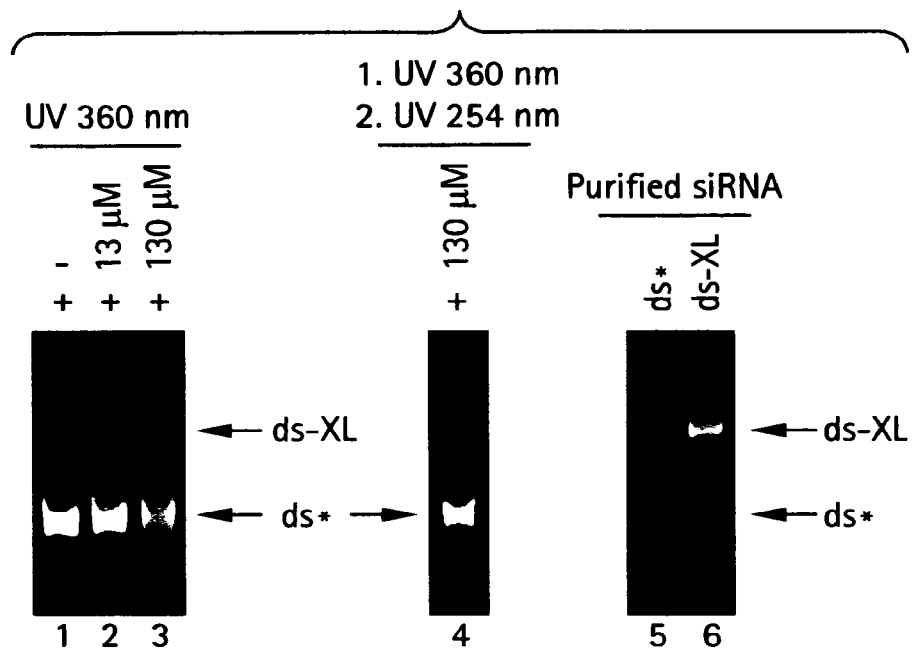
Figure 6D:
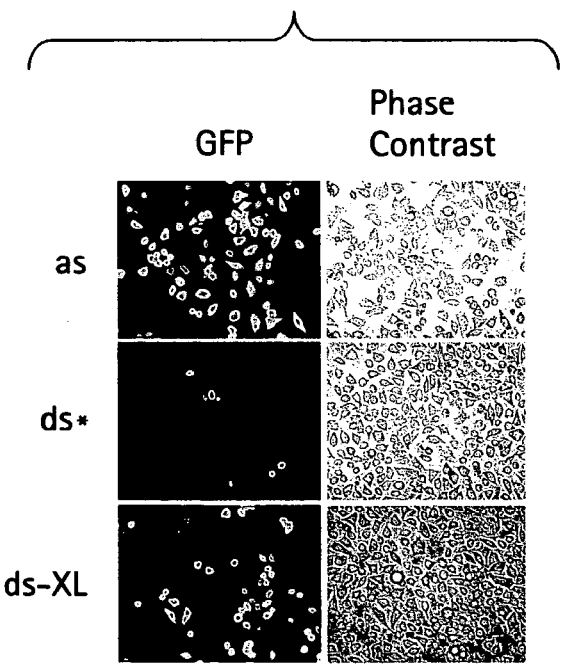
Figure 6E:
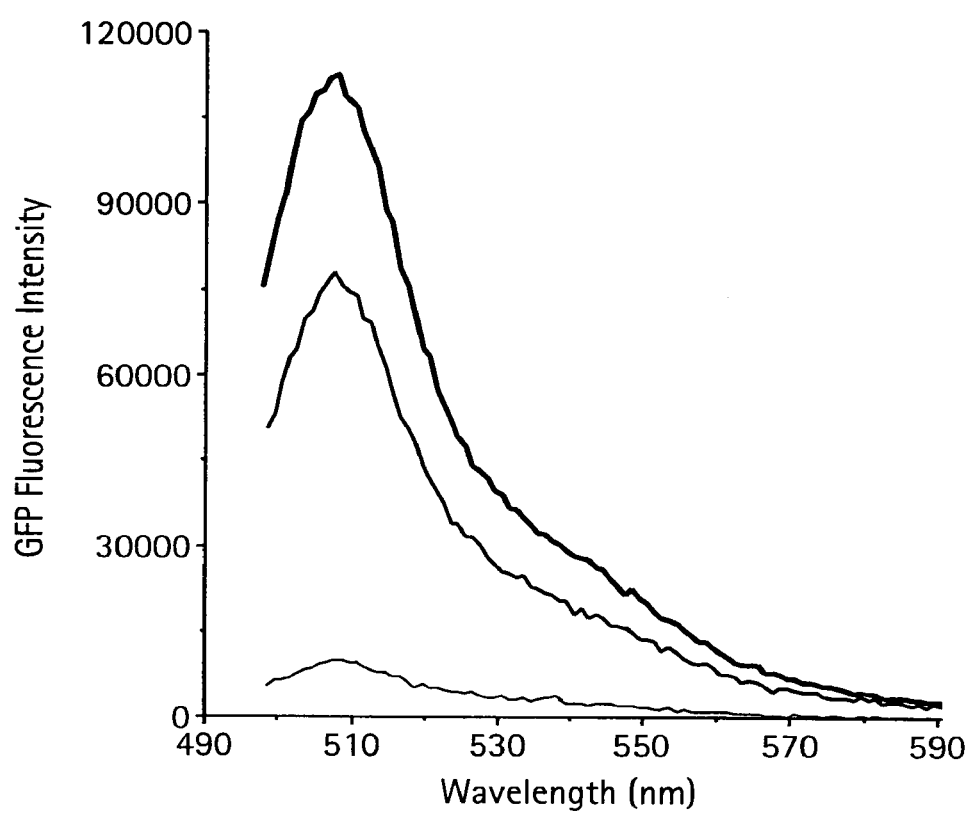

Unlike the noncross-linked ds siRNA, the two strands of the cross-linked siRNA duplex couldn't separate from each other under denaturing conditions so that the cross-linked siRNA duplex showed characteristically retarded mobility in polyacrylamide gel electrophoresis (PAGE) containing 7M urea (FIG. 6C). Cross-linking efficiency depended on the psoralen concentration (FIG. 6C, lanes 2 and 3). To further verify the presence of cross-links in the RNA helix and rule out the possibility of only monoadduct formation, the psoralen cross-links were irradiated with short wave UV (254 nm), which showed photoreversal of the cross-linked bonds (FIG. 6C, lane 4). The cross-linked siRNA duplex (FIG. 6C, lane 3, upper band) was excised from the gel and purified. As control, the noncross-linked siRNA that was irradiated with long wave UV (360 nm) (FIG. 6C, lane 3, lower band) was also purified by the same method. The structures of the purified noncross-linked and psoralen cross-linked siRNA duplexes were confirmed by PAGE containing 7M urea (FIG. 6C, lanes 5 and 6). Fluorescence imaging of living cells treated with cross-linked siRNA duplex showed that the siRNA duplex's inability to separate on PAGE did not completely abolish its RNA interference activity (FIG. 6D, ds-XL). Quantitative analysis of GFP fluorescence intensity indicated that cross-linked siRNA retained 30% of its RNAi activity (FIG. 6E, blue line). These results demonstrate that a complete unwinding of the siRNA duplex is not required for gene silencing in vivo (see Discussion).

There is a possibility that the psoralen cross-link of RNA can be photoreversed during transfection, repaired or removed by some unknown mechanism inside the cells, which might cause the partial RNA interference effect in vivo observed in FIGS. 6D and 6E. To rule out this possibility, a psoralen cross-linking experiment was performed with siRNA duplex containing biotin at the 3' end of the antisense strand. The cross-linked duplex (ss/as3'-Biotin-XL) was isolated and purified as described above and transfected into HeLa cells by lipofectamine. Biotinylated siRNA was isolated from the cells 30 h post transfection by biotin pull out assay, SAP treated and $^{32}$P-labeled by T4 PNK as described above. The biotinylated siRNA was still cross-linked (FIG. 7, lane 7) at 30 h post transfection. When UV-irradiated (254 nm), this higher molecular weight siRNA species was converted into two RNA species corresponding to sense and antisense strands (FIG. 7, lane 8), indicating the reversibility of the psoralen cross-link. These results show that cross-linked siRNA duplexes can enter the RNAi pathway.

Summary of Examples I-VII

By using a quantitative dual fluorescence-based system, the kinetics and a number of important parameters involved in the RNAi pathway have been dissected in cultured human cells. The results presented in Examples I-VII highlight the role of free 5' end hydroxyl groups and the requirement of an A-form helical structure between the antisense strand and the target mRNA. It was also found that a complete unwinding of the siRNA helix is not necessary to cause RNAi effects in vivo.

The time-dependent effect of siRNA may reflect a time lag between target mRNA degradation and the half-life of the existing protein expressed from the target gene. This time dependence may also indicate that the siRNAs need to be processed or assembled into an active complex with cellular factors for effective RNA interference.

Although RNA interference lasted at least 66 hours in HeLa cells, quantitative analysis indicated that inhibition by siRNAs did not persist. After reaching maximal activity at 42 hours post transfection, RNA interference started to decrease at 54 hours, with only 70% inhibition activity at 66 hours. It was also found that 5-10% protein expressed from the genes targeted by siRNA remained at 42 hours post transfection, but protein amount showed gradual recovery to normal levels between 66 to 90 hours (3 to 4 days) post transfection (Chiu and Rana, unpublished results). The recovery of target gene expression also indicates that RNA interference by exogenous siRNA duplex does not exist forever in mammalian cells. These findings suggest that the proposed amplification system driven by RdRP and present in plants and nematodes may not exist or has very little effect on siRNA-mediated gene silencing in mammalian cells.

Recent studies have shown that synthetic siRNAs containing 5'-OH termini can successfully induce RNAi effects in *Drosophila* embryo lysates (Elbashir et al., 2001c; Nykanen et al., 2001) and cultured mammalian cells (Elbashir et al., 2001a). A model involving a 5' end kinase activity necessary for RNA interference has been proposed (Nykanen et al., 2001). However, there is no evidence that the 5' end hydroxyl is required for in vivo interference activity. The above results show that replacing the 5' OH, a kinase target site, with amino groups inhibited RNAi activity. Further isolation of siRNA by biotin pull out experiments revealed that prior phosphatase activity was required for in vitro 5' end radiolabeling by a polynucleotide kinase. Taken together, these results provide strong evidence for the requirement of 5' end kinase activity for RNA interference effects in vivo.

What about a free 3' end for RNAi effects in vivo? An RNA-directed RNA polymerase (RdRP) chain reaction, primed by siRNA, has recently been proposed to amplify the interference effects of a small amount of trigger RNA (reviewed in (Nishikura, 2001)). Lipardi et al. (Lipardi et al., 2001) have shown siRNA-primed RNA synthesis in *Drosophila* embryo lysates and suggested that RNAi in *Drosophila* involves an RdRP where siRNA primes the conversion of target RNA to dsRNA. Further evidence of RdRP involvement in the RNAi pathway in *C. elegans* has been provided in studies (Sijen et al., 2001) showing target RNA-templated synthesis of new dsRNA. These studies highlight the importance of a 3' hydroxyl in priming subsequent RdRP reactions. An RdRP homolog has not yet been identified in the human genome, suggesting the presence of a separate enzyme that can carry out primer-dependent replication of an RNA template. The above results demonstrate that blocking the 3' position did not significantly affect RNAi activity of siRNA in human cells. Results of kinetic experiments show that the interference effect lasted only ~4 days, indicating the absence of an amplification mechanism in human cells. In addition, our biotin pull out experiments show that the 3' end biotin groups on the antisense strand were not efficiently removed during RNAi activities in HeLa cells. Based on these studies, a model is proposed where RNA amplification by RNA-dependent RNA polymerase is not essential for RNA interference in mammalian cell lines.

It is interesting to note that there was no requirement for a perfect A-form helix in siRNA for interference effects in HeLa cells, but an A-form structure was required for antisense-target RNA duplexes. These results suggest an RNAi mechanism where RISC formation does not involve perfect RNA helix recognition, but RISC* (the asterisk indicates the active conformation of the complex) assembly requires an A-form helical structure.

The most intriguing results were obtained by cross-linking siRNAs and testing their interference activities in HeLa cells. Psoralen cross-linked siRNA duplexes retained 30% of RNA interference activity. This result can be explained by psoralen photocross-linking chemistry. There are three possible sites in the GFP siRNA duplex where psoralen can cross-link, yet the cross-linking reaction is not efficient enough to create multiple cross-links in a single given siRNA duplex (Cimino et al., 1985; Thompson and Hearst, 1983). Thus, in the purified cross-linked siRNA duplex population, about ⅓ had cross-linking at the site near the 5' end of the antisense strand, about ⅓ had cross-linking in the middle region and the rest had cross-linking near the 3' end of the antisense strand.

It has previously been shown that accessibility to the 5' termini of the antisense strand is required for efficient RNA interference in vivo. 5' phosphorylation of the antisense strand is also required for RNA interference in vitro (Nykanen et al., 2001). The cleavage site on target mRNA has been shown to be determined by the 5' end position of the target-recognizing siRNA (Elbashir et al., 2001c). Based on these findings, it is suggested that unwinding of the siRNA duplex would start from the 5' end of the antisense strand, which sets the ruler for target mRNA cleavage. If cross-linking occurred near the 5' end of the antisense strand, it would completely prohibit the unwinding of the siRNA duplex and block access to the 5' termini of the antisense strand, which would completely abolish the RNAi effect. If cross-linking occurred in the middle of siRNA duplex, near the cleavage site of mRNA, it is suggested that although the siRNA duplex could still undergo some unwinding, this cross-link might interfere with the pairing between target mRNA and the guiding siRNA, thus also blocking the RNAi effect. If cross-linking occurred near the 3' end of the antisense strand, the duplex RNA could unwind, not completely but sufficient for the antisense strand to hybridize to the target mRNA. It has previously been shown that blocking either the 3' end of the antisense strand or the 5' end of the sense strand has no significant effect on its RNAi activity. It would thus be reasonable to believe that a siRNA duplex with cross-linking near the 3' end of the antisense strand may still be competent in RNA interference. This hypothesis also explains the remaining 30% RNAi activity in the psoralen-cross-linked siRNA duplex.

These results suggest a possible model for the RNAi pathway in human cells. An RNA-protein complex containing siRNA (RISC) is assembled without the requirement for an A-form RNA helix and/or a free 3'-OH. The 5'-OH of the siRNA duplex is phophorylated by a kinase. During activation of RISC to RISC*, a 5'43' helicase unwinds the RNA duplex to allow hybridization between the antisense strand of siRNA and the target RNA. The requirement of a perfect A-form helix at this stage strongly suggests that another protein (or protein complex) binds this RNA duplex, either in a structural role and/or assisting in the cleavage of mRNA. A complete unwinding of the siRNA duplex is not required for this process, nor can this interference activity be amplified via the 3' end. However, unwinding of the duplex up to the cleavage site may be necessary so that the antisense strand can form an A-form helix with the target strand for further protein interactions. These results also argue against the involvement of RNA amplification mechanism(s) for RNA interference in human cells.

In summary, the above results provide new insight into the mechanism of RNAi in mammalian cells, and guide the design of siRNA structures useful in probing biological questions and in functional genomic studies.

Figure 8A:
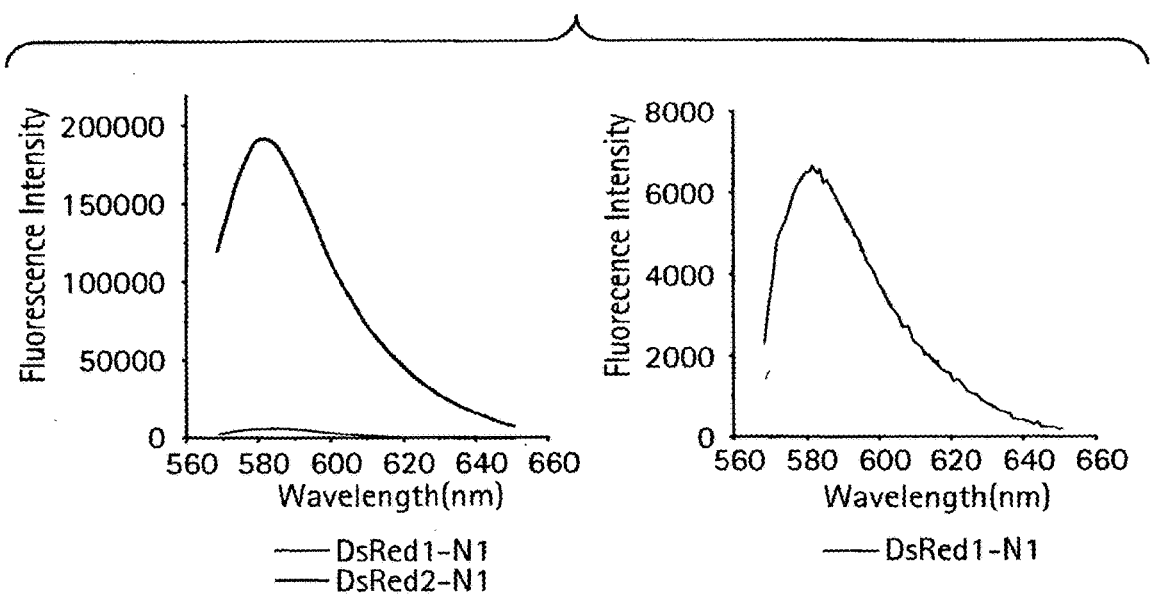
FIG. 8A-B depicts fluorescence intensity spectra for extracts of cells transfected with various GFP- and/or RFP-encoding plasmids and, optionally, treated with siRNAs targeting GFP and/or RFP mRNAs. (A) depicts the fluorescence intensity spectra for extracts from cells transfected with dsRed1-N1 versus dsRed2-N1. (B) depicts RNAi of GFP or RFP, left and right panels, respectively.
Figure 8B:
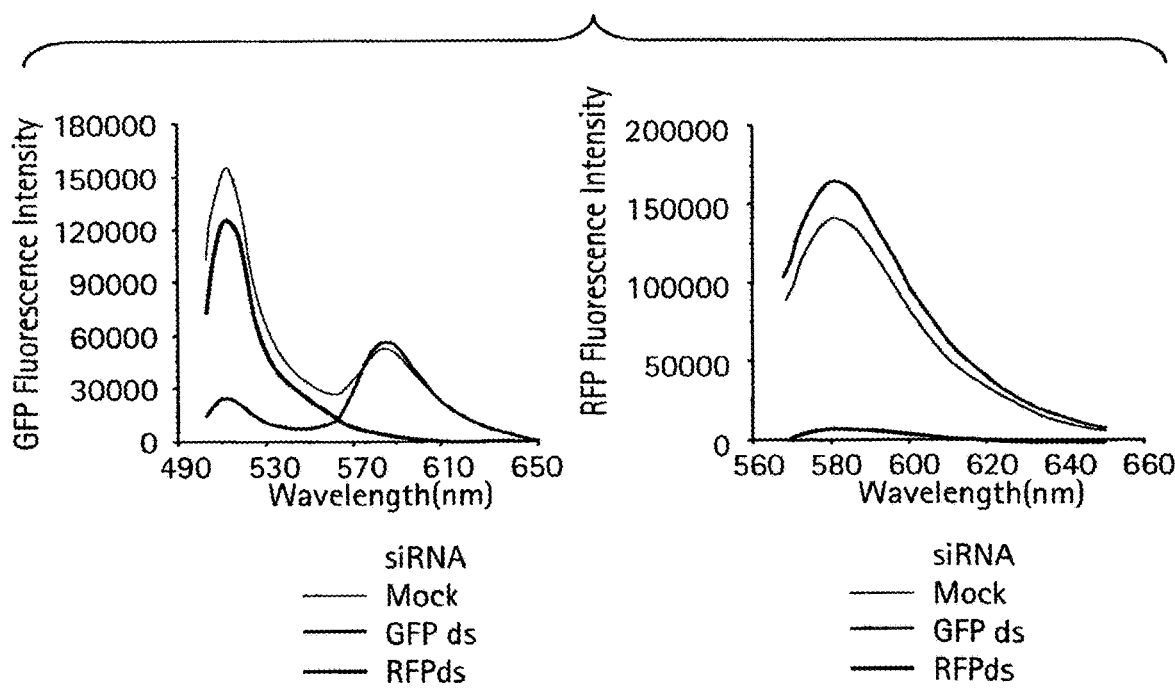

Example VIII: Improved Dual Fluorescence Assay pDsRed2-N1 (Catalog #6973-1, BD Biosciences Clontech, Palo Alto, Calif.) encodes DeRed2, a DsRed variant that has been engineered for faster maturation and lower non-specific aggregation. DsRed2, derived form it progenitor DeRed1, contains six amino acid substitutions: A105V, I161T and S197A, which result in the more rapid appearance of red fluorescence in transfected cell lines and R2A, K5E and K9T, which prevent the protein from aggregation. The extinction coefficient of DsRed2 is 43800 (M−1 cm−1) and the quantum yield is 0.55, both are showing significantly increasing compared to DsRed1. Intensity of red fluorescence in cells transfected with pDeRed1 and pDeRed2 is shown in FIG. 8A, siRNA targeting DsRed1-N1 can also targeting DeRed2-N1 mRNA because the sequence are identical in the targeting region of siRNA.

In an improved dual fluorescence reporter assay, EGFP-C1 encoded enhanced green fluorescence protein (GFP), while DsRed2-N1 encoded red fluorescence protein (RFP2) as described above. Using lipofectamine, HeLa cells were cotransfected with pEGFP-C1 and pDsRed2-N1 expression plasmids and siRNA duplex, targeting either GFP or RFP. To quantify RNAi effects, lysates were prepared from siRNA duplex-treated cells at 42 hr posttransfection. GFP and RFP fluorescence in clear lysates was measured on a fluorescence spectrophotometer. The peak at 507 nm (FIG. 8B, left panel) represents the fluorescence intensity of GFP, and the peak at 583 nm (FIG. 8B, right panel) represents the fluorescence intensity of RFP. GFP fluorescence intensity of GFP ds-treated cells (FIG. 8B, left panel, green line) was only 5% of mock-treated (black line) or RFP ds-treated cells (blue line). In contrast to GFP fluorescence, RFP fluorescence intensity (FIG. 8B, right panel) significantly decreased only in cells treated with RFP ds (red line), indicating the specificity of the RNAi effect.

Thus, by using the DsRed2-N1 plasmid for encoding RFP, a much higher signal-to-noise ration is achieved (i.e., a 10 to 20-fold increase in signal when comparing DsRed1-N1 and DsRed2-N1). Moreover, use of the DsRed2-N1 plasmid results in similar fluorescent intensities for RFP as those seen for cells transfected with EGFP-C1 (i.e., GFP intensities) making comparison in the dual fluorescence assay more practicable.

Figure 9A:
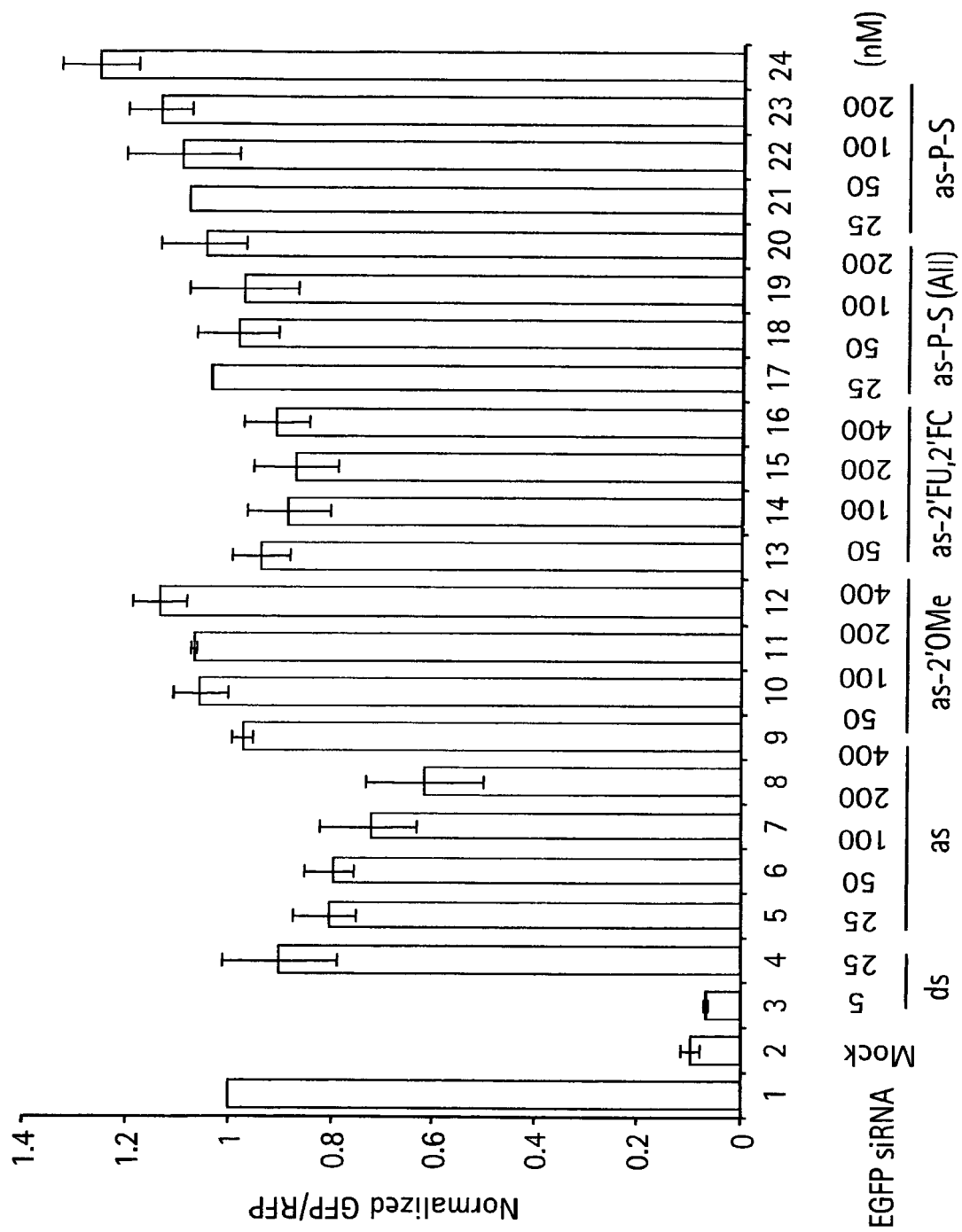
FIG. 9A-B depicts a quantitative analysis of RNAi effects in HeLa cells transfected with modified single-stranded (antisense strand) siRNAs. (A) depicts the fluorescence intensity ratio of target (GFP) to control (RFP) fluorophore. (B) depicts the fluorescence intensity ratio of target (GFP) to control (RFP) fluorophore in the presence of various amount of 5'-phosphorylated as siRNA.

Example IX: Quantitative Analysis of RNAi Effects in HeLa Cells Transfected with Modified Single-Stranded (Antisense Strand) siRNAs pEGFP-C1 (as reporter), pDsRed2-N1 (as control) plasmids and various amount of antisense strand siRNA (as) were cotransfected into HeLa cells by lipofectamine. Cells were harvested at 42 h after transfection. Fluorescence Intensity of GFP and RFP in total cell lysates were detected by exciting at 488 and 568 nm, respectively. The fluorescence intensity ratio of target (GFP) to control (RFP) fluorophore was determined. The data are set forth in FIG. 9A. Modified siRNAs were as follows: 2'-O-Methyl-modified as siRNAs (as-2'-Ome, lanes 9-12), 2'-Fluoro U and C modified as siRNAs (as-2'FU, 2'FC, lanes 13-16), as siRNAs with phosphorothiolates modification at backbone residues (as-P—S-All, anes 17-20) and as siRNAs with phosphorothiolates modification at all backbone residues except the bases 9-12 (as-P-S, lanes 21-24). The intensity ratios of GFP to RFP in various treatment were normalized to the ratio observed in the mock treated cells. A normalized ratio of less than 1.0 indicates a specific RNA interference effect. For comparison, results from unmodified antisense RNA (as, lanes 4-7) and duplex siRNA (ds, lane 2-3)-treated cells are included. These data show that single stranded siRNA has much lower efficiency than duplex siRNA in mediating RNAi.

Figure 9B:
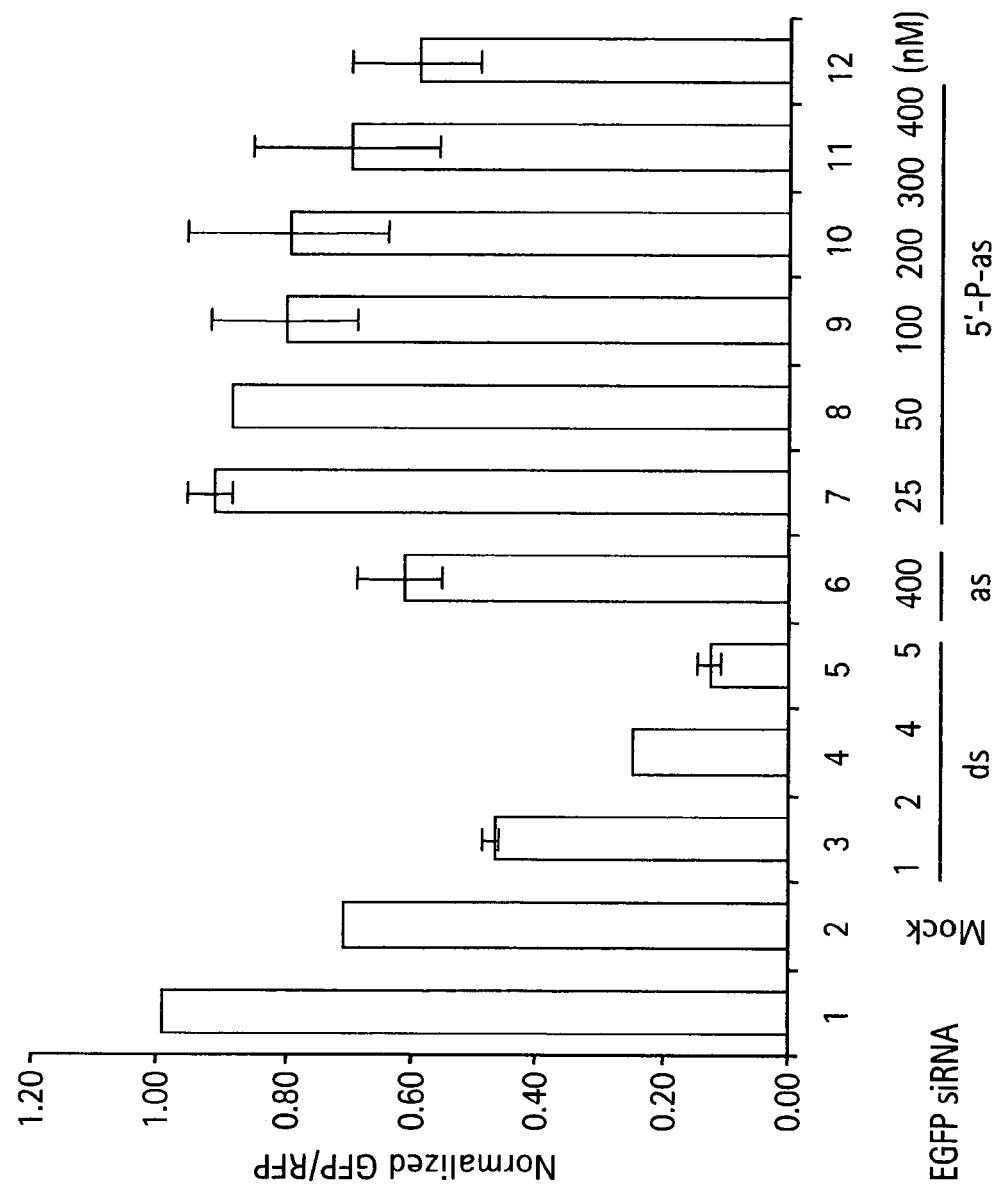

Single stranded RNA corresponding to the GFP antisense sequence with 5'-phosphate group was synthesized and purified according to art-recognized methodologies. The fluorescence intensity ratio of target (GFP) to control (RFP) fluorophore was determined (FIG. 9B) in the presence of various amount of 5'-phosphorylated as siRNA (5'-P-as, lanes 7-12). For comparison, results from unmodified antisense RNA (as, 400 nM, lane 6) and duplex siRNA (ds, lane 2-5)-treated cells are included. These data show that phosphorylation of single-stranded siRNA (antisense strand) does not much improve its RNA interference activity.

Example X: Quantitative Analysis of RNAi Effects in HeLa Cells Transfected with Modified Duplex siRNAs Results set forth in Example II showed that RNAi effects typically peaked between 42-54 h post transfection and targeted gene expression started to be restored by 66 h post transfection. To determine if the duration of RNAi could be prolonged by increasing the half life of siRNAs, various chemical modifications were made to nucleotides that affected siRNA stability. These modified siRNAs were then tested in an improved dual fluorescence reporter assay which was set forth in Example VIII. The sequence of EGFP siRNA and EGFP mRNA, the specific mRNA cleavage site, plus the structures of the chemically modified nucleotides are diagrammed in FIG. 1. The specific chemical modifications, the particular siRNA strand(s) where modifications were made, and the effect of the chemically modified siRNA on RNAi activity are summarized in Table 1. RNAi activity of siRNAs was evaluated with eight different siRNA concentrations (ranging from 1-200 nM). Each experiment was completed in duplicate and repeated twice.

pEGFP-C1 (as reporter), pDsRed2-N1 (as control) plasmids and various amount of modified siRNA were cotransfected into HeLa cells by lipofectamine. Cells were harvested at 42 h after transfection. Fluorescence intensity of GFP and RFP in total cell lysates were detected by exciting at 488 and 568 nm, respectively. The fluorescence intensity ratio of target (GFP) to control (RFP) fluorophore was determined in the presence of modified siRNAs and normalized to the ratio observed in the mock treated cells. A normalized ratio of less than 1.0 indicates a specific RNA interference effect. Data are presented in FIG. 10. For comparison, results from unmodified duplex siRNA (ds, lane 2-5)-treated cells are included in each panel. Unless otherwise indicated, all residues are modified.

FIG. 10A depicts the results from cells treated with duplex siRNA with 2'-Deoxy modification at internal residues within the sense strand (ss-2'Deoxy/as, lanes 6-11).

Figure 10B:
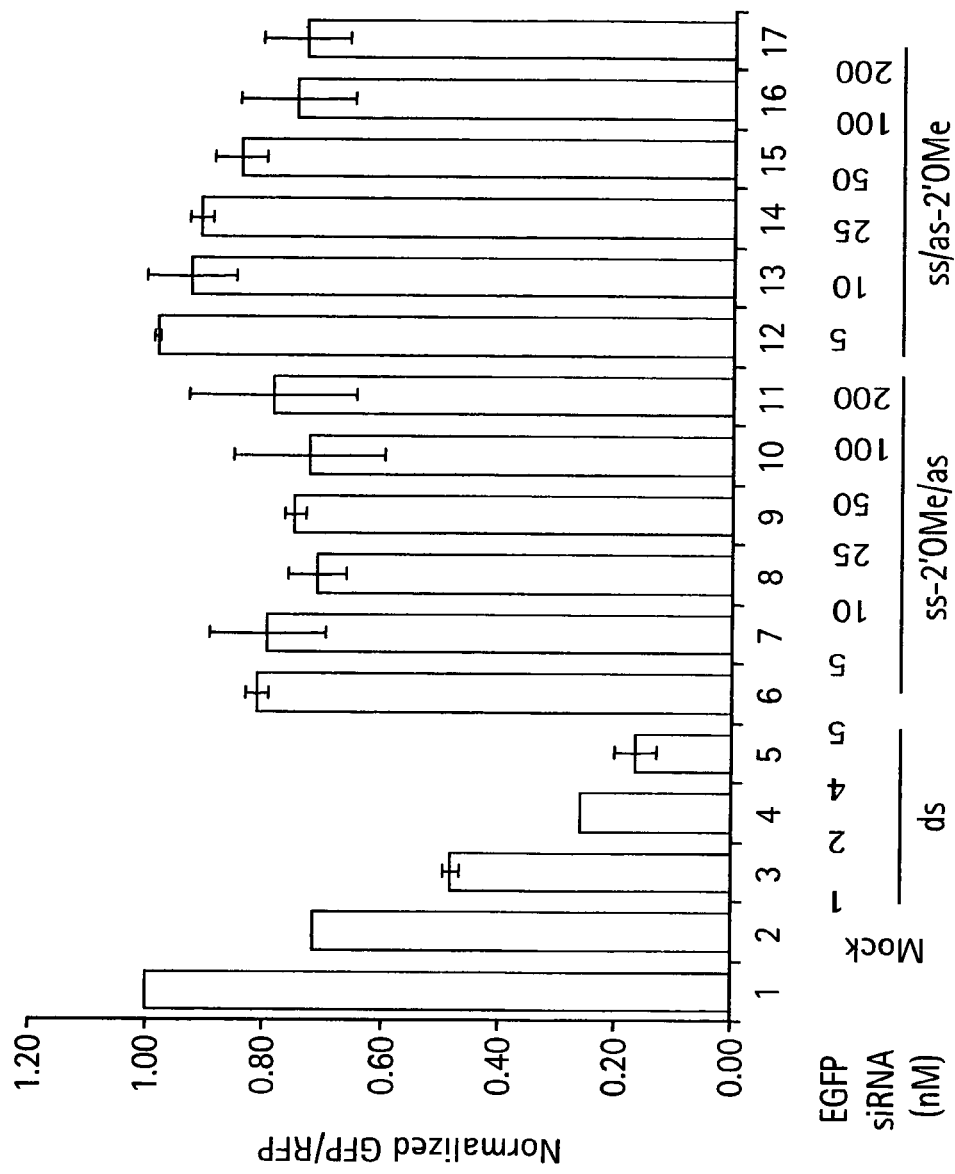
Figure 10C:
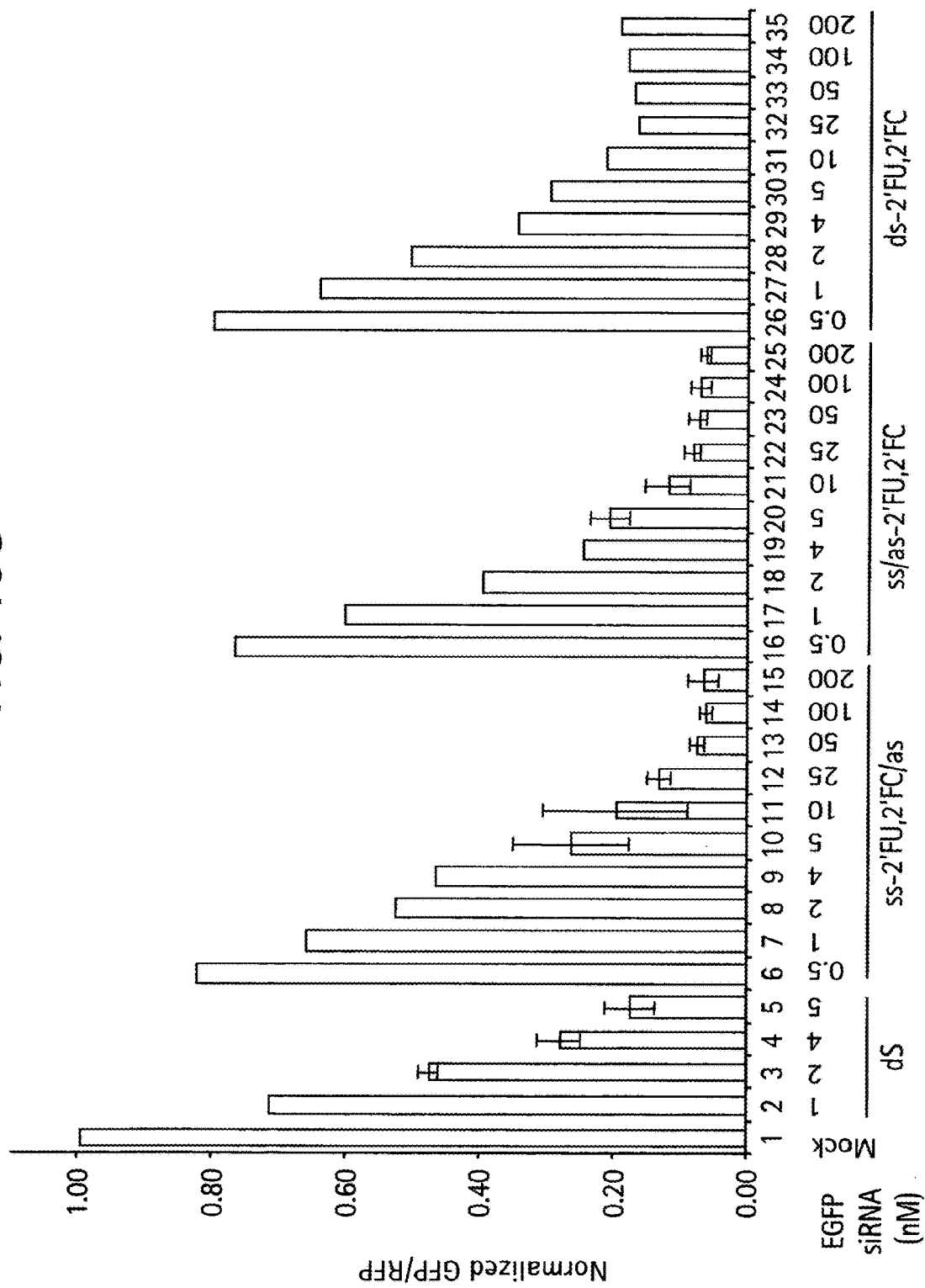
Figure 19A:
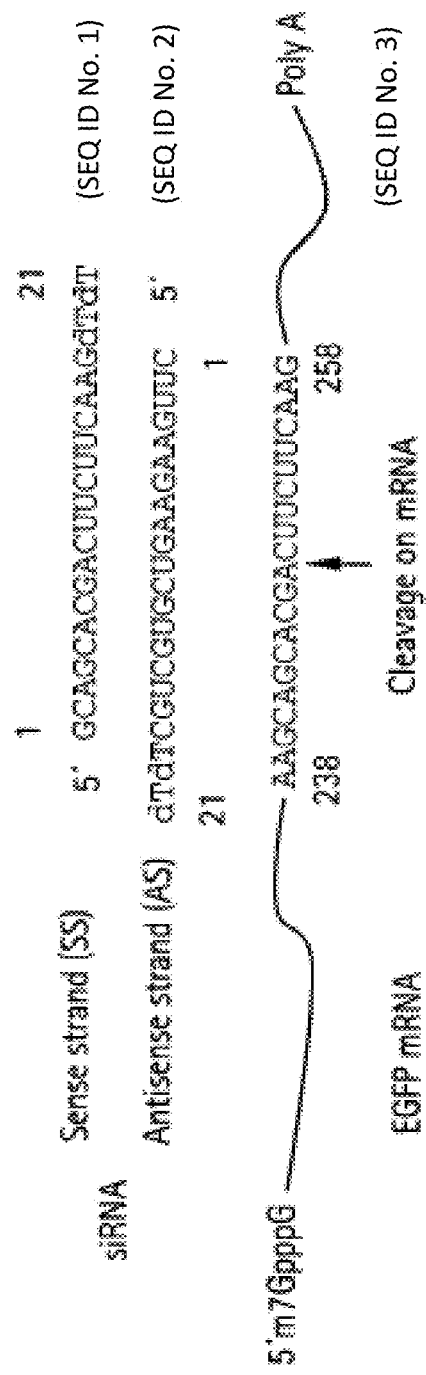
FIG. 19A-B depicts the structures of EGFP siRNA and the structure and nomenclature of preferred chemical modifications. (A) depicts the structures of EGFP siRNA. (B) depicts the structure and nomenclature of preferred chemical modifications.
Figure 19B:
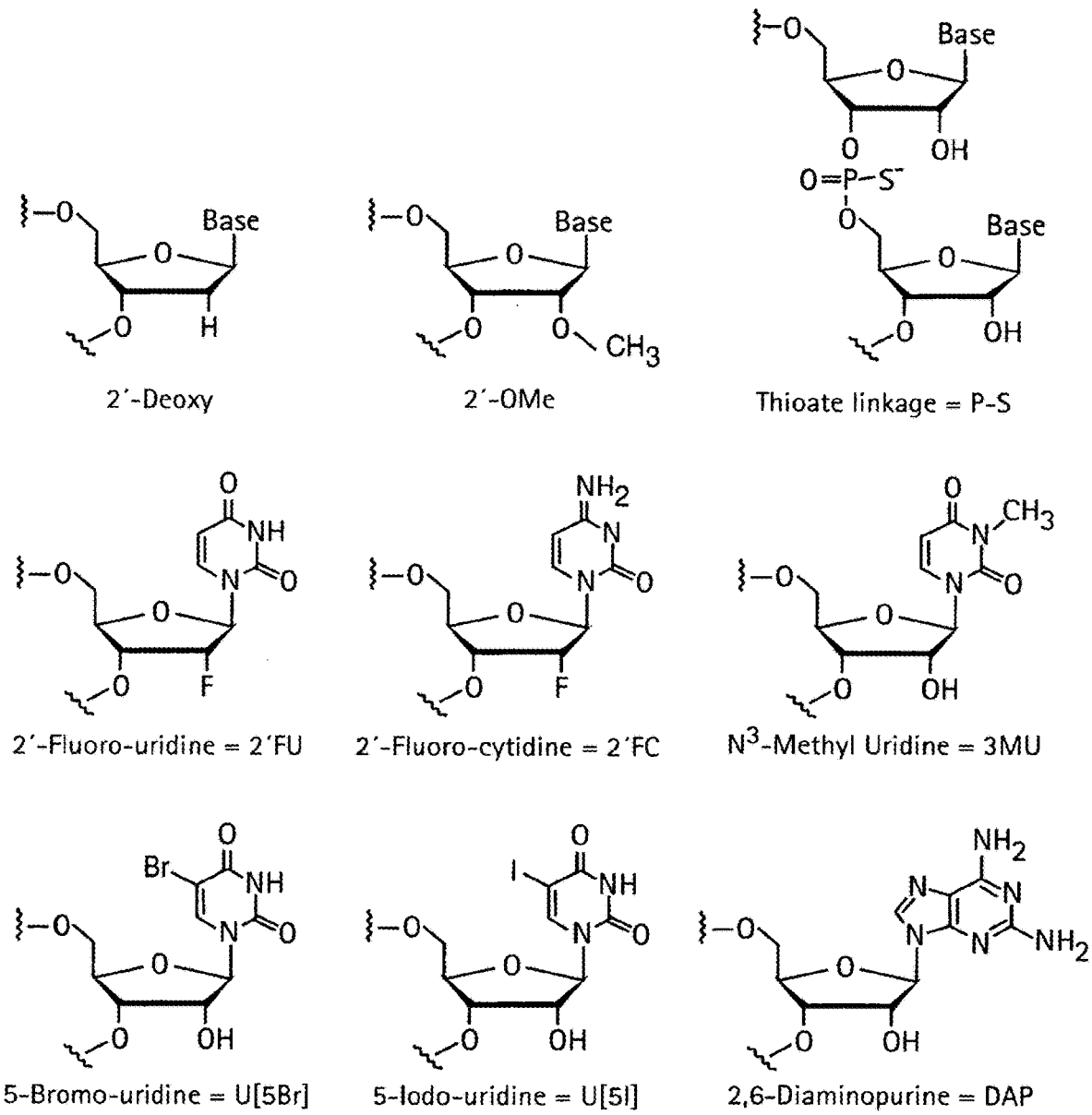

An interesting result was seen by modifying the 2'OH to a bulky methyl group to create 2'OMe nucleotides that were incorporated into sense, antisense or both strands of EGFP siRNAs (FIG. 19). This modification was hypothesized to improve RNAi efficacy because 2'OMe groups are thought to increase RNA stability by inducing an altered RNA conformation that is more resistant to nucleases (Cummins et al., 1995). This modification is also thought to increase RNA affinity for RNA targets and improve hybridization kinetics (Majlessi et al., 1998). FIG. 10B depicts results from cells treated with duplex siRNA with 2'-O-Methyl modification at internal residues within the sense strand (ss-2'Ome/as, lanes 6-11) or the antisense strand (ss/as-2'-Ome, lanes 12-17). Despite the potential benefits, 2'OMe nucleotides incorporated into either the sense or antisense strand greatly diminished EGFP gene silencing to ~25% or ~16%, respectively, while double-stranded 2'OMe modified siRNAs completely abolished RNAi (FIG. 10B and Table 1, rows 12-14). These results suggested that the methyl group, as a bulky group, may severely limit the interactions between siRNAs, target mRNAs and the RNAi machinery required for successfully mediating RNAi. It is worth noting that since the bulkiness of the methyl group would likely be the cause of decreased RNAi activity rather than the actual lack of the 2'OH specifically, these studies still supported the conclusion that the 2'OH was not required for RNAi. The effects of modifying the 2'OH of nucleotides on RNAi were next studied by replacing uridine and cytidine in the antisense strand of siRNA with 2'-Fluoro-uridine (2'-FU) and 2'-Fluoro-cytidine (2'-FC), which have a fluoro-group at the 2' position in place of the 2'OH (FIG. 19). Addition of a 2' fluoro-group should increase the stability of the siRNA by making the siRNAs less recognizable to RNases thereby providing siRNAs protection from degradation. When measured in the dual fluorescence assay, 2'FU, FC siRNAs, modified only in the sense strand (ss-2'FU, 2'-FC/as, FIG. 10C lanes 6-15), only in the antisense strand (ss/as-2'-FU, 2'-FC, FIG. 10C lanes 16-25), or in both strands (ds-2'FU, 2'FC, FIG. 10C lanes 26-35), all showed decreased EGFP fluorescence when normalized to non-targeted RFP fluorescence that was comparable to the normalized decrease seen with wild type siRNAs (FIG. 10C; Table 1, rows 1-4). These results suggested that the 2'OH was not required for RNAi and that nucleotides modified with 2' fluoro-groups could be used in siRNA constructs to successfully induce RNAi-mediated gene silencing.

Figure 10D:
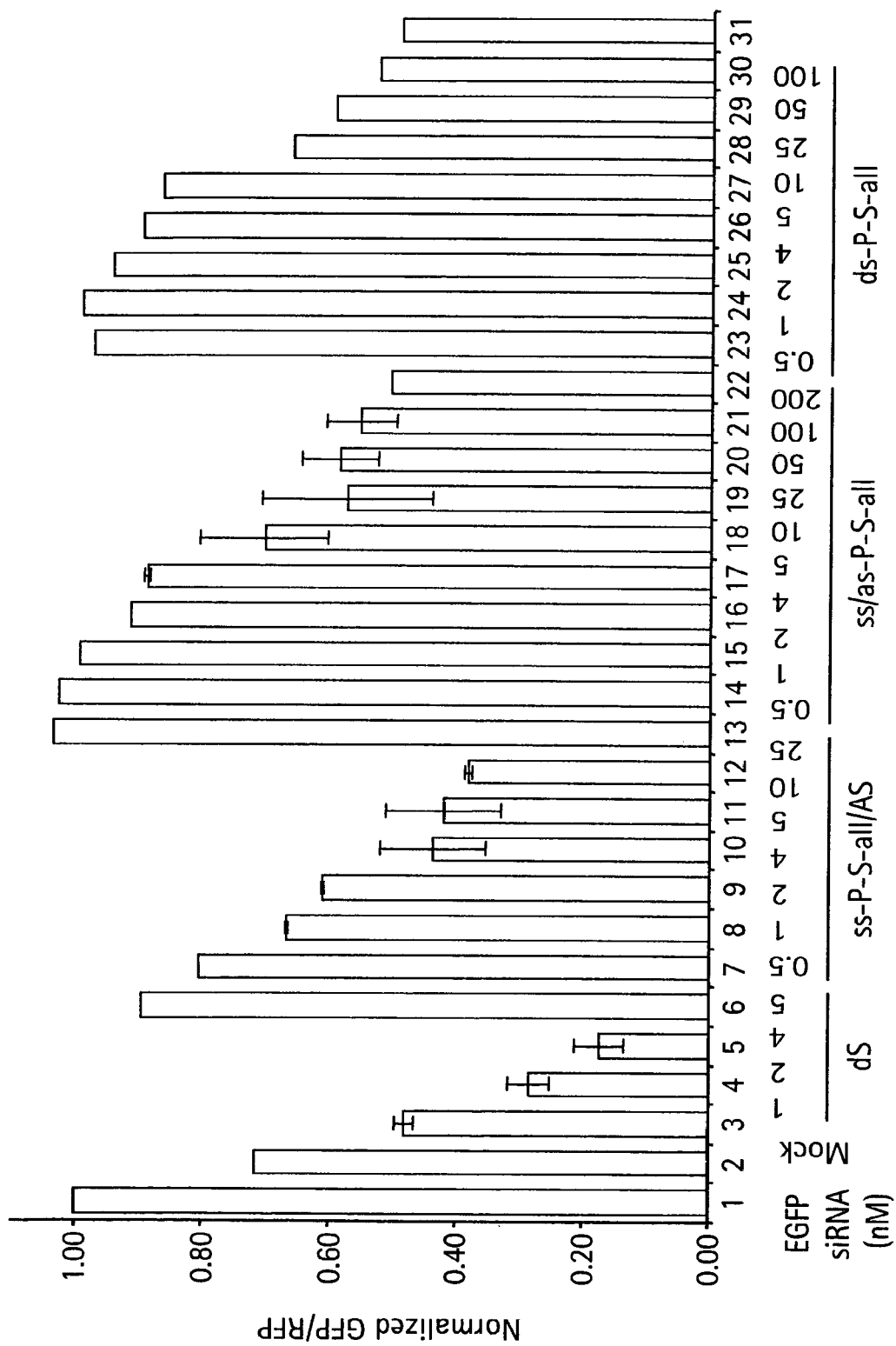
Figure 10E:
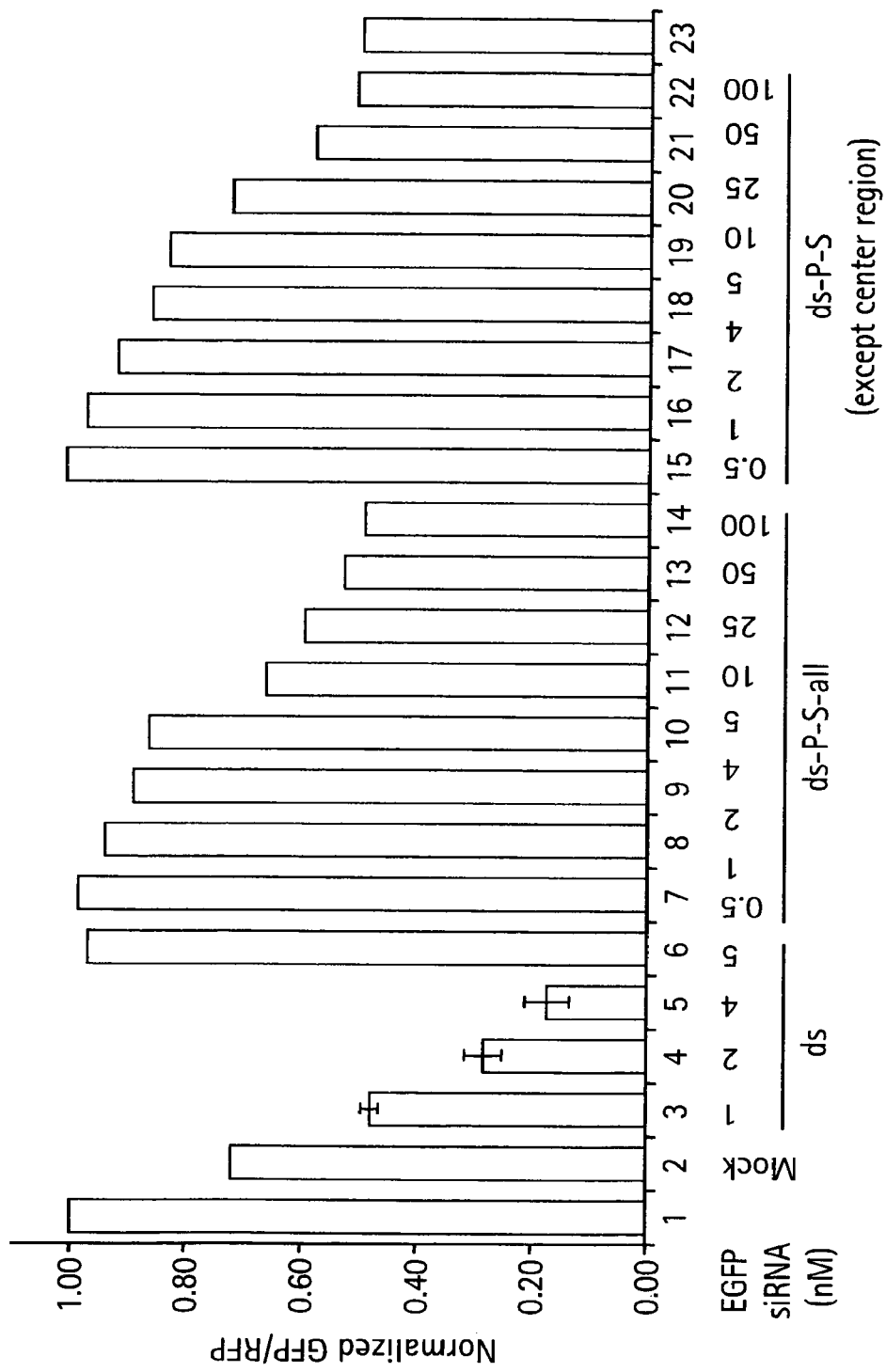

In a final analysis of modifications that may potentially increase siRNA stability without disrupting RNAi potency, a thioate linkage (P-S) was integrated into the backbone of the EGFP siRNA strand(s). P—S linkages were previously used in antisense methodology for increasing resistance to ribonucleases (reviewed in (Stein, 1996)) and therefore, were postulated to enhance the stability of siRNAs. FIG. 10D depicts results from cells treated with duplex siRNA with phosphorothiolate modification at each backbone residue of the sense strand (ss-P-S-all/as, lanes 6-12), antisense strand (ss/as-P-S-all, lanes 13-22) and both strands (ds-P-S-all, lanes 23-31). FIG. 10E depicts results from cells treated with duplex siRNA with phosphorothiolate modification at each backbone residue of both strands except for bases 9-12 of the antisense strand (ds-P-S, except center region, lanes 15-23). For comparison, cells treated with duplex siRNA with phosphorothiolate modification at each backbone residue of both strand (ds-P-S-all) are also shown (lanes 6-14). Incorporating the P-S linkages into the double-stranded siRNA sense strand led to moderate levels of RNAi activity (62% inhibition), while P-S linkages in either the antisense or both strands of the siRNAs led to just less than ~50% RNAi-induced inhibition (Table 1, rows 15-17). These results suggested that the P-S modifications did not prohibit RNAi-mediated degradation and only moderately affected the efficiency of RNAi. Interestingly, incorporating 2'FU, FC modifications into the antisense strand in addition to the added P-S linkages showed lower levels of EGFP gene silencing (Table 1, row 18), indicating that there was a synergistic effect that decreased but did not inhibit RNAi-mediated degradation when both the 2' F groups and the P-S linkages were incorporated into siRNAs.

In summary, these data indicate that 2' Deoxy modifications within the sense strand are well tolerated, whereas 2'-O-Methyl modification is not well tolerated (either within the sense or antisense strand). Moreover, 2'-FU and 2'-FC modifications are well tolerated within either strand or within both strands. Note that siRNA duplexes having every internal U and C modified with 2'F are virtually as efficient at mediating RNAi as are their unmodified counterparts. Also well tolerated are phosphorothioate linkages between backbone residues of the sense and/or antisense strands. Leaving the most internal residues unmodified in duplex siRNA having phosphorothioate linkages between backbone residues of the sense and antisense strands did not significantly improve the RNAi activity.

Example XI: Kinetics of RNAi Effects of Duplex siRNA with 2'-Fluoro Uridine and Cytidine Modification in HeLa Cells Showing Effect of Modified siRNA is Much More Persistent than the Unmodified siRNA To address whether increased stability seen with modified siRNAs prolonged the duration of RNAi in vivo, RNAi, induced by unmodified and 2'FU, FC modified double-stranded EGFP siRNAs, was assayed in the dual fluorescence reporter assay over a period of 120 h (FIG. 11). The fluorescence intensity ratio of target (GFP) to control (RFP) protein was determined in the presence of unmodified double-strand (ds) RNA (blue bars) and duplex siRNA with 2'-Fluoro uridine and cytidine modification (ds-2'FU, 2'FC, cyan bar) and normalized to the ratio observed in the presence of Mock treated cells (red bars). A normalized ratio of less than 1.0 indicates specific RNA interference.

Although 2'FU, FC modified EGFP siRNAs were slower to show RNAi effects by 6-18 h, maximal RNAi effects occurred by 42 h post-transfection for both modified and unmodified siRNAs. The maximal activity for both siRNAs was also in the same range, with both showing ~85-90% inhibition of GFP expression. However, the RNAi effects observed over the period of 66-120 h revealed that the effect of modified siRNAs was much more persistent than unmodified siRNA. By 120 h post-transfection, the effect of modified siRNAs still remained at ~80% inhibition of GFP expression while the effect of unmodified siRNAs had dropped to less than ~40% inhibition. These results strongly indicated that there was a direct link between the duration of the RNAi effects and siRNA stability in human cells. Furthermore, these results showed conclusively that siRNAs stabilized by chemical modifications, like the 2' FU, FC-modifications, can be used to effectively induce and significantly prolong RNAi-mediated gene silencing in vivo.

Example XII: Study of Duplex siRNA Stability in HeLa Cell Lysate

Figure 12C:
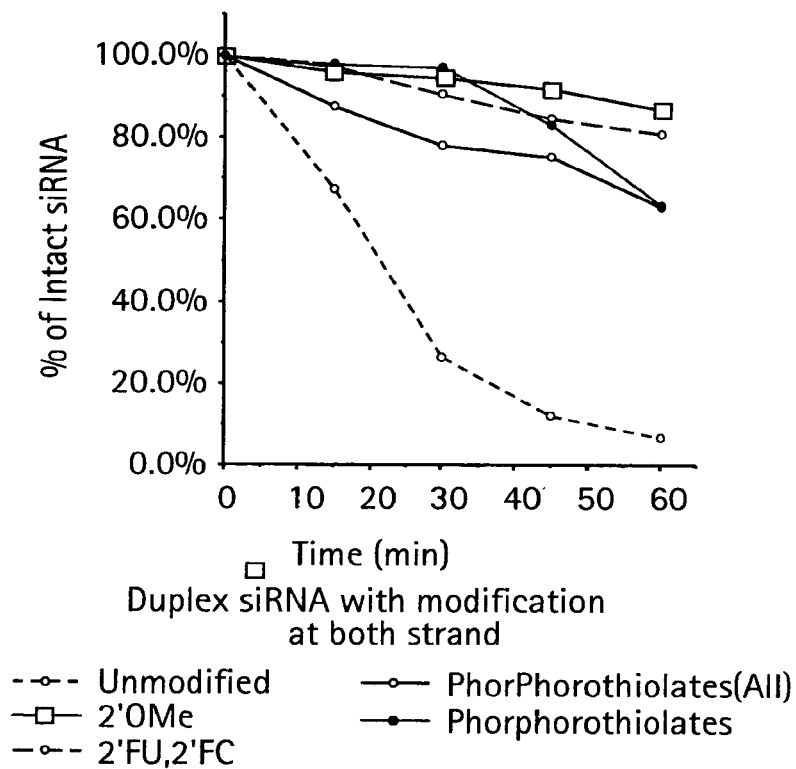

As the data set forth in Example X showed that siRNAs modified with stabilizing 2'-FU, FC groups could effectively mediate RNAi to levels comparable to wild type, it was necessary to show that these modifications did in fact enhance siRNA stability. To measure the stability of siRNA in cell extracts, unmodified or modified EGFP antisense strand siRNA were 5'-labeled with [gamma-$^{32}$P] ATP by T4 polynucleotide kinases. Duplex siRNAs were formed by annealing an equal molar ratio of unmodified or modifed sense strand siRNA with the 5'-$^{32}$P labeled antisense strand. 50 μmole duplex siRNA which labeled at 5' end of the antisense strand were incubated with 500 ug HeLa cytoplasmic extract in 50 ul reaction mixture containing 20 mM Hepes, pH 7.9, 100 mM KCl, 10 mM NaCl, 2 mM MgCl$_2$, 10% glycerol. After incubation for various times with cell extract, siRNAs were analyzed on 20% polyacrylamide gel containing 7M Urea followed by phosphorimage analysis (Fugi). Data are presented in FIG. 12. FIG. 12A depicts a stability comparison of unmodified and modified antisense strand siRNA. Unmodified single-stranded siRNA has a very short half-life in cell extract, that is 50% of them degraded in <10 min. 2'Fluoro modified single strand doesn't increase its half life. 2'-Ome modification moderately increases the stability of single-stranded siRNA while phosphorothioate modification within the backbone maintains greater stability of the single-stranded siRNA in extracts. FIG. 12B depicts a stability comparison of duplex siRNAs with unmodified and modified antisense strand. Both 2'-Fluoro and 2'-Ome modification at the antisense strand of the duplex siRNA make the duplex RNA much more stable than the unmodified one. However, phosphorothioates modification at antisense strand of the duplex seems only have moderate effect. This may be due to an increased RNAse H sensitivity of hybrids formed from unmodified sense strand and phosphorothioate modified antisense strand. FIG. 12C depicts a stability comparison of duplex siRNAs containing modification at both strands. Modification dramatically increase the stability of the duplex siRNA when made at both strands of the siRNA duplex.

Figure 12D:
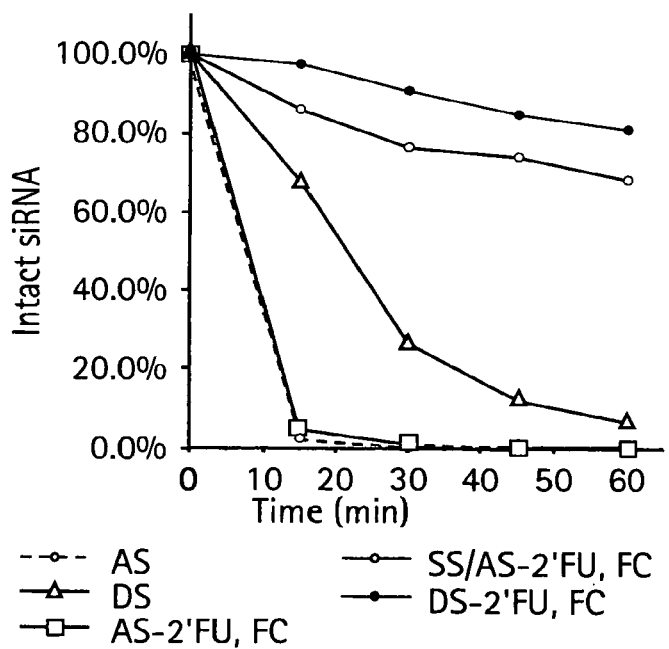
Figure 12E:
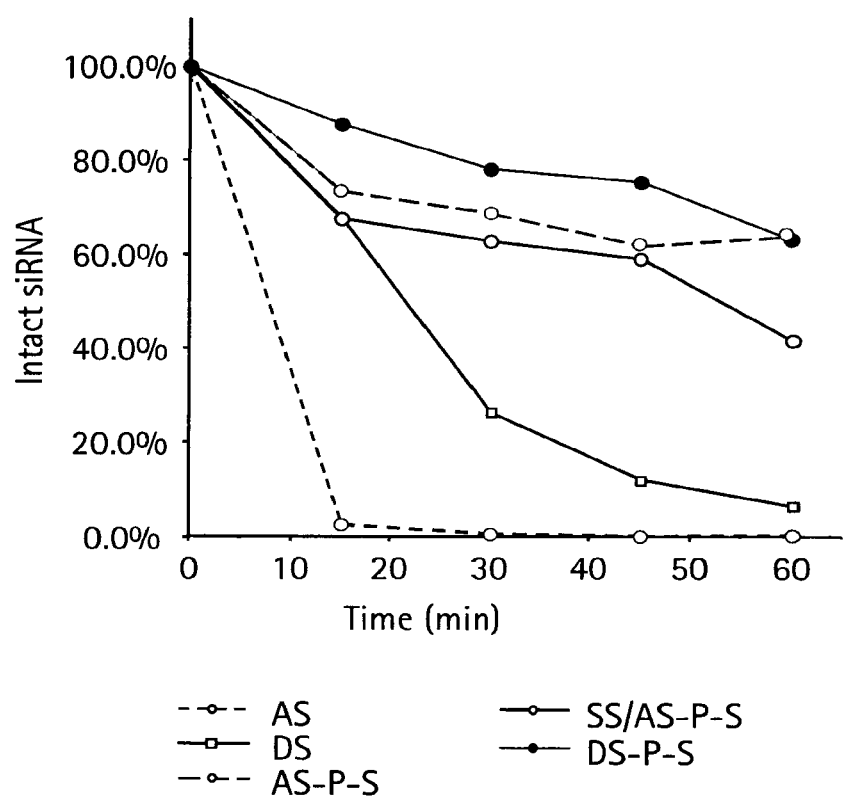

Results from experiments demonstrating similar results are depicted in FIGS. 12D and 12E. FIG. 12D shows the stability of the various 2'FU, FC modified siRNAs as compared to wild type siRNAs over time. Wild type double-stranded siRNAs showed a steady loss of intact siRNAs over the course of the experiment, with only ~7% of the original concentration of intact siRNAs remaining after 1 h in extract (FIG. 12D; dark blue line). Intact modified or unmodified single stranded antisense siRNAs were quickly lost over the time course and were virtually undetectable by 30 min in extract (FIG. 12D; black and red lines). In contrast, double-stranded siRNAs with 2'FU, FC modifications in either the antisense strand or both strands remained predominantly intact over the course of the experiment with ~68 or ~81%, respectively, of the original siRNA population remaining intact throughout the duration of the experiment (FIG. 12D; green and light blue lines). These results indicated that the 2'FU, FC modifications did indeed increase the stability of the siRNAs upon exposure to extract and that having these modifications in both strands provided the siRNAs with the most stability.

In a similar experiment, the stability of P-S modified EGFP siRNAs was evaluated. Unmodified, doubled-stranded antisense siRNAs showed about the same rate of siRNA loss as described in the above experiment (FIG. 12E; dark blue lines). However, P-S modified single-stranded antisense siRNAs showed a markedly increased rate of stability over the course of the experiment, showing ~63% of the original siRNAs remaining intact after 1 h in extract as compared to 0% intact for single-stranded unmodified antisense siRNAs (FIG. 12E; black and red lines). Stability of double-stranded siRNAs with P-S modifications in both strands was comparable to the stability seen with the modified single-stranded antisense strand with ~63% of the originally siRNA population remaining intact after 1 h (FIG. 12E; light blue lines). Double-stranded siRNAs with P-S modifications in only the antisense strand showed weaker but still significant stability with ~42% of the original siRNA population remaining intact through to 1 h in extract (FIG. 12E; green lines). These results showed that the P-S modifications increased the stability of the siRNAs and most notably, increased the stability of both single and double stranded siRNAs.

Example XIII: Quantitative Analysis of RNAi Effects of Duplex siRNAs with 2'-Fluoro Uridine and Cytidine Modifications, and 2'-Fluoro Uridine and Cytidine Modifications in Combination with 2'-Deoxy Modifications, in HeLa Cells Results set forth in Example X indicated that the 2'OH was not required for RNAi and that nucleotides modified with 2' fluoro-groups could be used in siRNA constructs to successfully induce RNAi-mediated gene silencing. To support the conclusion that the 2'OH was not required for RNAi, adenine and guanine deoxynucleotides that inherently have 2'H in place of the 2'OH (FIG. 19) were incorporated into the sense, antisense, or both strands of 2'FU FC-modified EGFP siRNAs to determine their effect on RNAi. This example demonstrates that 2'-OH is not required for siRNA to enter the RNAi pathway, but that an A-form helix is required for mRNA targeting by siRNA.

pEGFP-C1 (as reporter), pDsRed2-N1 (as control) plasmids and various amount of modified siRNA were cotransfected into HeLa cells by lipofectamine. Cells were harvested at 42 h after transfection. Fluorescence intensity of GFP and RFP in total cell lysates were detected by exciting at 488 and 568 nm, respectively. The fluorescence intensity ratio of target (GFP) to control (RFP) fluorophore was determined in the presence of modified siRNAs and normalized to the ratio observed in the mock treated cells.

Figure 13A:
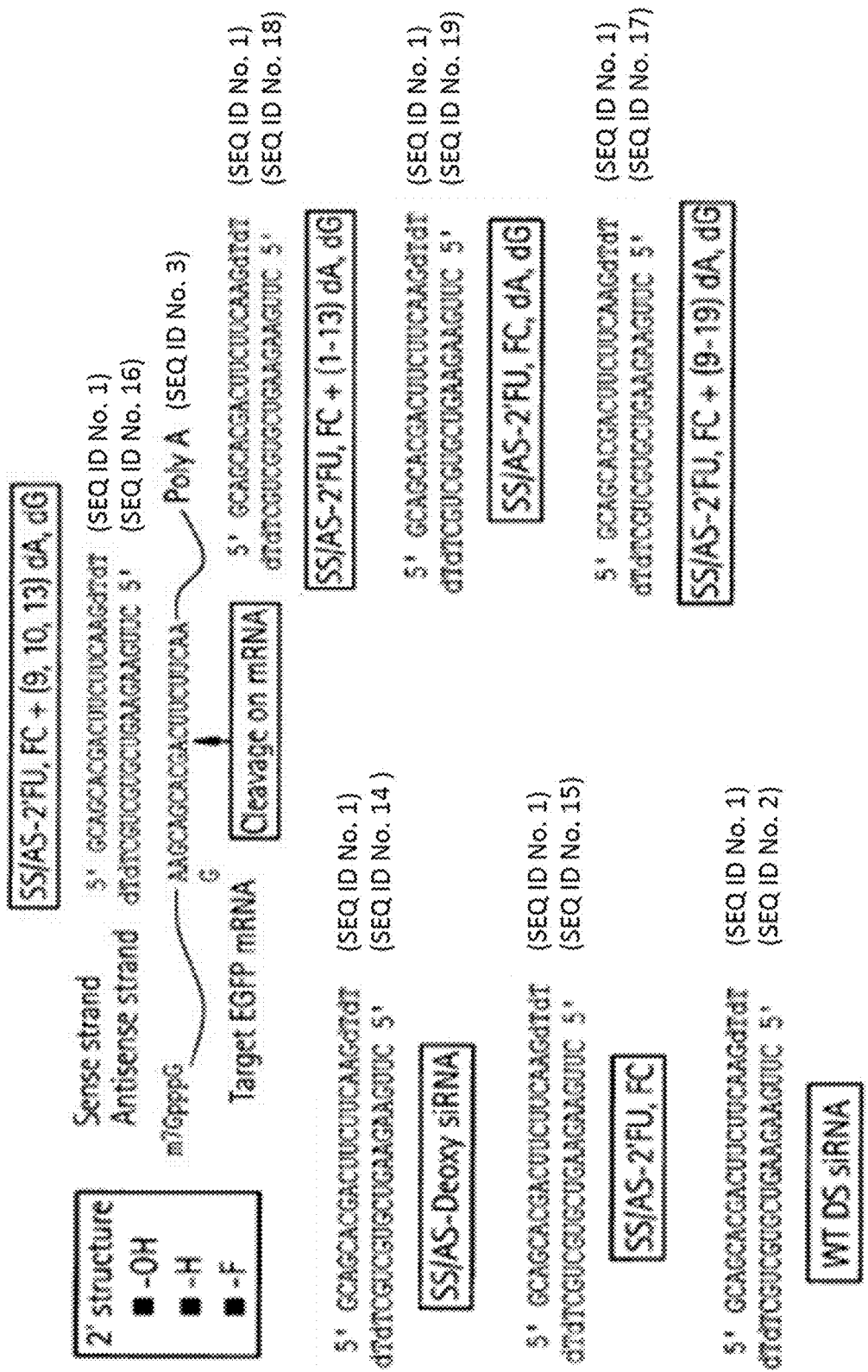

Modified siRNA duplexes with modifications in the antisense strand at the 2' position of the sugar unit are set forth in FIG. 13A and consisted of the following: 2'-hydroxyl wild type (DS), 2'-deoxy modified as siRNAs (SS/AS-Deoxy), 2'-Fluoro U and C modified as siRNAs (SS/AS-2'FU,FC), 2'-Fluoro U and C and 2'-deoxy A and G at positions 9, 10, and 13 modified as siRNAs (SS/AS-2'FU,FC+(9,10,13) dA, dG), 2'-Fluoro U and C and 2'-deoxy A and G at positions 9-19 modified as siRNAs (SS/AS-2'FU,FC+(9-19) dA, dG), 2'-Fluoro U and C and 2'-deoxy A and G at positions 1-13 modified as siRNAs (SS/AS-2'FU,FC+(1-13) dA, dG), and 2'-Fluoro U and C and 2'-deoxy A and G modified as siRNAs (SS/AS-2'FU,FC, dA, dG). The hypothetical cleavage site on the target mRNA is also depicted. The data from cells treated with duplex siRNA with modified antisense strands are set forth in FIG. 13B. A normalized ratio of less than 1.0 indicates a specific RNA interference effect. For comparison, results from unmodified duplex siRNA (ds, lanes 2-6)-treated cells are included.

These data indicate that siRNA with 2'-Fluoro modifications at uridine and cytidine (SS/AS-2' FU,FC, lanes 16-24) is as effective as unmodified duplex siRNA in RNA interference, indicating that 2'-OH is not required for siRNA to enter the RNAi pathway. However, 2'-deoxy substitution in the antisense strand completely bocked siRNA function (SS/AS-2' deoxy, lanes 7-15). In general, mixing 2'-Fluoro modification with deoxy modification could rescue siRNA function (FIG. 13B, lanes 25-60). When 2'FU, FC nucleotides were incorporated into the EGFP siRNA anti-strand with guanine and adenine deoxynucleotides at positions 9, 10, and 13, which base pair with nucleotides lining the cleavage site, (FIG. 13A), EGFP RNAi effects were almost indistinguishable from wild type levels (FIG. 13B, lanes 25-33; Table 1, row 5). In addition, siRNAs that had the entire antisense strand replaced with 2' FU, 2' FC, dATP, and dGTP nucleotides still showed moderate levels of RNAi activity at ~42%, or ~44% if the sense strand was also modified with 2'FU, FC (FIG. 13B, lanes 52-60; Table 1, rows 7, 8).

Figure 13C:

FIG. 13C depicts siRNA duplexes with modifications in both strands at the 2' position of the sugar unit, and consisted of the following: 2'-hydroxyl wild type (DS, lanes 2-6), 2'-deoxy modified as siRNAs (SS/AS-Deoxy, lanes 7-15), 2'-Fluoro U and C modified in both strands (SS-2'FU,FC/AS-2'FU,FC, lanes 16-24), 2'-Fluoro U and C modified in both strands and 2'-deoxy A and G at positions 9, 10, and 13 within the antisense strand (SS-2'FU,FC/AS-2'FU,FC+(9,10,13) dA, dG, lanes 25-33), 2'-Fluoro U and C modified in both strands and 2'-deoxy A and G at positions 9-19 within the antisense strand (SS-2'FU,FC/AS-2'FU,FC+(9-19) dA, dG, lanes 34-42), 2'-Fluoro U and C modified in both strands and 2'-deoxy A and G at positions 1-13 within the antisense strand (SS-2'FU,FC/AS-2'FU,FC+(1-13) dA, dG, lanes 43-51), and 2'-Fluoro U and C modified in both strands and 2'-deoxy A and G within the antisense strand (SS-2'FU,FC/AS-2'FU,FC, dA, dG, lanes 52-60). Results from cells treated with duplex siRNA with modifications in both strands as set forth in FIG. 13C are depicted in FIG. 13D and table 1, rows 6, 8, 30, 32.

All together, these results demonstrated that a 2'OH group was not required for RNAi-mediated degradation and, even more specifically, was not required for nucleotides base paired with nucleotides lining the mRNA cleavage site. There was, however, a limit on the extent to which deoxynucleotides could substitute for ribonucleotides since replacing the entire siRNA sense strand with deoxynucleotides decreased EGFP gene silencing to ~38% inhibition and replacing either the antisense strand or both strands entirely with deoxynucleotides completely abolished EGFP RNAi (see FIG. 10, FIG. 13 and Table 1, rows 9-11). Nonetheless, these results collectively showed that nucleotides with either 2'F- or 2'H groups can selectively replace ribonucleotides within the siRNA sequence to effectively induce RNAi. These data also further demonstrated that A form helix formed by pairing between the antisense strand of siRNA and its target mRNA is required for the RISC protein complex to recognize its target. Furthermore, the data further demonstrated that the 2'OH is not required for the RISC complex to cleave its target mRNA.

Figure 14A:
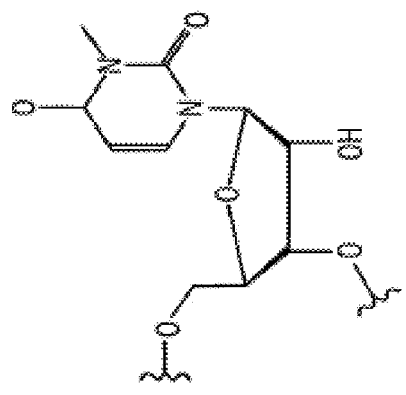
FIG. 14A-C depicts a quantitative analysis of RNAi effects of duplex siRNAs with N3-Methyl uridine modifications in HeLa cells. (A) depicts the structure of N$^3$-Methyl-Uridine (3 mU). (B) RNAi was also abolished if only one 3 MU modification was introduced specifically at U11 of the antisense strand, which is one of the nucleotides that base pairs with A248 of the target EGFP mRNA cleavage site. (C) depicts the results from cells treated with duplex siRNA having 3 mU modifications within the entire antisense strand (SS/AS-3 mU, lanes 7-15), 3 mU modifications within the entire antisense strand and 2'-Fluoro modifications at uridine and cytidine bases within the sense strand (SS-2'FU, FC/AS-3 mU, lanes 16-24), and 3 mU modification at position 11 within the antisense strand (SS/AS-(11)-3 mU, lanes 25-33).
Figure 14B:
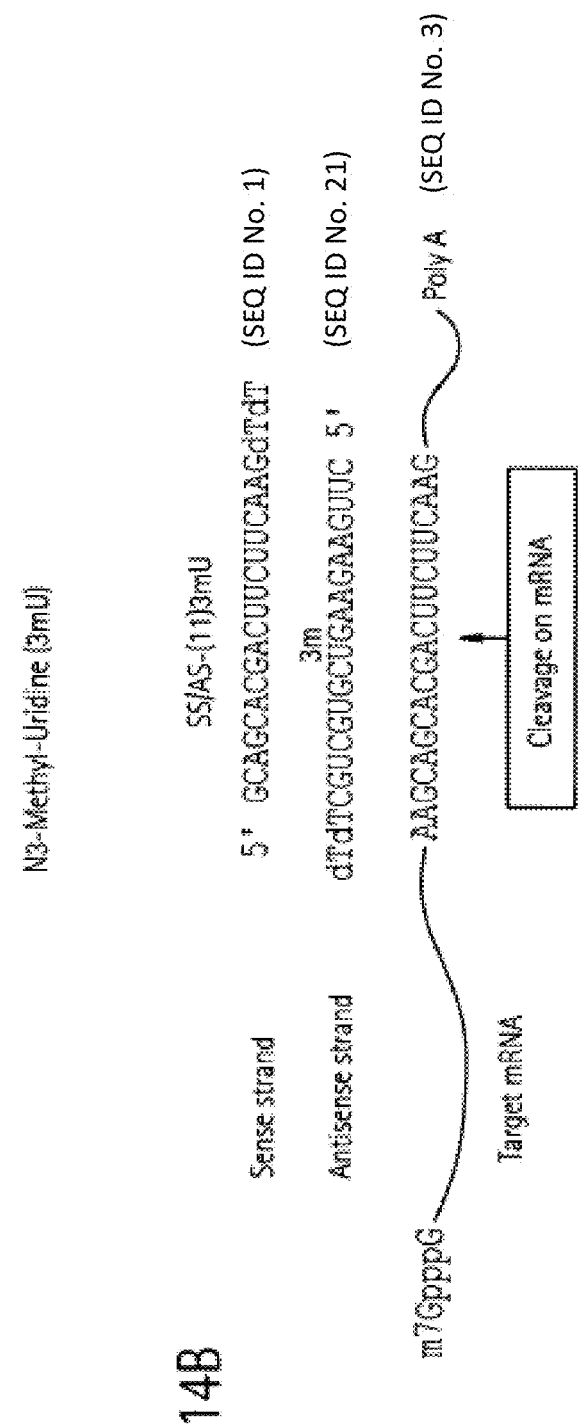
Figure 14C:
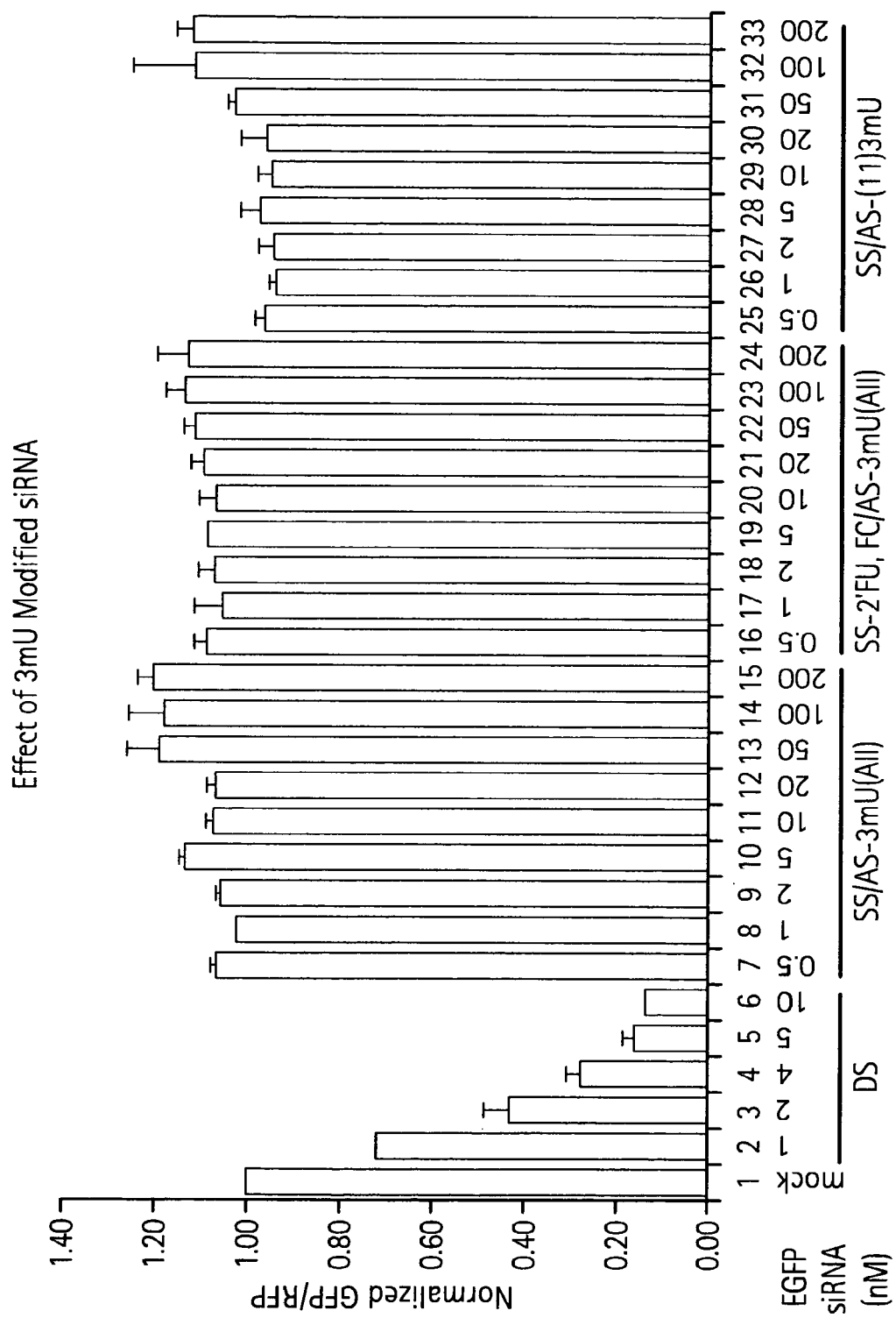

Example XIV: Quantitative Analysis of RNAi Effects of Duplex siRNAs with N3-Methyl Uridine Modifications in HeLa Cells Data set forth in Example V indicated that the A form helix is required for the mechanism of RNAi, as 2 nt bulges that distort A-form helices between antisense siRNAs and target mRNAs abolished RNAi. To test whether the major groove of the A form helix was required for RNAi, siRNAs were modified with $N^3$-Methyl Uridine (3 MU) nucleotides that remove an H-bond donor at $N^3$—H. The structure of $N^3$-Methyl-Uridine (3 mU) is depicted in FIG. 14A. Structurally, the bulky $N^3$-Methyl group would jut into the major groove of the A-form helix, potentially introducing sterical clash between base pairs. In addition, the presence of 3 MU in the major groove may also introduce a steric clash between RNA and RNA-interacting proteins (Saenger, 1984). Therefore, both steric hindrance and the loss of an H-bond donor by the addition of the $N^3$-Methyl group should destabilize RNA-protein interactions in the major groove.

pEGFP-C1 (as reporter), pDsRed2-N1 (as control) plasmids and various amount of modified siRNA were cotransfected into HeLa cells by lipofectamine. Cells were harvested at 42 h after transfection. Fluorescence intensity of GFP and RFP in total cell lysates were detected by exciting at 488 and 568 nm, respectively. The fluorescence intensity ratio of target (GFP) to control (RFP) fluorophore was determined in the presence of modified siRNAs and normalized to the ratio observed in the mock treated cells. FIG. 14C depicts the results from cells treated with duplex siRNA having 3 mU modifications within the entire antisense strand (SS/AS-3 mU, lanes 7-15), 3 mU modifications within the entire antisense strand and 2'-Fluoro modifications at uridine and cytidine bases within the sense strand (SS-2'FU, FC/AS-3 mU, lanes 16-24), and 3 mU modification at position 11 within the antisense strand (SS/AS-(11)-3 mU, lanes 25-33). The modified siRNA duplexes were prepared by annealing modified antisense strand containing single or multiple 3 mU modifications with unmodified sense strand (SS/AS-(11)-3 mU and SS/AS-3 mU) or sense strand having 2'-Fluoro modifications (SS-2'FU, FC/AS-3 mU). For comparison, results from cells treated with unmodified duplex siRNA (ds, lane 2-6) are also shown. 3 MU modified EGFP siRNAs introduced into Hela cells completely abolished RNAi (FIG. 14C, Table 1, rows 25). RNAi was also abolished if only one 3 MU modification was introduced specifically at U11 of the antisense strand, which is one of the nucleotides that base pairs with A248 of the target EGFP mRNA cleavage site (FIGS. 14B and 14C, Table 1, row 26). These results indicated that disrupting the functional groups of the major groove of the A-form helix formed by the antisense strand and its target mRNA specifically at the cleavage site inhibited RNAi. These data also suggested that the major groove was required for mediating RNAi and for RNA-RISC* interactions that subsequently lead to mRNA cleavage.

Example XV: Structural Integrity of the 5' End of the Antisense Strand in siRNA-mRNA Duplexes is More Important for Mediating RNAi than the 3' End Data set forth in Example VII using psoralen photochemistry suggested that complete unwinding of the siRNA duplex is not required for RNAi in vivo because psoralen cross-linked siRNAs did not completely abolish gene silencing. These results suggested that a single cross-linking event occurring near the 3' end of the antisense strand still allowed for the initial unwinding of duplex siRNAs from the 5' end, freeing enough of the nucleotides in the antisense strand to hybridize to the target mRNA and induce RNAi, even if unwinding was not complete. The location of this crosslinking site is indicated by a bar in FIG. 15A. If this were the case, then unwinding of siRNAs must start from the 5' end of the antisense strand, a conclusion supported by the fact that blocking either the 3' end of the antisense siRNA strand or the 5' end of the sense siRNA strand had no significant effect on RNAi activity (see Examples III and IV). If this 5' to 3' unwinding model was correct, sequences near the 3' end of the antisense siRNA strand or 5' end of the sense siRNA strand should be changeable without significantly interfering with RNAi.

Figure 15C:
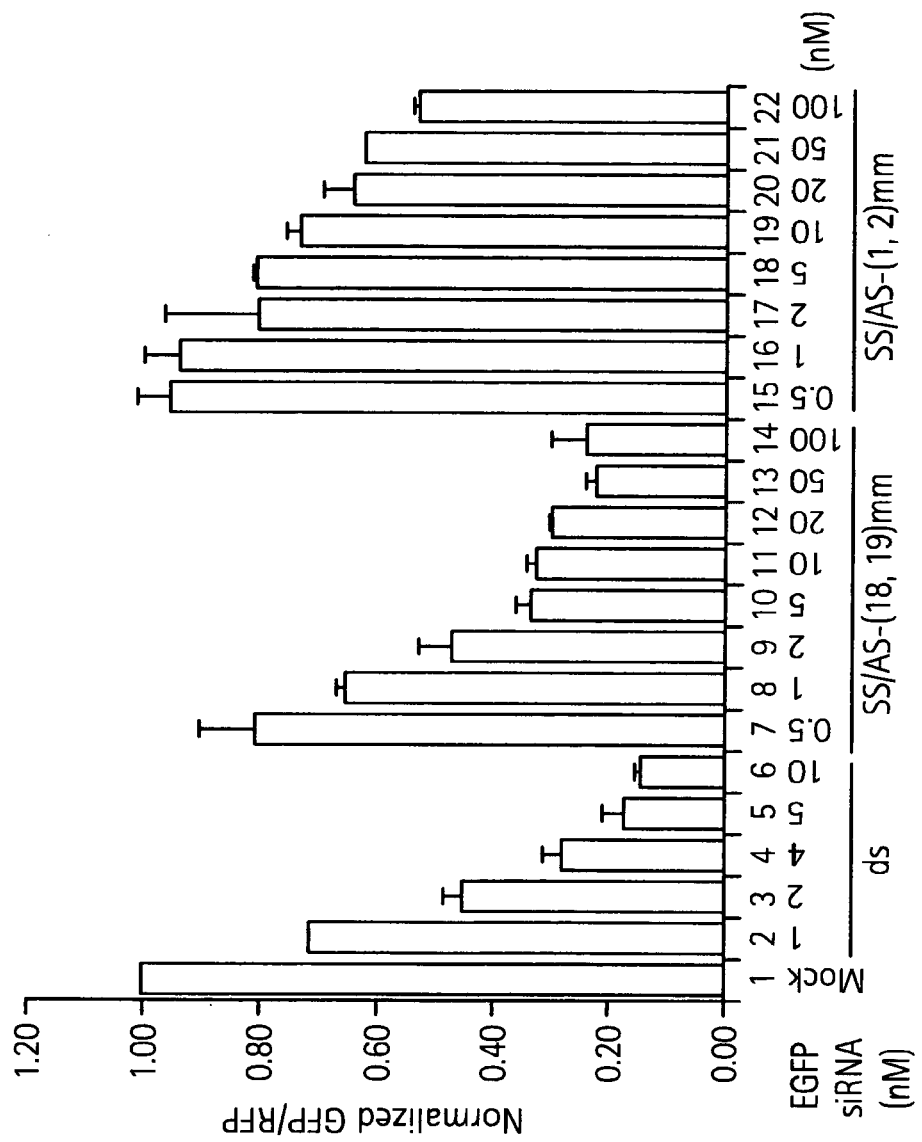

This Example directly tests the model set forth above and demonstrates an aysmmetric requirement for duplex siRNA structure in RNA interference in vivo. To test this hypothesis, EGFP siRNAs with mismatched base pairs at either the 5' (nt 1, 2) or 3' (nt 18, 19) ends were introduced into the antisense strand (FIG. 15B). pEGFP-C1 (as reporter), pDsRed2-N1 (as control) plasmids and various amount of modified siRNA were cotransfected into HeLa cells by lipofectamine. Cells were harvested at 42 h after transfection. Fluorescence intensity of GFP and RFP in total cell lysates were detected by exciting at 488 and 568 nm, respectively. The fluorescence intensity ratio of target (GFP) to control (RFP) fluorophore was determined in the presence of modified siRNAs and normalized to the ratio observed in the mock treated cells. FIG. 15C depicts results from cells treated with duplex siRNA having mismatches located at the 3' end [SS/AS-(18,19) mm, lanes 7-14] or 5' end [SS/AS-(1,2) mm, lanes 15-22] of the antisense strand. For comparison, results from unmodified duplex siRNA-treated cells are also shown (ds, lane 2-6). siRNAs with mismatches near the 5' end of the antisense strand showed only ~35% inhibition in the dual fluorescence reporter assay whereas mismatches at the 3' end retained a significant level of gene silencing at ~77% (FIG. 15C; Table 1, rows 27-28). These results strongly indicated that the integrity at the 5' end of the antisense strand in the duplex was functionally more important than the 3' end.

Further demonstrating this point are data set forth above in Example XIII, wherein 2'FU, FC plus dATPs, dGTPs were incorporated into the antisense strand siRNAs predominantly at the 5' end (nts 1-13) or predominantly at the 3' end (nts 9-19) (see FIG. 13C). In the dual fluorescence reporter assay, predominantly 5' modified antisense [AS-2'FU, FC+(1-13) dA, dG] EGFP siRNAs were only moderately effective, inducing RNAi at ~43%, or at 45% if the sense strand was also modified to 2'FU, FC (see FIG. 13C, Table 1, rows 29-30). However, predominantly 3' modified and 5' unmodified antisense [AS-2'FU, FC+(9-19) dA, dG] siRNAs significantly induced RNAi activity at ~91%, or at 64% if the sense strand was also modified to 2'FU, FC (see FIG. 13C, Table 1, rows 31-32). These contrasting results suggested that the 5' region of the antisense strand was more sensitive to modification than the 3' end. All together, these data suggested that recognition of siRNA duplexes by an as yet unidentified RNA helicase occurs asymmetrically with the structure of the antisense 5' end of the duplex preferentially distinguished from the 3' end during the initiation of unwinding.

Example XVI: Modified siRNAs that Stabilize A-U Base Pair Interactions can Induce RNAi In addition to incorporating modifications that affected the stability of siRNAs, nucleotides chemically modified to strengthen the base pair interactions between two complementary bases were analyzed. In theory, increasing the stability of base pair interactions may increase the targeting efficiency of siRNAs to target mRNA sequences.

Increasing targeting efficiency may then induce more robust RNAi effects with siRNAs that are weaker at binding to their target sequence or have mismatched sequences, and thus, are not showing a high degree of RNAi.

Figure 16:
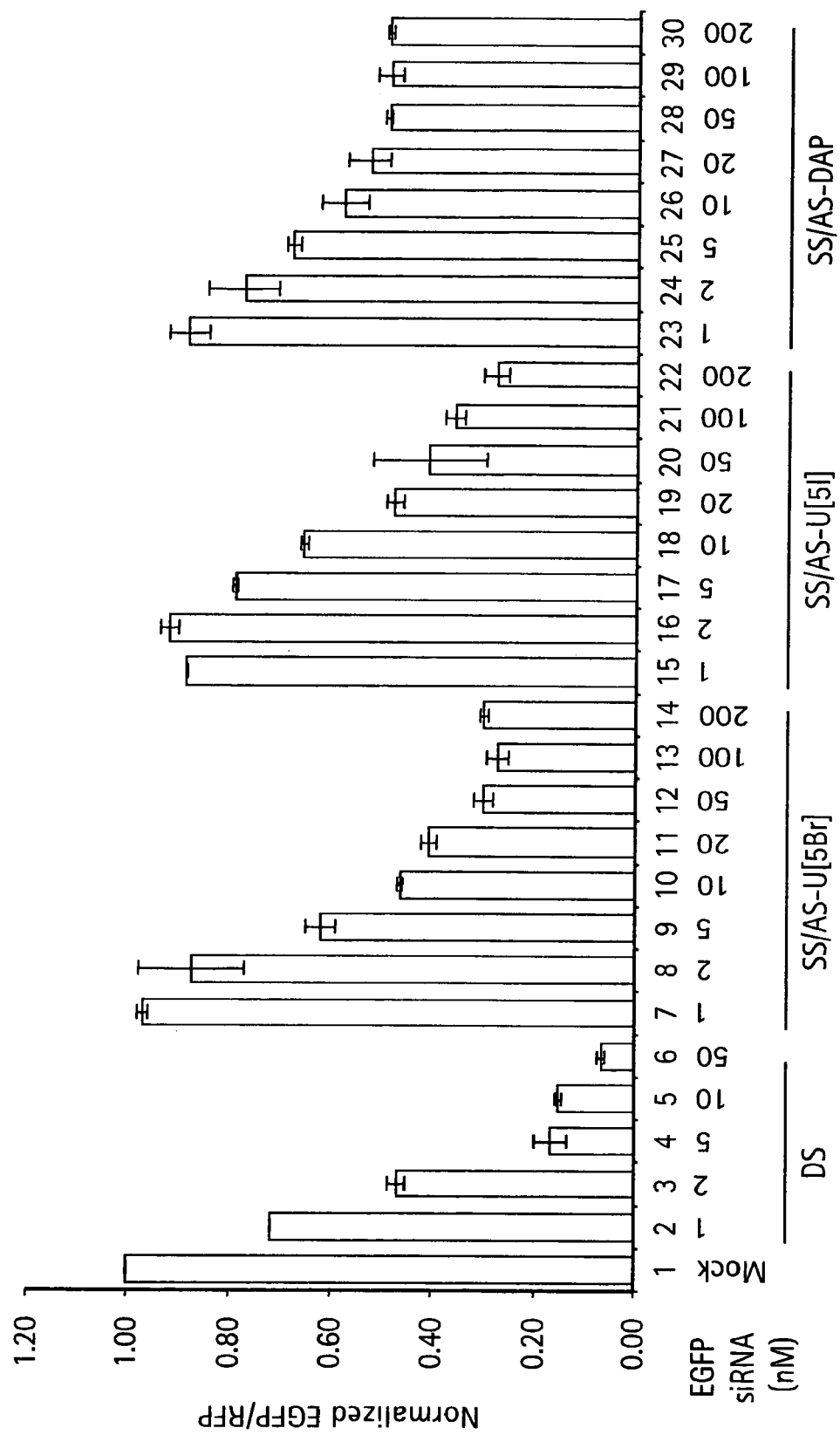
FIG. 16 depicts a quantitative analysis of RNAi effects of duplex siRNAs with 5-Br uridine, 5-I uridine and diaminopurine modifications in the antisense strand in HeLa cells.

To bolster base pairing interactions, 5-Bromo-uridine (U[5Br]), 5-Indo-uridine (U[5I]) or 2,6-Diaminopurine (DAP) (FIG. 19), which are modified nucleotides known to increase the association constant between A-U base pairs (Saenger, 1984), were incorporated into siRNAs and tested in the dual fluorescence report assay. Double-stranded siRNAs having U[5Br], U[5I] or DAP modifications incorporated into the antisense strand were capable of inducing RNAi activity at levels of ~70% for U[5Br], ~59% for U[5I] and ~51% for DAP (FIG. 16, Table 1, rows 19-21).

Interestingly, when 2'FU, FC stabilizing modifications in the sense strand were combined with these modifications in the antisense strand, gene silencing was not as efficient as wild type in inducing RNAi. EGFP gene silencing was 31% for the 2'FU, FC-modified sense siRNA base paired with U[5Br]-, ~42% for U[5I]-, or ~35% for DAP-modified antisense siRNAs (Table 1, rows 22-24). These results suggested that enhancing the interactions between base pairs through these siRNA modifications was a viable option for increasing mRNA targeting efficiency, but that there was a limit to how stable the base pairing interactions can be made before they interfere with siRNA unwinding.

Example XVII: Modified siRNAs Enter into the RNAi Pathway in HeLa Cell Lysates

Although the dual fluorescence reporter assay did detect changes in EGFP gene expression with the modified siRNAs created herein, it was possible that gene silencing was being induced by a mechanism other than RNAi-mediated degradative pathways. This Example demonstrates that modified siRNA enter into the RNA interference pathway by using an in vitro RNAi assay. To test whether the targeted mRNA was indeed being cleaved upon exposure to modified siRNAs, an in vitro RNAi assay was performed to measure the cleavage of a $^{32}$P-cap labeled mRNA target upon incubation with modified siRNAs and HeLa cytoplasmic extract. This in vitro RNAi assay is well known in the art. Cleavage products were resolved on an 8% polyacrylamide-7 M urea gel.

In this assay, 10 nM cap-labeled target RNA was incubated with 100 nM siRNA having the following modifications within the antisense strand: 2'-Fluoro U and C (SS/AS-2'FU,FC), 2'-Fluoro U and C and 2'-deoxy A and G at positions 9, 10 and 13 (SS/AS-2'FU,FC+(9,10,13) dA,dG)), 2'-Fluoro U and C and 2'-deoxy at each A and G (SS/AS-2'FU,FC+dA,dG), 2'-deoxy at each position (SS/AS-2'-deoxy), 2'-OMe at each residue (SS/AS-2'-OMe), P-S at each residue (SS/AS—P-S), 5-Bromo-uridine at each U (SS/AS-U[5Br]), (5-Indo-uridine at each U (SS/AS-U[5I]), DAP at each purine (SS/AS-DAP), 3 MU at each U (SS/AS-3 MU), 3 MU at position 11(SS/AS-91103 MU), mismatches at position 1 and 2 (SS/AS-(1,2) mm), mismatches at position 18 and 19 (SS/AS-(18,19) mm), 2'-Fluoro U and C and 2'-deoxy A and G at positions 1-13 (SS/AS-2'FU,FC+(1-13) dA,dG), and 2'-Fluoro U and C and 2'-deoxy A and G at positions 9-19 (SS/AS-2'FU,FC+(9-19) dA,dG). Reaction products were resolved on an 8% polyacrylamide-7M urea gel.

Figure 17:
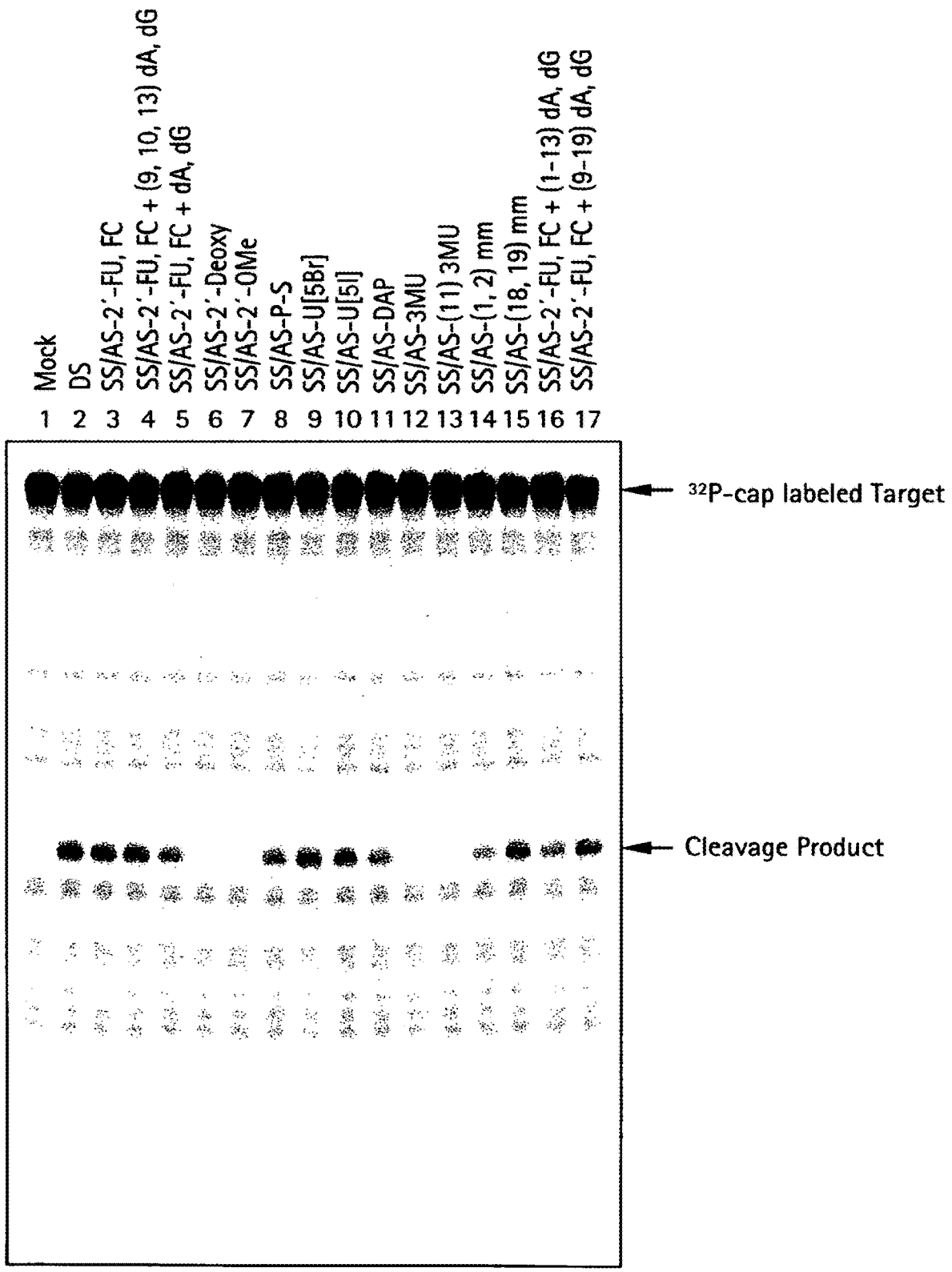
FIG. 17 depicts target RNA cleavage by duplex siRNAs with various modifications in HeLa cell lysates.

Results from the assay are depicted in FIG. 17. The arrows indicate the capped target RNA and the 5' cleavage product; the resulting 3' fragment is unlabeled and is therefore invisible. Mock treated mRNAs did not show an observable cleavage product (FIG. 17, lane 1), but wild type and all modified siRNAs that displayed gene silencing effects in vivo showed clearly visible cleavage products in vitro (FIG. 17; lanes 2, 8-11,14-17). Furthermore, modified siRNAs that did not show any marked gene silencing effects in vivo did not show any distinct cleavage products in the in vitro assay (FIG. 17; lanes 1, 6-7, 12-13), suggesting that the cleavage events observed were specifically dependent on functional siRNAs. These in vitro results provided a strong correlation between the in vivo gene silencing observed with the modified siRNAs and target mRNA degradation, indicating that the modified siRNAs were distinctly targeting mRNAs for cleavage and subsequent degradation through the in vivo RNAi pathway.

Summary of Examples VIII-XVII

By introducing various chemical modifications into siRNAs and measuring their effects on RNAi, the above examples reveal new insights into the mechanism of RNAi and teach new approaches for increasing the efficacy of RNAi in vivo, e.g. in human cells.

Figure 18:
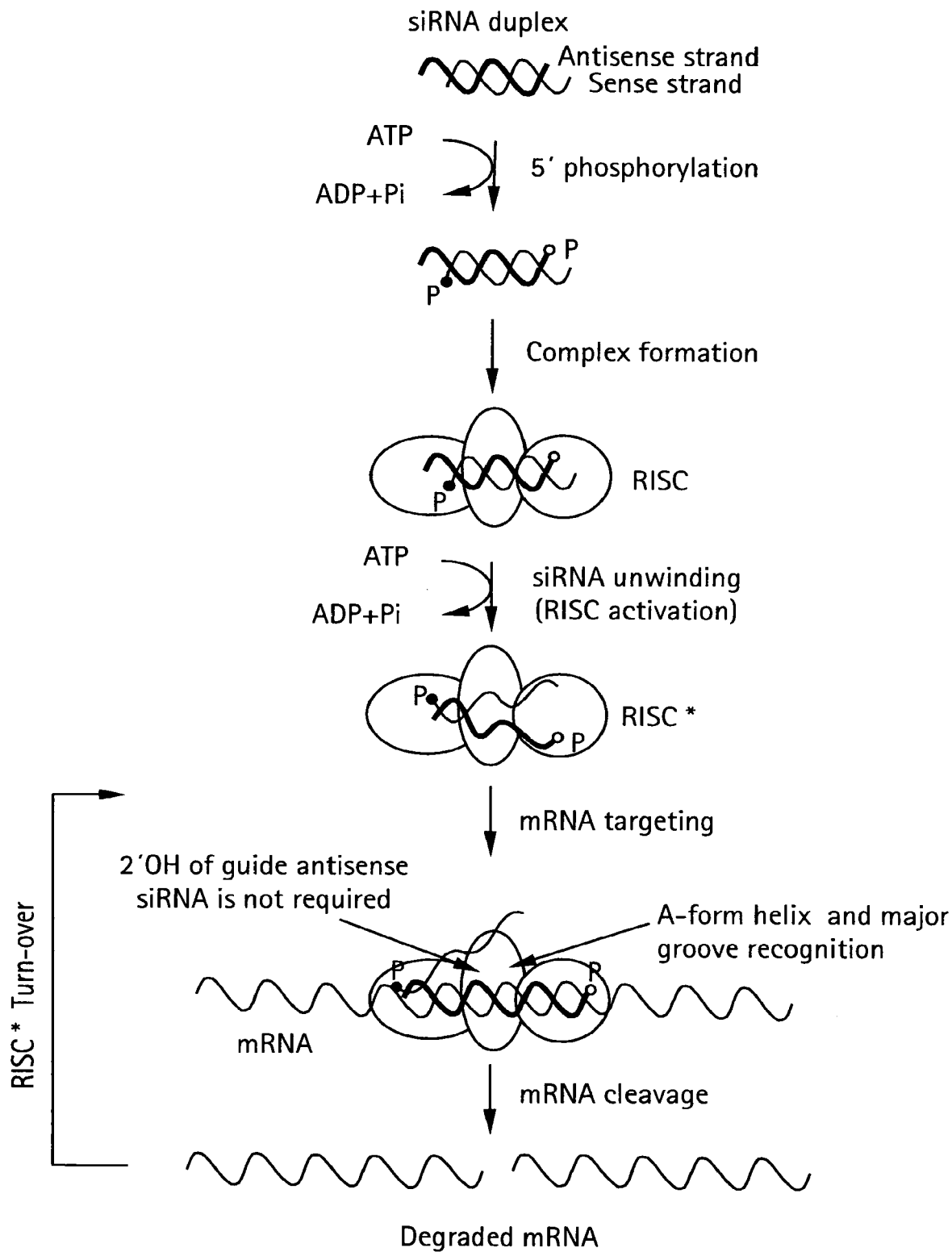
FIG. 18 depicts the mechanism for RNAi in human cells highlighting the requirement of the A-form helix and major groove for mRNA cleavage and the steps which do not require the RNA 2'OH of the guide antisense siRNA.

The step-wise process of RNAi is depicted in FIG. 18. In the first step of RNAi induction, the 5' ends of the siRNA duplex are phosphorylated, resulting in the formation of a siRNA-RISC complex. The data presented here showing the asymmetric nature of unwinding then suggests an ATP-dependent event during which siRNA is unwound from the 5' end of the antisense strand and RISC is activated. Following RISC activation, the antisense strand of the unwound siRNA guides the siRNA-RISC* complex to the target mRNA. The guide antisense strand base pairs with the target mRNA, forming an A-form helix and the RISC* protein complex recognizes the major groove of the A-form helix, an event that occurs independently of the RNA 2'OH of the guide antisense siRNA. In the final step of this process, the target mRNA is cleaved by RISC*, which is another event that occurs independently of the 2'OH of the guide antisense siRNA. RISC* is then recycled to catalyze another cleavage event.

A. The Requirement for the A-Form Helix Supercedes the Requirement for the 2'OH in RNAi Several important mechanistic findings were presented here that not only more clearly defined the mechanism of the RNAi pathway, but will also increase the utility of RNAi in various applications. That the 2'OH was not required for RNAi was the most important of these results as this discovery has several important implications for the structural and catalytic elements required for the RNAi pathway. Remarkable functional implications were that the RNAi machinery does not require the 2'OH for recognition of siRNAs and the catalytic ribonuclease activity of RISC does not involve 2'OH groups of the guide antisense RNA. Another consequence of this discovery was that a variety of chemical modifications, including fluoro- or deoxy-groups, could substitute for the 2'OH in siRNAs, indicating that no distinguishing chemical specificity was required for RNAi at the 2' position. These findings would suggest that other properties of the siRNA-mRNA duplexes, such as core structural elements, were essential for siRNA. If helical structure was the key to RNAi induction, then the A-form helix that forms between siRNAs and the target mRNA would indeed be required for RNAi, as was previously shown (Chiu and Rana, 2002). Furthermore, the 2' fluoro- or combined 2' fluoro-, deoxy modified antisense siRNAs lacking the 2'OH would have to competently form an A-form helix to induce RNAi as shown here. This will likely turn out to be the case since 2' fluoro-modified RNA-RNA hybrids were previously reported to exhibit an A-form helical conformation (Cummins et al., 1995; Luy and Marino, 2001), lending significant merit to the idea that helical structure strongly influences RNAi efficiency. Still another implication of these particular results was that alternate chemical groups at the 2' position that allow the A-form helix to be retained but help siRNAs evade recognition by RNases can increase siRNA stability and prolong RNAi effects induced in vivo.

It was previously shown in *C. elegans* and *Drosophila* extracts that completely substituting one or both siRNA strands with deoxynucleotides abolished RNAi (Elbashir et al., 2001; Parrish et al., 2000), and those observations were consistent with the data presented here. The failure of true DNA-RNA hybrids to induce RNAi most plausibly relates to the argument that structure, and thus the A-form helix, was an essential determinant for RNAi induction. Based on circular dichroism spectra, DNA-RNA hybrids displayed characteristics that were intermediate between A- and B-form helices (Cummins et al., 1995). Following the contention that the A-form helix was an absolute requirement for RNAi induction, 2' deoxy siRNA-mRNA target duplexes would not be recognized by the RNAi machinery because they would not be forming the proper A-form helical structure. Therefore, RNAi would not be induced by DNA-RNA hybrids, as has been observed. It is also worth mentioning that microRNAs (miRNAs) induce post-transcriptional gene silencing (PTGS) through the same pathway as RNAi but ultimately, only inhibit translation machinery instead of inducing RNA degradation, the event that defines RNAi. The only observable difference between the two mechanisms is that RNAi requires the A-form helix but miRNA-induced PTGS does not, as miRNAs often mismatch with their target mRNAs, forming a bulge that would distort the helical structure. This would suggest that the differences between the miRNA-induced silencing mechanism and siRNA-mediated RNAi may solely be attributable to differences in RNA-RNA helical structure, and further supported a model in which helical structure was the sole determinant for whether RNAi was induced.

It was also previously reported that replacement of uridine with 2' FU, corresponding to ¼ of the bases of long dsRNAs elicited RNAi effects in *C. elegans*, while deoxycytodine incorporated into long dsRNAs diminished RNAi effects (Parrish et al., 2000). However, exactly where these modified nucleotides fell within the sequence structure of RNAi-inducing siRNAs and whether these modified nucleotides in the longer RNAs corresponded to the mRNA cleavage site or major groove after being processed to siRNAs was not clear. It has also been reported that siRNAs in which 3' overhangs and two of the 3' end ribonucleotides were replaced with deoxyribonucleotides retained RNAi activity upon exposure to *Drosophila* extracts (Elbashir et al., 2001). Presumably, replacing two of the 3' end base-paired nucleotides with deoxynucleotides would not disrupt the overall A-form structure of the siRNA-mRNA duplex required for RNAi and would thereby allow RNAi induction.

Neither analyses in *C. elegans* or in *Drosophila* extracts ascertained whether there was a distinct requirement for the 2' OH for cleavage site recognition and the cleavage event itself during RNAi induction. The results presented here demonstrated that exclusively using 2'FU, FC modifications in siRNAs and selectively substituting in deoxyribonucleotides for nucleotides base paired with the nucleotides lining the mRNA cleavage site, or even replacing the entire sequence of siRNA with a combination of 2' fluoro- and 2' deoxy-nucleotides, elicited RNAi induction. Therefore, it has now been definitively established that recognition of the mRNA-target cleavage site and subsequent cleavage did not require the 2'OH of the antisense siRNA to induce RNAi. As a final point, the inhibitory RNAi effects seen with the bulky 2'OMe modification, which was also shown previously with *Drosophila* (Elbashir et al., 2001), did demonstrate that there were steric constraints on the types of 2' modifications that would be amenable for inducing RNAi. As 2'OMe modifications probably did not disrupt the A-form helix of the siRNA-mRNA duplex (Cummins et al., 1995), the methyl group may be sterically interfering with protein-RNA interactions thereby preventing RNAi. Nevertheless, steric constraints notwithstanding, this analysis conclusively showed that the non-essential nature of the 2' position could very much be exploited for improving the efficacy of RNAi in a variety of applications.

B. Improving the Efficacy of RNAi Using Chemical Modifications

The chemical modifications analyzed improved upon the status quo short-lived RNAi effects seen in vivo in human cells, significantly increasing the duration of RNAi effects typically observed. Modifications like the 2' fluoro- and P—S linkages both increased the half-life of siRNAs upon exposure to cytoplasmic extracts, and in vivo studies with 2' FU, FC siRNAs showed that increasing the half life of siRNAs did in fact prolong the effects of RNAi. This indicated that short-lived RNAi effects usually observed in human cells were due at least in part to the degradation of siRNAs. That the stabilizing siRNA modifications still allowed for a substantial level of RNAi induction showed that these modifications will be invaluable for studying the phenotypic effects of prolonged gene-silencing in cell culture or in increasing the long-term in vivo effects of siRNAs in clinical applications. Interestingly, the P-S-modified, single-stranded antisense strand did not show increased RNAi effects in the dual fluorescence reporter assay used here (data not shown) despite showing significantly increased stability (FIG. 3A (a)). This suggested that stability was not the main reason why single-stranded antisense RNAi was not as effective in inducing RNAi as dsRNA. Nonetheless, creating P-S modifications in the siRNA backbone showed that stabilizing the siRNA backbone did not inhibit RNAi and signified that using chemical modifications that stabilized phosphate linkages was a viable option for prolonging RNAi effects.

Another option for increasing the efficacy of RNAi was uncovered by the analysis of modifications that should enhance base pairing interactions between antisense siRNA and targeted mRNA. DAP is a naturally occurring nucleobase that sometimes replaces adenine in phages like the cyanophage S-2L (Kirnos et al., 1977). Incorporation of DAP into RNA strands promotes the formation of three Watson and Crick hydrogen bonds between DAP and uridine, increasing the stability of interactions seen between A-U base pairs (Luytena and Herdewijna, 1998). U[5Br] and U[5I] have also been shown to have higher association constants when base paired to A residues than unmodified uridine (Saenger, 1984). When any of these modifications were incorporated into siRNAs, RNAi was still quite efficient, indicating that modifications that stabilize base pairing interactions can be used in designing siRNAs for various applications. It was also notable that siRNAs with 2' Fluoro-modifications introduced into sense strands and base paired with the DAP, U[Br] or U[5I] antisense strands had decreased RNAi efficiency. 2' Fluoro-modifications have been shown to significantly increase the melting temperature between base pairs (Cummins et al., 1995). Consequently, the stabilizing effect on base pairing interactions when both the 2' Fluoro- and DAP, U[Br] or U[5I] modifications were present may have actually hindered the unwinding of the siRNA duplex. If the unwinding of the siRNA was hindered, then there would be less single antisense siRNAs available to induce RNAi, accounting for the observed decrease in RNAi activity.

C. Other Structural Determinants for RNAi Induction

Another structural facet of the RNAi mechanism was uncovered using the 3 MU modification which showed that the major groove of the A-form helix was required for RNAi. This finding builds on previous data showing that the A-form helix was required for RNAi (Chiu and Rana, 2002). Together, these results suggested that the specific structure of the A-form helical RNA that forms the major groove and contains the mRNA cleavage site was important for recognition by the RNAi machinery. Conceivably, RNA-RISC* contacts depend on the structural integrity of the major groove for precise interactions and ultimately, to initiate cleavage of the target. By disrupting the major groove, RISC* may no longer be able to interact or only weakly interacts with the siRNA-mRNA target duplex thereby preventing mRNA cleavage. Alternatively, RISC* might still be able to interact with the destabilized RNA helix but not recognize the cleavage site within the major groove as the catalytic site if the conformation of the RNA helix and more specifically the major groove was altered.

The other structural property of siRNAs defined by these analyses was the asymmetric nature of siRNA unwinding. Initiation of siRNA unwinding from the 5' end was previously suggested from the ability of single cross-linked siRNAs to still induce RNAi (Chiu and Rana, 2002). Building on those studies by stacking mismatched or modified nucleotides on either the 3' or 5' end of the antisense strand to gauge the tolerance for mismatches or modifications on one end over the other, it was shown here that RNAi depended on the integrity of the 5', and not the 3', end of the antisense strand of the siRNA duplex. These results suggested that like RISC*, the RNA helicase, which has not yet been identified, also recognizes structural properties of the siRNA duplex as opposed to specific sequences of the RNA strands. This recognition appears to be asymmetric with the structure of the antisense 5' end favored over the 3' end, and is similar to how restriction enzymes can preferentially cleave the DNA backbone asymmetrically within a palindromic sequence. Further structural analysis of siRNAs to pinpoint what properties of the antisense 5' end contribute to the asymmetric nature of the duplex should help elucidate the specific structural elements required for duplex recognition by the RNA helicase for siRNA unwinding. That the modified siRNAs displayed effective RNAi in vivo and in vitro was also significant as it confirmed that the observed gene silencing was mediated by the RNAi pathway. These results also indicated that using chemical modifications that allow for efficient RNAi induction should work in the design of any given siRNA to increase its stability and capacity to specifically induce RNAi in vivo.

Example XVIII: Peptide Modification of 3' Termini of siRNA

Peptides can be linked to the 3' terminus of an siRNA. For example, an siRNA containing $NH_2$ groups at their 3' termini can be synthesized using methods known in the art and as described herein, thus producing, e.g., exocyclic amine on protected nucleotides. In an example of a peptide modification of a 3' terminus of an siRNA, a Tat-derived peptide (from amino acids 47-57) was synthesized on solid support (rink amide resin) using standard FastMoc protocols. A cysteine residue was added to the amino terminus of the peptide for conjugation to the RNA. All Fmoc-amino acids, piperidine, 4-dimethylaminopyridine, dichloromethane, N, N-dimethylforamide, 1-hydroxybenzotriazole (HOBT), 2-(1H-benzotriazo-1-yl)-1,1,3,3-tetramethyluronium hexafluorophosphate (HBTU), diisopropylethylamine, and HMP-linked polystyrene resin were obtained from Applied Biosystems Division, Perkin Elmer. Trifluoroacetic acid, 1,2-ethanedithiol, phenol, thioanisol were from Sigma. Cleavage and deprotection of the peptide was carried out in 2 ml of Reagent K for 6 hours at room temperature. Reagent K contained 1.75 ml TFA, 100 μL thioanisole, 1000 water, and 50 μl of ethanedithiol. After cleavage from the resin, peptide was purified by HPLC on a Zorbax 300 SB-C8 column. The mass of fully deprotected and purified peptides was confirmed by FAB mass spectrometry.

siRNA containing 3'-end amino groups were synthesized. NHS-ester-maleimide crosslinkers (Pierce) were used for conjugation to Tat peptide (amino acids 48-57) and the conjugation reaction was carried out according to the manufacturer's instructions. The NHS ester moiety of the crosslinker was reacted with the RNA as described herein. After purification on a C18 column, the RNA-NHS-maleimide conjugate was added to the peptide that contains Cys (0.1 M phosphate, pH 8, room temperature, 1 hour). Peptide-RNA conjugate was purified on 7 M-urea denaturing gels.

Similar methods can be used to attached other compounds, e.g., nanoparticle-RNA conjugates can be prepared using such methods.

Transfection of the siRNA-peptides was carried out without Lipofectamine™ or any other transfection reagents. Robust RNAi activity was observed.

These data demonstrate that modification of the 3' terminus of siRNA does not eliminate the ability of the siRNA derivative to be effective for inhibiting expression of a targeted sequence. Furthermore, such siRNA derivatives can be used directly for transfection without the use of transfection reagents.

Example XIX: Photocleavable Biotin Modification of 3' Termini of siRNA

A novel photocleavable biotin was synthesized and attached to the 3' terminus of an siRNA. Briefly, NHS esters of biotin (5 nmole) were conjugated to free amino groups at the 3'-end of an siRNA duplex (1 nmole) in an aqueous solution (e.g., 0.1 M phosphate buffer pH 8 at room temp for 1 hour). 3'-end amino RNA was purchased from a commercial source (Dharmacon). RNA-biotin siRNA was incubated with cell extracts and the RNA-protein complex was isolated using avidin magnetic beads. After adding the mutant competitive non-biotin RNA and followed by extensive washing, RNA-protein complexes were released by long wave UV (360 nm) treatment at room temperature. In previous methods, avidin beads are heated with SDS to release proteins that also contain a large number of bead-binding proteins. The present method allows the isolation of specific siRNA-bound proteins. The structure of the novel photocleavable biotin is shown in FIG. 20.

Experimental Procedures for Examples I-XIX siRNA Preparation 21-nucleotide RNAs were chemically synthesized as 2' bis(acetoxyethoxy)-methyl ether-protected oligos by Dharmacon (Lafayette, Colo.). Synthetic oligonucleotides were deprotected, annealed and purified as described by the manufacturer. Successful duplex formation was confirmed by 20% non-denaturing polyacrylamide gel electrophoresis (PAGE). All siRNAs were stored in DEPC (0.1% diethyl pyrocarbonate)-treated water at −80° C. The sequences of GFP or RFP target-specific siRNA duplexes were designed according to the manufacturer's recommendation and subjected to a BLAST search against the human genome sequence to ensure that no endogenous genes of the genome were targeted.

Culture and Transfection of Cells

Hela cells were maintained at 37° C. in Dulbecco's modified Eagle's medium (DMEM, Invitrogen) supplemented with 10% fetal bovine serum (FBS), 100 units/ml penicillin and 100 µg/ml streptomycin (Invitrogen). Cells were regularly passaged at sub-confluence and plated 16 hr before transfection at 70% confluency. Lipofectamine (Invitrogen)-mediated transient cotransfections of reporter plasmids and siRNAs were performed in duplicate 6-well plates as described by the manufacturer for adherent cell lines. A transfection mixture containing 0.16-0.66 µg pEGFP-C1 and 0.33-1.33 µg pDsRed1-N1 reporter plasmids (Clontech), various amounts of siRNA (1.0 nM-200 nM), and 10 µl lipofectamine in 1 ml serum-reduced OPTI-MEM (Invitrogen) was added to each well. Cells were incubated in transfection mixture for 6 hours and further cultured in antibiotic-free DMEM. Cells were treated under same conditions without siRNA for mock experiments. At various time intervals, the transfected cells were washed twice with phosphate buffered saline (PBS, Invitrogen), flash frozen in liquid nitrogen, and stored at −80° C. for reporter gene assays.

In Vivo Fluorescence Analysis pEGFP-C1, pDsRed1-N1 reporter plasmids and 50 nM siRNA were cotransfected into HeLa cells by lipofectamine as described above except that cells were cultured on 35 mm plates with glass bottoms (MatTek Corporation, Ashland Mass.) instead of standard 6-well plates. Fluorescence in living cells was visualized 48 hours post transfection by conventional fluorescence microscopy (Zeiss). For GFP and RFP fluorescence detection, FITC and CY3 filters were used, respectively.

Dual Fluorescence Reporter Gene Assays pEGFP-C1, pDsRed1-N1 reporter plasmids and 50 nM siRNA were cotransfected into HeLa cells. EGFP-C1 encoded enhanced green fluorescence protein (GFP), while DsRed1-N1 encoded red fluorescence protein (RFP). Cells were harvested as described above and lysed in ice-cold reporter lysis buffer (Promega) containing protease inhibitor (complete, EDTA-free, 1 tablet/10 ml buffer, Roche Molecular Biochemicals). After clearing the resulting lysates by centrifugation, protein in the clear lysate was quantified by Dc protein assay kit (Bio-Rad). 120 µg of total cell lysate in 160 µl reporter lysis buffer was measured by fluorescence spectrophotometry (Photo Technology International). The slit widths were set at 4 nm for both excitation and emission. All experiments were carried out at room temperature. Fluorescence of GFP in cell lysates was detected by exciting at 488 nm and recording from 498-650 nm. The spectrum peak at 507 nm represents the fluorescence intensity of GFP. Fluorescence of RFP in the same cell lysates was detected by exciting at 568 nm and recording from 588 nm-650 nm; the spectrum peak at 583 nm represents the fluorescence intensity of RFP. The fluorescence intensity ratio of target (GFP) to control (RFP) fluorophore was determined in the presence of siRNA duplex and normalized to that observed in the presence of antisense strand siRNA. Normalized ratios less than 1.0 indicate specific interference.

Improved Dual Fluorescence Assay

HeLa cells were maintained at 37° C. in Dulbecco's modified Eagle's medium (DMEM, Invitrogen) supplemented with 10% fetal bovine serum (FBS), 100 units/ml penicillin, and 100 µg/ml streptomycin (Invitrogen). Cells were regularly passaged at subconfluence and plated 16 hr before transfection at 70% confluency. Lipofectamine (Invitrogen)-mediated transient cotransfections of reporter plasmids and siRNAs were performed in duplicate 6-well plates. A transfection mixture containing 0.16 µg pEGFP-C1 and 0.33 µg pDsRed2-N1 reporter plasmids (Clontech), various amount of siRNA (From 0.5 nM to 400 nM), and 10 µl lipofectamine in 1 ml serum-reduced OPTI-MEM (Invitrogen) was added to each well. Cells were incubated in transfection mixture for 6 hr and further cultured in antibiotic-free DMEM. Cells were treated under the same conditions without siRNA for mock experiments. At various time intervals, the transfected cells were washed twice with phosphate-buffered saline (PBS, Invitrogen), flash frozen in liquid nitrogen, and stored at −80° C. for reporter gene assays.

In improved dual fluorescence reporter assay, EGFP-C1 encoded enhanced green fluorescence protein (GFP), while DsRed2-N1 encoded red fluorescence protein (RFP2). Cells were lysed in ice-cold reporter lysis buffer (Promega) containing protease inhibitor (complete, EDTA-free, 1 tablet/10 ml buffer, Roche Molecular Biochemicals). After clearing the resulting lysates by centrifugation, protein in the clear lysate was quantified by Dc protein assay kit (Bio-Rad). 240 µg of total cell lysate in 160 µl reporter lysis buffer was measured by fluorescence spectrophotometry (Photo Technology International). The slit widths were set at 4 nm for both excitation and emission. All experiments were carried out at room temperature. Fluorescence of GFP in cell lysates was detected by exciting at 488 nm and recording from 498-650 nm. The spectrum peak at 507 nm represents the fluorescence intensity of GFP. Fluorescence of RFP2 in the same cell lysates was detected by exciting at 568 nm and recording from 588 nm-650 nm. The spectrum peak at 583 nm represents the fluorescence intensity of RFP2. The fluorescence intensity ratio of target (EGFP) to control (RFP2) fluorophore was determined in the presence of siRNA duplex and normalized to that observed in the mocked treated cells. Normalized ratios less than 1.0 indicates specific interference.

Western Blotting

Cell lysates were prepared from siRNA-treated cells and analyzed as described above. Proteins in 30 µg of total cell lysate were resolved by 10% SDS-PAGE, transferred onto a polyvinylidene difluoride membrane (PVDF membrane, Bio-Rad), and immunoblotted with antibodies against EGFP and DsRed1-N1 (Clontech). For loading control, the same membrane was also blotted with anti-actin actibody (Santa Cruz). Protein content was visualized with a BM Chemiluminescence Blotting Kit (Roche Molecular Biochemicals). The blots were exposed to x-ray film (Kodak MR-1) for various times (between 30 s and 5 min).

Psoralen Photocross-Link of siRNA Duplex

40 µg of siRNA duplex was incubated with 132 µM of a psoralen derivative, 4'-hydroxymethyl-4,5',8-trimethylpsoralen (HMT) in 200 µl DEPC-treated water at 30° C. for 30 min. Mixtures of siRNA duplex and HMT were exposed to UV 360 nm at 4° C. for 20 min, then denatured by mixing with 400 µl formamide/formaldehyde (12.5:4.5) RNA loading buffer and heating at 95° C. for 15 min. Cross-linked siRNA duplex and noncross-linked siRNA were resolved by 20% PAGE containing 7M urea in Tris-borate-EDTA. Cross-linked siRNA duplexes appeared as a population with retarded electrophoretic mobility compared to the noncross-linked species. RNAs were cut from the gel and purified by C18 reverse phase column chromatography (Waters). Purified cross-linked dsRNA and noncross-linked dsRNA were used in dual fluorescence reporter assays as described above, except that all procedures were performed in the dark to avoid light effects on psoralen. To ensure that the cross-link depended on the presence of psoralen, part of the UV 360 nm-treated mixture was also subjected to UV 254 nm at 4° C. for 20 min. Photoreverse-cross-linked siRNA migrated in 20% polyacrylamide-7 M urea gels with similar mobility to the siRNA duplex without HMT treatment.

Biotin Pull Out Assay for siRNA Isolation from Human Cells

Antisense strands of the siRNA duplex were chemically synthesized and biotin-conjugated at the 3' end (Dharmacon, Lafayette, Colo.). Synthetic oligonucleotides were deprotected and annealed with the unmodified sense strand RNA to form duplex siRNA (ss/as3'-Biotin). HeLa cells, which had been plated at 70% confluency in 100 mm dishes, were cotransfected with duplex siRNA (~600 pmole) and EGFP-C1 plasmid (1 µg) by a lipofectamine-mediated method as described above. At various times, the transfected cells were washed twice with PBS (Invitrogen) and flash frozen in liquid nitrogen. Low molecular weight RNA was isolated from the cells using a Qiagen RNA/DNA mini kit. Biotinylated siRNA was pulled out by incubating purified RNA with streptavidin-magnetic beads (60 µl) in TE buffer (10 mM Tris-HCl, pH 8.0, 1 mM EDTA) containing 1 M NaCl at room temperature for 3 h. The beads were washed 4 times with 200 µl TE buffer, resuspended in 100 µl TE buffer and split into two equal aliquots. To one aliquot (50 µl), we added 50 units of shrimp alkaline phosphatase (SAP, Roche Molecular Biochemicals) in 1×SAP buffer and incubated at 37° C. for 1 h. The SAP reaction was then stopped by heating at 65° C. for 15 min and washed 4 times with 200 µl TE buffer. The other aliquot was not treated with SAP. Aliquots of beads with or without SAP treatment were incubated with 30 units T4 polynucleotide kinase (T4 PNK, Roche Molecular Biochemicals) in 30 µl 1×PNK buffer containing 0.2 mCi γ-$^{32}$P ATP at 37° C. for 1 h. RNA products were resolved on 20% polyacrylamide-7M urea gels and $^{32}$P-labeled RNAs were detected by phosphorimaging.

Study of Duplex siRNA Stability in HeLa Cell Lysate

Unmodified or modified EGFP antisense strand siRNA were 5'-labeled with [gamma-32P] ATP (3000 ci/mM, ICN) by T4 polynucleotide kinases (New England Biolabs) at 37 C for 1 h and chase-kinased by adding 1 mM ATP at 37 C for 15 min. Free ATP and Kinase enzyme were removed by Qiagen nucleotide removal kit. Duplex siRNA were formed by annealing equal molar ratio of unmodified or modified sense strand siRNA with the 5'-32P labeled antisese strand. Duplex formation was confirmed by 20% polyacrylamide gel under native condition. 50 pmole duplex siRNA which labeled at 5' end of the antisense strand were incubated with 500 ug HeLa cytoplasmic extract in 50 ul reaction mixture containing 20 mM Hepes, pH 7.9, 100 mM KCl, 10 mM NaCl, 2 mM MgCl2, 10% glycerol. At various time points, 8 µl aliquots were mixed with 16 µl loading buffer (0.01% bromophenol blue, 0.01% xylene cyanol, 98% formaldehyde and 5 mM EDTA). The products were then denatured by heating at 95 C for 10 min and analyzed on 20% polyacrylamide gel containing 7M Urea followed by phosphorimage analysis (Fugi).

Preparation of HeLa cell cytoplasmic extract

HeLa cell cytoplasmic extract was prepared following the Dignam protocol for isolation of HeLa cell nuclei (Dignam et al., 1983). The cytoplasmic fraction was dialysed against cytoplasmic extract buffer (20 mM Hepes, pH 7.9, 100 mM KCl, 200 µM EDTA, 500 µM DTT, 500 µM PMSF, 2 mM MgCl$_2$ 10% glycerol). The extract was stored frozen at ~70° C. after quick-freezing in liquid nitrogen. The protein concentration of HeLa cytoplasmic extract varied between 4 to 5 mg/ml as determined by using a BioRad protein assay kit.

Preparation of Cap-Labeled Target RNA

For mapping of the target RNA cleavage, a 124 nucleotide transcript was generated corresponding to the EGFP between positions 195 and 297 relative to the start codon followed by the 21 nucleotide complement of the SP6 promoter sequence. The 124 nucleotide transcript was amplified from template EGFP-C1 by PCR using the 5' primer, GCC<u>TAATACGACTCACTATAGG</u>A-CCTACGGCGTGCAGTGC (SEQ ID NO:33) (T7 promoter underlined), and the 3' primer, TTG<u>ATTTAGGTGACACTATAG</u>ATGGTGCGCTCCTGG-ACGT (SEQ ID NO:34) (SP6 promoter underlined). The his-tagged mammalian capping enzyme was expressed in *E. coli* from a plasmid generously provided by Dr. Stewart Shuman and was purified to homogeneity. Guanylyl transferase labeling was performed by incubating 1 nmole transcript with 100 pmole his-tagged mammalian capping enzyme in a 100 µl capping reaction containing 50 mM Tris-HCl (pH 8.0), 5 mM DTT, 2.5 mM MgCl$_2$, 1 U/l RNasin Rnased inhibitor (promega) and [α-$^{32}$P]GTP at 37° C. for 1 hr. The reaction was chased for 30 minutes by supplementing with unlabeled GTP to a concentration of 100 µM. Cap-labeled target RNA was resolved on a 10% polyacrylamide-7M urea gel and was purified.

In Vitro Target RNA Cleavage Assay siRNA-mediated target RNA cleavage in human cytoplasmic extract was performed as described (Martinze et al., 2000, Cell 110-563) with some modifications. Cap-labeled target RNA of 124 nt was generated as set forth above. siRNA duplex was preincubated with HeLa cytoplasmic extract for 15 minutes at 37° C. prior to addition of cap-labeled target RNA. After addition of all components, final concentrations were 100 nM siRNA, 10 nM target RNA, 1 mM ATP, 0.2 mM GTP, 1 UVRNasin, 30 µg/ml creatine kinase, 25 mM creatine phosphate, and 50% 5100 extract. The cleavage reactions were further incubated for 1.5 hours and then stopped by the addition of 8 volumes of proteinase K buffer (200 nM Tris-HCl [pH 7.5], 25 mM EDTA, 300 mM NaCl, and 2% w/v SDS). Proteinase K (dissolved in 50 mM Tris-HCl [pH 8.0], 5 mM CaCl$_2$, and 50% glycerol) was added to a final concentration of 0.6 mg/ml. Reactions were extracted with phenol/chloroform/isoamyl alcohol (25:24:1) followed by chloroform alone, and RNA was precipitated with three volumes of ethanol. Samples were separated on 8% polyacrylamide-7M Urea gels.

Example XX: Specific Silencing of P-TEFb Expression by siRNA in HeLa Cells

RNAi was used to inhibit hCycT1 and CDK9 expression in cultured human (HeLa) cell lines. The short interfering RNA (siRNA) sequence targeting hCycT1 was from position 347 to 367 relative to the start codon, and the CDK9 siRNA sequence was from position 258 to 278 relative to the start codon. Using lipofectamine, HeLa cells were transfected with hCycT1 or CDK9 siRNA duplex, targeting either hCycT1 or CDK9. To analyze RNAi effects, lysates were prepared from siRNA duplex-treated cells at various times after transfection. Western blot experiments were carried out using anti-hCycT1 and anti-CDK9 antibodies. Briefly, HeLa cells were transfected with double-stranded (ds) siRNAs targeting RFP, hCycT1, or CDK9. Cells were also transfected with mutant siRNAs (hCycT1 mismatch or CDK9 mismatch) having 2 nucleotide mismatches between the target mRNA and the antisense strand of siRNA at the hypothetical cleavage site of the mRNA. Cells were harvested at various times post transfection, their protein content resolved on 10% SDS-PAGE, transferred onto PVDF membranes, and immunoblotted with antibodies against hCycT1 and CDK9. Analysis of immunoblotting experiments reveals that the siRNA targeting hCycT1 inhibited hCycT1 protein expression. siRNA targeting CDK9 was similarly specific against CDK9 expression. This RNAi effect depended on the presence of a 21-nt duplex siRNA harboring a sequence complementary to the target mRNA, but not on single stranded antisense strand siRNAs nor on an unrelated control siRNA, which targeted a coral (*Discosoma* spp.)-derived red fluorescent protein (RFP). As a specificity control, cells were also transfected with mutant siRNAs (mismatched siRNA) of hCycT1 or CDK9, which have two nucleotide mismatches between the target mRNA and the antisense strand of siRNA at the putative cleavage site of the mRNA. Mutant siRNAs showed no interference activity, indicating the specificity of the RNAi effect. Thus, the siRNAs of the present invention specifically silence the subunits of P-TEFb in HeLa cells.

Example XXI: Specific Silencing of P-TEFb by siRNA at the mRNA Level and Stability of CDK9

To determine the specificity of P-TEFb knockdown by siRNA at the mRNA level, RT-PCR was performed to reveal the effect of siRNA on the level of mRNA involved in P-TEFb expression. Briefly, HeLa cells were transfected with hCycT1 ds siRNA and CDK9 ds siRNA, harvested at various times after transfection and mRNAs extracted. One-step RT-PCR was performed, setting the specific primer for hCycT1 and CDK9 amplification. RT-PCR products were resolved in 1% agarose gel and viewed by ethidium bromide staining. Transfection of cells with siRNA duplex targeting hCycT1 (hCycT1 ds) significantly reduced hCycT1 expression, but had no effect on CDK9 mRNA.

On the other hand, transfection of cells with siRNA duplex targeted to CDK9 (CDK9 ds) significantly interfered with the expression of CDK9, but not hCycT1. These results suggested that hCycT1 knockdown did not result in decreased transcription of CDK9 mRNA. The siRNA duplex started to cause an RNAi effect as early as 6-18 hours post transfection and gradually increased with time, peaking at 30 h, and decreased between 54-66 h. The time-dependent effect of siRNA indicates that siRNAs need to be processed or assembled into an active complex with cellular factors for effective RNA interference. A time lag was also seen between the degradation of target mRNA (starting at 6 hours post siRNA transfection, as shown by semi-quantitative RT-PCR) and the half-life of the existing protein expressed by the target gene, because protein levels did not show any down-regulation until 18-30 hours post siRNA transfection. Combined with Western blot analysis, semi-quantitative RT-PCR not only confirms the specific knockdown of P-TEFb by siRNA at the mRNA level, but also suggests that forming a complex with hCycT1 is a prerequisite for maintaining the stability of CDK9 proteins in living cells. Thus, hCycT1 siRNA down-regulated hCycT1 levels by the RNAi pathway, while down-regulating CDK9 levels by promoting its degradation without affecting its gene expression at the mRNA level. This indicates that the use of hCycT1 siRNA, even without added CDK9 siRNA, is able to down regulate both P-TEFb and CDK9 activity.

Example XXII: hCycT1 and CDK9 Knockdown are not Lethal to Human Cells

To analyze the viability of cells subjected to P-TEFb gene silencing, a pEGFP-C1 reporter plasmid, harboring enhanced green fluorescent protein [GFP] under the cytomegalovirus (CMV) immediate early promoter, plus hCycT1 and CDK9 siRNAs were co-transfected into HeLa cells using lipofectamine. Briefly, HeLa cells were cotransfected by Lipofectamine™ with pEGFP-C1 reporter (GFP) plasmid and siRNAs. Four siRNA duplexes, including a control duplex targeting RFP and three duplexes targeting hCycT1, CDK9, and CDK7, were used in these experiments. Reporter gene expression was monitored at 50 hours post transfection by fluorescence imaging in living cells. Cellular shape and density were recorded by phase contrast microscopy. Reporter gene (GFP) expression, driven by cytomegalovirus (CMV) immediate early promoter, was monitored in living cells. Cellular morphology and density were monitored by phase contrast microscopy. GFP expression was not affected by hCycT1 or CDK9 knockdown. Cells with P-TEFb knockdown had normal shape and growth rate. At 50 hours post transfection, cell density reached ~90% to 100% confluency.

For comparison, cells were transfected with siRNA targeting CDK7, a well-characterized kinase required for TFIIH, an essential transcription factor, to phosphorylate the CTD of RNA pol II at the step of promoter clearance during initiation of transcription. Kin28, a protein in *Saccharomyces cerevisiae* that is equivalent to CDK7 in mammals, is an essential gene product that phosphorylates Ser5 of the CTD YSPTSPS repeat region (Komarnitsky et al. (2000), Genes Dev., 14, 2452-2460; Rodriguez et al. (2000), Mol. Cell. Biol., 20, 104-112; Schroeder et al. (2000), Genes & Dev., 14, 2435-2440) and is required to recruit the mRNA capping enzyme to the transcription machinery (Cho et al. (1997), Genes & Dev., 11, 3319-3326; McCracken et al. (1997), Genes & Dev., 11, 3306-3318; McCracken et al. (1997), Nature, 385, 357-361; Yue et al. (1997), Proc. Natl. Acad. Sci. USA, 94, 12898-12903). CDK7 is a bifunctional enzyme in larger eukaryotes, promoting both CDK activation and transcription (Harper and Elledge. (1998), Genes & Dev., 12, 285-289). As expected, reduction of CDK7 levels by RNAi led to a lower reporter (GFP) expression and an arrest in cellular growth (FIG. 4, panel d). CDK7 knockdown cells were smaller than control cells and showed blebbing (FIG. 4, panel h), indicating that unlike RNAi of P-TEFb, CDK7 gene silencing had an adverse affect on transcription, cell morphology and cell growth.

Cellular viability was next analyzed under various siRNA treatments. At various times after transfection, cell viability was assessed by trypan blue exclusion (see below). Briefly, HeLa cells were cotransfected by Lipofectamine™ with pEGFP-C1 reporter (GFP) plasmid and siRNAs (see Experimental Procedures). Four siRNA duplexes, including a control unrelated duplex and three duplexes targeting hCycT1, CDK9, and CDK7, were used in these experiments. At various times after transfection, cells floating in the medium were collected and counted in the presence of 0.2% trypan blue (see Experimental Procedures). Cells that took up dye (stained blue) were not viable. Over a 66 hours time course experiment, the rate of cell death in P-TEFb (hCycT1 or CDK9) knockdown cells was comparable to that in control cells with unrelated siRNA treatment, while CDK7 knockdown cells showed a significant increase in cell death. These results indicate that P-TEFb knockdown is not lethal to human cells, while a much more stringent threshold for CDK7 is required to maintain cell viability and growth.

Example XXIII: hCycT1 and CDK9 RNAi Inhibit HIV-1 Tat Transactivation in Human Cells A dominant paradigm for Tat up-regulation of HIV gene expression at the level of transcription elongation revolves around the ability of the Tat-TAR RNA complex to bind to P-TEFb and stimulate phosphorylation of the CTD and Spt5, thereby overriding the elongation arrest elicited by DSIF and NELF (Ping and Rana, 2001, supra; Price, 2000, supra). To test whether siRNAs that targeted sequence elements of P-TEFb would specifically block Tat transactivation, Magi cells were cotransfected with the Tat expression construct pTat-RFP and hCycT1 or CDK9 ds siRNA or as controls, antisensehCycT1 or CDK9 siRNA, mutant hCycT1 or CDK9 siRNA, or non-P-TEFb duplex siRNA. Magi, a HeLa cell line harboring a single copy of persistently transfected HIV-1 LTR-β-galactosidase gene, is programmed to express the CD4 receptor and the CCR5 coreceptor for HIV-1, making them a model cell line for measuring HIV replication (Kimpton and Emerman, 1992, supra). It was confirmed that the HIV-1 Tat-RFP fusion protein was expressed under control of the CMV early promoter in all transfected cells by Western blot, using anti-RFP antibody.

Tat-RFP strongly enhanced β-galactosidase gene expression, which is under control of the HIV-1 LTR promoter in transfected Magi cells. Tat transactivation was determined by calculating the ratio of β-galactosidase activity in pTat-RFP transfected cells to the activity in cells without pTat-RFP treatment. Inhibitory activity was determined by normalizing Tat-transactivation activity to the amount of Tat-RFP protein (represented by RFP fluorescence intensity as described in Experimental Procedures) in the presence and absence of siRNA. Briefly, twenty-four hours after pre-treating Magi cells with siRNA, they were cotransfected with pTat-RFP plasmid and various siRNAs. Cells were harvested 48 h post pTat-RFP transfection, and activity □□ of β-galactosidase in clear cell lysates was measured (see Experimental Procedures). Magi cells were cotransfected with ds siRNAs targeting hCycT1 and CDK9, with antisense (as) RNA strands, or mutant (mm) siRNAs. GFP ds siRNA was used as an unrelated control siRNA, while Tat ds siRNA, targeting the mRNA encoding Tat sequence, was used as a positive control. Means±SD of two experiments are shown. Under standard experimental conditions, Tat-RFP enhanced gene transactivation 20- to 25-fold. This activation was strongly inhibited by cotransfecting host Magi cells with the specific ds siRNAs targeting hCycT1 and CDK9, but not with antisense (as) RNA strands, mutant (mm) siRNAs or an unrelated control siRNA.

Specific RNA interference with hCycT1 and CDK9 expression in Magi cells was demonstrated by Western blot analysis. Briefly, Magi cells were co-transfected with pTat-RFP plasmid and various siRNAs. Cells were harvested at 48 hours post transfection, resolved on 10% SDS-PAGE, transferred onto PVDF membranes, and immunoblotted with antibodies against hCycT1 and CDK9. RNAi activities in Magi cells treated with antisense (as) strands of hCycT1 and CDK9 siRNAs, cells treated with ds siRNA targeting hCycT1 and CDK9, cells treated with mutant hCycT1 siRNA (hCycT1 mm) or mutant CDK9 siRNA (CDK9 mm) were examined. GFP ds siRNA was used as an unrelated control, while Tat ds RNAi was used to target mRNA encoding Tat. The inhibition of Tat transactivation correlated well with the knockdown of hCycT1 and CDK9 protein levels by the hCycT1 and CDK9 siRNAs. Syncytia formation and LTR activation were reduced in hCycT1 ds siRNA-treated cells. From these results, it can be concluded that siRNA targeting P-TEFb can inhibit Tat-transactivation in human cells without affecting cellular viability, thus making siRNA targeting P-TEFb an excellent candidate for treatment of patients infected with HIV.

Example XXIV: hCycT1 and CDK9 RNAi Inhibit HIV-1 Infectivity

The next question addressed was whether targeting the human P-TEFb complex by RNAi inhibited HIV replication. To investigate this question, HeLa-CD4-LTR/β-galactosidase (Magi) cells were transfected with homologous and mismatched siRNAs directed against hCycT1 or CDK9 and 16 hours later infected the Magi cells with various concentrations of $HIV_{NL\text{-}GFP}$, an infectious molecular clone of HIV-1. HIV-1 Tat-mediated transactivation of the LTR led to β-galactosidase production that was quantified 36 hours post-infection. Briefly, LTRM-galactosidase (Magi) cells transfected with homologous and mismatched siRNAs directed against CycT1 or CDK9. Cells were also mock transfected without siRNA or transfected with an unrelated ds siRNA against the RFP sequence. Sixteen hours later, cells were infected with NL-GFP, an infectious molecular clone of HIV-1. Cells infected with virus and not treated with oligofectamine were examined. HIV-1 Tat-mediated transactivation of the LTR led to v-galactosidase production, which was quantified 36 hours post-infection. Cells treated with ds siRNA targeting GFP-Nef and targeting the mRNA encoding Tat sequence served as positive controls. These controls previously showed decreased levels of β-galactosidase activity and viral infectivity (Jacque et al. 2002 Nature 418:435-8).

ds siRNA directed against hCycT1 or CDK9 inhibited viral infectivity. Doubling dilutions of the inoculums are consistent with an 8-fold decrease in viral infectivity. Control experiments using siRNA duplexes containing mismatched sequences (see Experimental Procedures) and an unrelated ds siRNA against the RFP sequence showed no antiviral activities. Consistent with our previous results (Jacque et al., 2002, supra), siRNA targeting GFP-Nef and Tat led to an 8-fold decrease in viral infectivity. No significant toxicity or cell death was observed during these experiments, suggesting further that P-TEFb knockdown was not lethal. These results demonstrate that HIV infectivity can be modulated by siRNAs targeting CycT1 or CDK9, both components of P-TEFb, indicating that the use of siRNA targeting either subunit is a viable treatment for patients with HIV.

Example XXV: Method of Treating Cancer by Inhibiting P-TEFb

An intriguing finding is that genes linked to embryonic development and showing down-regulation in P-TEFb knockdown cells (as described above) also participate in tumorogenesis and metastasis. Dysfunction of protein tyrosine kinases or aberrations in key components of the signaling pathways they activate can lead to severe pathologies such as cancer, diabetes and cardiovascular disease. For example, overexpression of EGFR has been implicated in mammary carcinomas, squamous carcinomas and glioblastomas (Schlessinger (2002), Cell, 110, 669). AXL, another receptor tyrosine kinase, was originally identified with oncogenic potential and transforming activity in myeloid leukemia cells (Burchert et al. (1998), Oncogene, 16, 3177-3187). Elevated TGF-beta levels can contribute to tumor progression and metastasis (Attisano and Wrana, 2002, supra; Massague, 2000, supra). Lysyl oxidase (LOX class II), an extracellular matrix remodeling enzyme, is up-regulated in prostatic tumor, cutaneous and uveal cell lines (Kirschmann et al. (2002), Cancer Res., 62, 4478-4483). Down-regulating these genes by P-TEFb knockdown using siRNA targeting CDK9 or CycT1 thus provides a new therapeutic strategy for inhibiting tumorigenesis and metastasis.

Genes involved in mediating progression through the cell cycle and as checkpoints in cancer were regulated by P-TEFb. Cyclin G1 is the downstream target of the P53 pathway and plays a role in G2/M arrest, damage recovery and growth promotion after cellular stress (Kimura et al. (2001), Oncogene, 20, 3290-3300). Cyclin D, a cell-cycle regulatory protein essential for G1/S transition, has been identified as a potential transforming gene in lymphoma (Motokura and Arnold (1993), Curr. Opin. Genet. Dev., 3, 5-10). Misregulation of the activity of its partner, CDK4/6, by overexpression of Cyclin D leads to hyperproliferative defects and tumor progression (Ortega et al. (2002), Biochim. Biophys. Acta, 1602, 73-87). Several marker genes in cancer cells (class V) are also regulated by P-TEFb. For example, breast cancer-specific protein 1 (BCSG1) is overexpressed in advanced, infiltrating breast cancer and colorectal tumors (Lu et al. (2001), Oncogene, 20, 5173-5185). Another example is soluble urokinase plasminogen activator receptor (SUPAR), which is present in high concentrations in cystic fluid form ovarian cancer, tumor tissue of primary breast cancer, and gynecological cancer (Riisbro et al. (2002), Clin. Cancer. Res., 8, 1132-1141; Wahlberg et al. (1998), Cancer Res., 58, 3294-3298). Although the functions of these marker genes are still unknown, their high correlation with cancer has been used for prognosis in cancer therapy. The down-regulation of cyclin D and cancer marker genes by P-TEFb knockdown offers a method of cancer therapy. Briefly, a therapeutically effective amount of one of more of the pharmaceutical compositions of the invention is administered to a patient having a disorder characterized by unwanted or aberrant cellular proliferation as described herein.

Example XXVI: Specific Silencing of P-TEFb In Vivo

The effect of downregulating P-TEFb in vivo is assayed by administering siRNA targeted to CDK9 and/or CycT1 in an animal model. Any appropriate animal model can be used, for example, including but not limited to, rodent cancer models such as those available from the Mouse Models of Human Cancers Consortium (MMHCC) Repository (NCI, Frederick, Md.); the Oncomouse™ as described in U.S. Pat. Nos. 4,736,866, 5,087,571 and 5,925,803 (Taconic); or rodent or non-human primate models of HIV infection, such as the SCID-hu mouse.

For example, in a mouse model, the siRNA is administered using hydrodynamic transfection as previously described (McCaffrey, 2002, supra; Liu, 1999, supra), by intravenous injection into the tail vein (Zhang, 1999, supra); or by viral delivery (Xia, 2002, supra). At various time points after administration of the selected siRNA, mRNA levels for CDK9 and/or CycT1 can be measured. Additionally, the siRNA can be labeled, and the half-life of the siRNA molecules can be tracked using methods known in the art. Using electroporation, RNase III-prepared siRNA can be delivered into the post-implantation mouse embryos. 0.03:g-0.3:g siRNA can efficiently silence reporter gene expression in different regions of the neural tube or other cavities of the mouse embryo (Calegari (2002), supra). Using rapid injection of the siRNA-containing physiological solution into the tail vein of postnatal mice, 0.5-5:g siRNA can cause 36±17%-88%±3% inhibition of target gene expression. The effect of RNAi is siRNA dose-dependent and can persist for approximately 4 days after siRNA delivery (Lewis (2002), supra). By direct injection, 5-40:g siRNA can be used to silencing target gene expression in the liver, which is central to metabolism (Lewis (2002), supra; McCaffrey (2002), supra).

Any appropriate parameter can be observed to investigate the effect of P-TEFb expression. For example, changes in gene expression can be determined, such as changes in the expression of any one or more of the genes listed herein. In a mouse cancer model, appropriate parameters can include survival rates, tumor growth, metastasis, etc. In a simian HIV model, for instance parameters that can be determined include, but are not limited to, infectivity, viral load, survival rates, and rates and severity of secondary AIDS-associated illnesses.

Such models may also be useful for evaluating various gene delivery methods and constructs, to determine those that are the most effective, e.g., have the greatest effect, or have a desirable half-life or toxicity profile, for instance.

Example XXVII: Specific Silencing of hSpt5 Expression by siRNA in HeLa Cells

To inhibit hSpt5 expression in a cultured human cell line using RNAi, siRNA targeting an hSpt5 sequence from position 407 to 427 relative to the start codon was designed. Magi cells were then transfected with hSpt5 duplex siRNA using Lipofectamine (Invitrogen). To evaluate the effects of hSpt5 RNAi, total cell lysates were prepared from siRNA-treated cells harvested at various time points after transfection. hSpt5 mRNA or protein levels were then analyzed by RT-PCR or western blot using anti-hSpt5 antibodies, respectively. These experiments showed that cells transfected hSpt5 siRNA had significantly lowered hSpt5 mRNA and protein expression, indicating that RNAi of hSpt5 had occurred successfully. This knockdown effect was dependent on the presence of a 21-nt siRNA duplex harboring a sequence complementary to the mRNA target. Mock-treated (no siRNA), single-stranded antisense hSpt5 siRNA, mismatched hSpt5 duplex siRNA, containing two nucleotide mismatches between the target mRNA and siRNA antisense strand at the putative cleavage site of the target mRNA did not affect hSpt5 mRNA or proteins levels. This suggested that hSpt5 knockdown was specific to duplex siRNA exactly complementary to the hSpt5 mRNA target. In evaluating either mRNA or protein levels, human Cyclin T1 (hCycT1) was used as an internal control, showing that the effects of hSpt5 siRNA were specific to hSpt5 and did not effect hCycT1 mRNA or protein levels. Taken together, these results suggested that hSpt5 knockdown was sequence specific and led to significantly decreased hSpt5 mRNA and proteins levels.

Example XXVIII: Specific Silencing of Spt5 by siRNA at the mRNA Level

To determine the specificity of Spt5 knockdown by siRNA at the mRNA level, RT-PCR is used to reveal the effect of siRNA on the level of mRNA involved in Spt5 expression. Briefly, HeLa cells are transfected with Spt5 ds siRNA, harvested at various times after transfection and mRNAs are extracted. One-step RT-PCR is performed, using specific primers for Spt5 amplification. A control is run concurrently using primers specific for another, unrelated gene, e.g., CDK9, CycT1, or actin. RT-PCR products are resolved in 1% agarose gel and viewed by ethidium bromide staining. Changes in Spt5 mRNA levels with time, while the levels of mRNA of the unrelated gene remain unaltered, indicate that the effect of the siRNA is specific.

Example XXIX: Viability of Human Cells with Spt5 Knockdown

Cellular viability under various siRNA treatments was analyzed by trypan blue exclusion. Knowing that the kinetics of hSpt5 peaked at 42-54 h post-transfection, the viability of cells during an hSpt5 knockdown time course experiment could be evaluated. Cell viability was assessed using trypan blue exclusion at various times after transfection of various siRNAs. During the 66 h time course experiment, the number of non-viable hSpt5 knockdown cells observed was comparable to mock-treated cells. Cells transfected with single-stranded antisense hSpt5 siRNA or mismatched hSpt5 duplex siRNA that did not show hSpt5 knockdown also showed minimal changes in cell viability. The positive control for this experiment was human capping enzyme (HCE), which is a bifunctional triphophsatase-guanylyl-transferase required for capping mRNA (reviewed in Bentley et al., 2002 Curr Opin Cell Biol 14:336-342). HCE is very likely to be essential for cell viability as the HCE homolog cel-1 in C. elegans is essential (Srinivasan et al., 2003 J Biol Chem 278:14168-14173). In contrast to hSpt5 knockdown cells, HCE knockdown cells showed a significant increase in cell death over the course of the knockdown experiment. These results indicated that hSpt5 knockdown was not lethal to human cells, while a much more stringent requirement for HCE expression was essential for cell viability.

Cell viability in vivo under siRNA treatment can also be evaluated by fluorescence imaging. pEGFP-C1 reporter plasmid (harboring enhanced green fluorescent protein [GFP]) and siRNAs are cotransfected into HeLa cells using Lipofectamine™. Briefly, HeLa cells are cotransfected by Lipofectamine™ with pEGFP-C1 reporter (GFP) plasmid and siRNAs. In general, four siRNA duplexes, including a control duplex targeting RFP and duplexes targeting Spt5 are used in these experiments. Reporter gene expression is monitored at 50 hours post transfection by fluorescence imaging in living cells. Cellular shape and density are recorded by phase contrast microscopy.

Example XXX: hSpt5 RNAi Inhibits HIV-1 Tat Transactivation in Human Cells

A dominant paradigm for Tat up-regulation of HIV gene expression at the level of transcription elongation revolves around the ability of the Tat-TAR RNA complex to bind to P-TEFb and stimulate phosphorylation of the CTD and Spt5, thereby overriding the elongation arrest elicited by DSIF and NELF (Ping and Rana (2001), supra; Price (2000), supra).

To examine whether hSpt5 was required for HIV-1 Tat transactivation in vivo, Tat transactivation during hSpt5 knockdown in Magi cells was monitored. Magi cells are a HeLa cell line harboring a stably integrated single copy of the HIV-1 5' LTR-β-galactosidase gene. These cells are also genetically programmed to express the CD4 receptor as well as CCR5 coreceptor for HIV-1 infection (Kimpton and Emerman, 1992 J Virol 66:2232-2239); see below). In this experiment, Magi cells were co-transfected with Tat expression plasmid pTat-RFP and hSpt5 duplex siRNA. Co-transfection with Tat siRNA was used as a positive control for inhibition of Tat transactivation while single-stranded antisense hSpt5 siRNA and mismatched siRNA were used as negative controls. Tat transactivation and protein levels were evaluated by harvesting cells 48 h post transfection, which was within the timeframe that hSpt5 knockdown peaked. Expression of HIV-1 Tat-RFP under the control of the CMV early promoter was confirmed by western blot using anti-RFP antibody and RFP fluorescence measurement on a fluorescence spectrophotometer (data not shown). In addition, immunoblot analysis confirmed that hSpt5 siRNA specifically inhibited hSpt5 protein expression in the absence and presence of HIV-1 Tat protein in Magi cells (data not shown).

Tat-RFP enhances the expression of genes that are under the control of the HIV-1 5' LTR promoter. In this experiment, Tat transactivation was measured by assaying the β-galactosidase activity resulting from expression of the β-galactosidase gene under the HIV-1 5' LTR promoter. To quantify the effects of various siRNAs on HIV-1 Tat transactivation, the ratio between β-galactosidase activity in cells transfected with pTat-RFP (with or without siRNAs) and mock-treated cells not transfected with pTat-RFP was determined. In Magi cells, Tat-RFP strongly stimulates the expression of β-galactosidase, represented by a 13-fold increase in Tat transactivation. On the other hand, Tat transactivation was strongly inhibited in cells transfected with Tat siRNA, as previously shown (Surabhi and Gaynor 2002 J Virol 76:12963-12973). Tat transactivation was similarly inhibited when cells were transfected with hSpt5 duplex siRNA, exhibiting only ~30% of the Tat transactivation observed with Tat-RFP alone. Neither antisense hSpt5 siRNA nor mismatched hSpt5 siRNA showed any effect on Tat transactivation. These results indicated hSpt5 knockdown caused by siRNA specifically targeting hSpt5 mRNA inhibited HIV-1 Tat transactivation in human cells. These results strongly supported an important role for hSpt5 in Tat transactivation in vivo and suggested that RNAi of hSpt5 had the potential to inhibit HIV-1 replication.

Example XXXI: hSpt5 siRNAs Inhibit hSpt5 Protein Expression in the Presence or Absence of Tat Expression Specific RNA interference with Spt5 expression in Magi cells was demonstrated by Western blot analysis. Briefly, Magi cells were co-transfected with pTat-RFP plasmid and various siRNAs. Cells were harvested at 48 hours post-transfection, resolved on 10% SDS-PAGE, transferred onto PVDF membranes, and immunoblotted with antibodies against Spt5 or hCycT1. RNAi activities in Magi cells treated with antisense (AS) strands of Spt5 siRNAs and in cells treated with ds siRNA targeting Spt5 were examined. RNAi activities in cells treated with mismatch Spt5 (hCycT1 mm) siRNAs with two mismatches were also examined. From the results, it can be concluded that siRNA targeting hSpt5 can inhibit hSpt5 protein expression in the presence or absence of Tat protein, making siRNA targeting hSpt5 an excellent candidate compound for treatment of patients infected with HIV.

Example XXXII: RNAi Inhibition of HIV-1 Infectivity

Since hSpt5 knockdown effectively inhibited Tat transactivation, we next determined whether hSpt5 knockdown could inhibit HIV-1 replication. To evaluate the effect of hSpt5 knockdown on HIV-1 replication, a double siRNA transfection protocol was used to maximize the knockdown efficiency of hSpt5 during HIV-1 infection. Magi cells were transfected with siRNA directed against hSpt5. Cells mock transfected without siRNA, or transfected with single-stranded antisense hSpt5 siRNA or mismatch hSpt5 siRNA were used as negative controls. Transfection with Nef siRNA was used as a positive control. 24 h after the first transfection, a second siRNA transfection was performed. 24 h later, doubly transfected cells were infected with various concentrations of $HIV_{NL-GFP}$, an infectious molecular clone of HIV-1. Knockdown of hSpt5 protein levels was then evaluated 48 h post infection in doubly transfected cells. An even larger decrease in hSpt5 protein levels was observed in doubly transfected cells as compared to singly transfected cells, suggesting that more robust knockdown of gene expression can be achieved using this double transfection method.

HIV-1 Tat-mediated transactivation of the 5' LTR occurring in cells infected with virus led to β-galactosidase production, which was also quantified 48 h post-infection. In this single-cycle replication assay for evaluating HIV-1 replication, β-gal activity reflected the activity of reverse transcriptase and viral replication of varying amounts of viral inoculum. Therefore, changes in β-gal activity could be directly correlated to changes in the efficacy of HIV replication. The positive siRNA control targeting HIV Nef showed decreased levels of β-gal activity and viral infectivity, as shown previously (FIG. 32; (Jacque et al., 2002 Nature 418:435-438). Double-stranded siRNA directed against hSpt5 showed a similar decrease in β-gal activity when compared with Nef knockdown. This observed decrease was equivalent to the β-gal activity measured when using 32 times less viral inoculum with mock-treated cells, indicating that hSpt5 knockdown had significantly reduced HIV replication. Control experiments using hSpt5 single-stranded antisense or mismatched duplex siRNA duplexes showed no antiviral activities. In addition, no significant toxicity or cell death was observed during these experiments, suggesting that hSpt5 knockdown was not lethal even in the context of HIV-1 infection. These results demonstrated that HIV replication was modulated by siRNAs targeting hSpt5, further establishing an important role for hSpt5 in Tat transactivation and HIV-1 replication in vivo.

Example XXXIII: Specific Silencing of TEFs In Vivo

The effect of downregulating TEFs in vivo is assayed by administering siRNA targeted to one or more TEFs, e.g. Spt4, Spt5, and/or Spt6, in an animal model. The siRNA is administered using hydrodynamic transfection as previously described (McCaffrey (2002), supra; Liu (1999), supra), by intravenous injection into the tail vein (Zhang (1999), supra); or by viral delivery (Xia (2002), supra). At various time points after administration of the selected siRNA, mRNA levels for one or more TEFs, e.g., Spt4, Spt5, and/or Spt6 are measured. Additionally, the siRNA can be labeled, and the half life of the siRNA molecules is tracked using methods known in the art. Using electroporation, RNase III-prepared siRNA can be delivered into the post-implantation mouse embryos. 0.03:g-0.3:g siRNA can efficiently silence reporter gene expression in different regions of the neural tube or other cavities of the mouse embryo (Calegari (2002), supra). Using rapid injection of the siRNA-containing physiological solution into the tail vein of postnatal mice, 0.5-5:g siRNA can cause 36±17%-88%±3% inhibition of target gene expression. The effect of RNAi is siRNA dose-dependent and can persist for approximately 4 days after siRNA delivery (Lewis (2002), supra). By direct injection, 5-40:g siRNA can be used to silencing target gene expression in the liver, which is central to metabolism (Lewis (2002), supra; McCaffrey (2002), supra).

Experimental Procedures for Examples XX-XXXIII siRNA Preparation

Design of siRNAs Against CDK9/CycT1 The targeted region in the mRNA, and hence the sequence of CycT1 or CDK9-specific siRNA duplexes was designed following the guidelines provided by Dharmacon (Lafayette, Colo.). Briefly, starting 100 bases downstream of the start codon, the first AA dimer was located and the next 19 nucleotides were then recorded following the AA dimer.

Criteria were set such that the guanosine and cytidine content (G/C content) of the AA-N19 21 base-sequence must be less than 70% and greater than 30%. The search continued downstream until the conditions were met. The 21-mer sequence was subjected to a BLAST search against the human genome/NCBI EST library to ensure only the desired gene was targeted. The siRNA sequence targeting hCycT1 was from position 347-367 relative to the start codon. The siRNA sequence targeting CDK9 was from position 258-278 relative to the start codon. siRNA sequences used in our experiments were: hCycT1 ds (5'-UCCCUUCCUGAUACUAGAAdTdT-3') (SEQ ID NO:3); hCycT1 mm (5'-UCCCUUCC<u>GU</u>AUACUAGAAdTdT-3') (SEQ ID NO:4); CDK9 ds (5'-CCAAAGCUUCCCCC-UAUAAdTdT-3') (SEQ ID NO:5); CDK9 mm (5'-CCAAAGCU<u>CU</u>CCCCUAUAAdTdT-3') (SEQ ID NO:6); CDK7 ds (5'-UUGGUCUCCUUGAUGCUUUdTdT-3') (SEQ ID NO:17); Tat ds (5'-GAAACGUA-GACAGCGCAGAdTdT-3') (SEQ ID NO:18); GFP ds (5'-GCAGCACGACUUCUUCAAGdTdT-3') (SEQ ID NO:19); and RFP ds (5'-GUGG-GAGCGCGUGAUGAACdTdT-3') (SEQ ID NO:20). Underlined residues represent the mismatched sequence to their targets.

hCycT1 contains an amino-terminal cyclin box motif (amino acids 1-298) that is conserved in the cyclin type protein family, a putative coiled-coil motif (amino acids 379-430) and a histidine-rich motif (amino acids 506-530). The hCycT1 sequence containing amino acids 1-303 is sufficient to form complexes with Tat-TAR and CDK9, as CDK9 binds to the cyclin box (amino acids 1-250) of CycT1. A Tat:TAR recognition motif (TRM) in the hCycT1 sequence that spans amino acids 251-272 is necessary for forming complex with Tat and TAR. Residues 252-260 of hCycT1 have been demonstrated to interact with the TAR RNA loop, suggesting that amino acids 261-272 are involved in interaction with Tat core domain. A critical cysteine (amino acids 261) has been identified as a absolutely requiring residue for the Tat and hCycT1 interaction. The targeted region in the mRNA and hence the sequence of hCycT1-specific siRNA duplexes can be designed targeting to the Cyclin box region or the region for Tat-TAR interaction. Using the guidelines provided by Dharmacon (Lafayette, Colo.) as discussed above, other potential siRNA target sequences include the following: relative to the start codon, the siRNA sequences targeting hCycT1 can be from position 238-278, 502-522, 758-778, 769-789 etc. Based on the guidelines of Dharmacon as discussed above, additional siRNA sequences suitable for targeting CDK9 can be from position 220-240, 258-278, 379-399 relative to the start codon.

Design of siRNAs Targeting Spt5

The targeted region in the mRNA, and hence the sequence of Spt5-specific siRNA duplexes, was designed following the guidelines provided by Dharmacon (Lafayette, Colo.). Briefly, beginning 100 bases downstream of the start codon, the first AA dimer was located and then the next 19 nucleotides following the AA dimer were recorded. Ideally, the guanosine and cytidine content (G/C content) of the AA-N19 21 base-sequence would be less than 70% and greater than 30%. The search was continued downstream until the conditions were met. The 21-mer sequence was subjected to a BLAST search against the human genome/NCBI EST library to ensure only the desired gene was targeted. The siRNA sequence targeting hSpt5 was from position 407-427 relative to the start codon. siRNA sequences used in the experiments described herein were: hSpt5ds (5'-AACTGGGCGAGTATTACATGAdTdT-3') (SEQ ID NO: 8); h Spt5 mm (5'-AACTGGGCG GATATTACATGAdTdT-3') (SEQ ID NO: 9); Tat ds (5'-GAAACGUAGACAGCGCAGAdTdT-3') (SEQ ID NO: 18); GFP ds (5'-GCAGCACGACUUCUUCAAGdTdT-3') (SEQ ID NO: 19); and RFP ds (5'-GUGG-GAGCGCGUGAUGAACdTdT-3') (SEQ ID NO: 20). Underlined residues represent the sequences mismatched to their targets.

Using the guidelines provided by Dharmacon (Lafayette, Colo.) as discussed above, other potential siRNA sequences targeting Spt5, as well as siRNA sequences targeting Spt4 or Spt6, can be identified.

SiRNA Synthesis and Maintenance 21-nt RNAs were chemically synthesized as 2' bis(acetoxyethoxy)-methyl ether-protected oligos by Dharmacon (Lafayette, Colo.). Synthetic oligonucleotides were deprotected, annealed to form dsRNAs and purified according to the manufacturer's recommendation. Successful duplex formation was confirmed by 20% non-denaturing polyacrylamide gel electrophoresis (PAGE). All siRNAs were stored in DEPC (0.1% diethyl pyrocarbonate)-treated water at −80° C.

REFERENCES

Bass, B. L. (2000). Double-stranded RNA as a template for gene silencing. Cell 101, 235-238.

Bernstein, E., Caudy, A. A., Hammond, S. M., and Hannon, G. J. (2001). Role for a bidentate ribonuclease in the initiation step of RNA interference. Nature 409, 363-366.

Chiu, Y. L., and Rana, T. M. (2002). RNAi in human cells: basic structural and functional features of small interfering RNA. Mol. Cell 10, 549-561.

Cimino, G. D., Gamper, H. B., Isaacs, S. T., and Hearst, J. E. (1985). Psoralens as photoactive probes of nucleic acid structure and function: organic chemistry, photochemistry, and biochemistry. Annu Rev Biochem 54, 1151-1193.

Cogoni, C., and Macino, G. (1999). Gene silencing in *Neurospora crassa* requires a protein homologous to RNA-dependent RNA polymerase. Nature 399, 166-169.

Cogoni, C., and Macino, G. (2000). Post-transcriptional gene silencing across kingdoms. Curr Opin Genet Dev 10, 638-643.

Dalmay, T., Hamilton, A., Rudd, S., Angell, S., and Baulcombe, D. C. (2000). An RNA-dependent RNA polymerase gene in *Arabidopsis* is required for posttranscriptional gene silencing mediated by a transgene but not by a virus. Cell 101, 543-553.

Dignam, J. D., Lebovitz, R. M., and Roeder, R. G. (1983). Accurate transcription initiation by RNA polymerase II in a soluble extract from isolated mammalian nuclei. Nucleic Acids Res. 11, 1475-1489.

Elbashir, S. M., Harborth, J., Lendeckel, W., Yalcin, A., Weber, K., and Tuschl, T. (2001a). Duplexes of 21-nucleotide RNAs mediate RNA interference in cultured mammalian cells. Nature 411, 494-498.

Elbashir, S. M., Lendeckel, W., and Tuschl, T. (2001b). RNA interference is mediated by 21- and 22-nucleotide RNAs. Genes Dev 15, 188-200.

Elbashir, S. M., Martinez, J., Patkaniowska, A., Lendeckel, W., and Tuschl, T. (2001c). Functional anatomy of siRNAs for mediating efficient RNAi in *Drosophila melanogaster* embryo lysate. Embo J 20, 6877-6888.

Fire, A., Xu, S., Montgomery, M. K., Kostas, S. A., Driver, S. E., and Mello, C. C. (1998). Potent and specific genetic interference by double-stranded RNA in *Caenorhabditis elegans*. Nature 391, 806-811.

Grishok, A., Tabara, H., and Mello, C. C. (2000). Genetic requirements for inheritance of RNAi in *C. elegans*. Science 287, 2494-2497.

Haaima, G., Hansen, H. F., Christensen, L., Dahl, O., and Nielsen, P. E. (1997). Increased DNA binding and sequence discrimination of PNA oligomers containing 2,6-diaminopurine. Nucleic Acids Res. 25, 4639-4643.

Hamilton, A., Voinnet, O., Chappell, L., and Baulcombe, D. (2002). Two classes of short interfering RNA in RNA silencing. EMBO J. 21, 4671-4679.

Hamilton, A. J., and Baulcombe, D. C. (1999). A species of small antisense RNA in posttranscriptional gene silencing in plants. Science 286, 950-952.

Hammond, S. M., Bernstein, E., Beach, D., and Hannon, G. J. (2000). An RNA-directed nuclease mediates post-transcriptional gene silencing in *Drosophila* cells. Nature 404, 293-296.

Hammond, S. M., Caudy, A. A., and Hannon, G. J. (2001). Post-transcriptional gene silencing by double-stranded RNA. Nat Rev Genet 2, 110-119.

Hearst, J. E., Isaacs, S. T., Kanne, D., Rapoport, H., and Straub, K. (1984). The reaction of the psoralens with deoxyribonucleic acid. Q Rev Biophys 17, 1-44.

Kanne, D., Straub, K., Rapoport, H., and Hearst, J. E. (1982). Psoralen-deoxyribonucleic acid photoreaction. Characterization of the monoaddition products from 8-methoxypsoralen and 4,5'8-trimethylpsoralen. Biochemistry 21, 861-871.

Kennerdell, J. R., and Carthew, R. W. (1998). Use of dsRNA-mediated genetic interference to demonstrate that frizzled and frizzled 2 act in the wingless pathway. Cell 95, 1017-1026.

Ketting, R. F., and Plasterk, R. H. (2000). A genetic link between co-suppression and RNA interference in *C. elegans*. Nature 404, 296-298.

Lipardi, C., Wei, Q., and Paterson, B. M. (2001). RNAi as random degradative PCR: siRNA primers convert mRNA into dsRNAs that are degraded to generate new siRNAs. Cell 107, 297-307.

Lipson, S. E., Cimino, G. D., and Hearst, J. E. (1988). Structure of M1 RNA as determined by psoralen cross-linking. Biochemistry 27, 570-575.

Matzke, M., Matzke, A. J., and Kooter, J. M. (2001). RNA: guiding gene silencing. Science 293, 1080-1083.

Mourrain, P., Beclin, C., Elmayan, T., Feuerbach, F., Godon, C., Morel, J. B., Jouette, D., Lacombe, A. M., Nikic, S., Picault, N., et al. (2000). *Arabidopsis* SGS2 and SGS3 genes are required for posttranscriptional gene silencing and natural virus resistance. Cell 101, 533-542.

Neenhold, H. R., and Rana, T. M. (1995). Major groove opening at the HIV-1 Tat binding site of TAR RNA evidenced by a rhodium probe. Biochemistry 34, 6303-6309.

Nishikura, K. (2001). A short primer on RNAi: RNA-directed RNA polymerase acts as a key catalyst. Cell 107, 415-418.

Nykanen, A., Haley, B., and Zamore, P. D. (2001). ATP requirements and small interfering RNA structure in the RNA interference pathway. Cell 107, 309-321.

Parrish, S., Fleenor, J., Xu, S., Mello, C., and Fire, A. (2000). Functional anatomy of a dsRNA trigger: differential requirement for the two trigger strands in RNA interference. Mol Cell 6, 1077-1087.

Sharp, P. A. (2001). RNA interference—2001. Genes Dev 15, 485-490.

Sijen, T., Fleenor, J., Simmer, F., Thijssen, K. L., Parrish, S., Timmons, L., Plasterk, R. H., and Fire, A. (2001). On the role of RNA amplification in dsRNA-triggered gene silencing. Cell 107, 465-476.

Sijen, T., and Kooter, J. M. (2000). Post-transcriptional gene-silencing: RNAs on the attack or on the defense? Bioessays 22, 520-531.

Smardon, A., Spoerke, J. M., Stacey, S. C., Klein, M. E., Mackin, N., and Maine, E. M. (2000). EGO-1 is related to RNA-directed RNA polymerase and functions in germline development and RNA interference in *C. elegans*. Curr Biol 10, 169-178.

Stark, G. R., Kerr, I. M., Williams, B. R., Silverman, R. H., and Schreiber, R. D. (1998). How cells respond to interferons. Ann Rev Biochem 67, 227-264.

Thompson, J. F., and Hearst, J. E. (1983). Structure of *E. coli* 16S RNA elucidated by psoralen crosslinking. Cell 32, 1355-1365.

Turner, S., and Noller, H. F. (1983). Identification of sites of 4'-(hydroxymethyl)-4,5',8-trimethoxylpsoralen crosslinking in *Escherichia coli* 23S ribosomal ribonucleic acid. Biochemistry 22, 4159-4164.

Tuschl, T. (2001). RNA interference and small interfering RNAs. Chembiochem Europ J Chem Biol 2, 239-245.

Tuschl, T., Zamore, P. D., Lehmann, R., Bartel, D. P., and Sharp, P. A. (1999). Targeted mRNA degradation by double-stranded RNA in vitro. Genes Dev 13, 3191-3197.

Waterhouse, P. M., Wang, M. B., and Finnegan, E. J. (2001). Role of short RNAs in gene silencing. Trends Plant Sci 6, 297-301.

Weeks, K. M., and Crothers, D. M. (1991). RNA recognition by Tat-derived peptides: Interaction in the major groove? Cell 66, 577-588.

Weeks, K. M., and Crothers, D. M. (1993). Major Groove Accessibility of RNA. Science 261, 1574-1577.

Yang, D., Lu, H., and Erickson, J. W. (2000). Evidence that processed small dsRNAs may mediate sequence-specific mRNA degradation during RNAi in *Drosophila* embryos. Curr Biol 10, 1191-1200

Zamore, P. D., Tuschl, T., Sharp, P. A., and Bartel, D. P. (2000). RNAi: double-stranded RNA directs the ATP-dependent cleavage of mRNA at 21 to 23 nucleotide intervals. Cell 101, 25-33.

Hutvagner, G., and Zamore, P. D. (2002). A MicroRNA in a Multiple-Turnover RNAi Enzyme Complex. Science 1,1.

Kirnos, M. D., Khudyakov, I. Y., Alexandrushkina, N. I., and Vanyushin, B. F. (1977). 2-aminoadenine is an adenine substituting for a base in S-2L cyanophage DNA. Nature 270, 369-370.

Luy, B., and Marino, J. P. (2001). Measurement and application of 1H-19F dipolar couplings in the structure determination of 2'-fluorolabeled RNA. J. Biolmol. NMR 20, 39-47.

Luytena, I., and Herdewijna, P. (1998). Hybridization properties of base-modified oligonucleotides within the double and triple helix motif. Eur. J. Med. Chem. 33, 515-576.

Majlessi, M., Nelson, N. C., and Becker, M. M. (1998). Advantages of 2'-O-methyl oligoribonucleotide probes for detecting RNA targets. Nucleic Acids Res. 26, 2224-2229.

Martinez, J., Patkaniowska, A., Urlaub, H., Luhrmann, R., and Tuschl, T. (2002). Single-stranded antisense siRNAs guide target RNA cleavage in RNAi. Cell 110, 563-574.

McManus, M. T., and Sharp, P. A. (2002). Gene silencing in mammals by small interfering RNAs. Nat. Rev. Genet. 3, 737-747.

Provost, P., Dishart, D., Doucet, J., Frendewey, D., Samuelsson, B., and Radmark, 0. (2002). Ribonuclease activity and RNA binding of recombinant human Dicer. EMBO J. 21, 5864-5874.

Saenger, W., ed. (1984). Principles of Nucleic Acid Structure (New York, Springer-Verlag).

Stein, C. A. (1996). Phosphorothioate antisense oligodeoxynucleotides: questions of specificity. Trends Biotechnol. 14, 147-149.

Stein, P., Svoboda, P., Anger, M., and Schultz, R. M. (2003). RNAi: Mammalian oocytes do it without RNA-dependent RNA polymerase. RNA 9, 187-192.

Zamore, P. D. (2001). RNA interference: listening to the sound of silence. Nat. Struct. Biol. 8, 746-750.

Zhang, H., Kolb, F. A., Brondani, V., Billy, E., and Filipowicz, W. (2002). Human Dicer preferentially cleaves dsRNAs at their termini without a requirement for ATP. EMBO J. 21, 5875-5885.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A small interfering RNA (siRNA), comprising a sense strand and an antisense strand wherein the antisense strand comprises at least one internal 2'-fluoro ribonucleotide modification, at least one internal 2'-deoxy ribonucleotide modification, and a sequence sufficiently complementary to a single target mRNA sequence to direct target-specific RNA interference (RNAi), wherein one or more purine nucleotides in one or both of the sense or antisense strands is chemically modified with a 2'-sugar modification and wherein in vivo stability is enhanced as compared to a corresponding unmodified siRNA or wherein target efficiency is enhanced compared to a corresponding unmodified siRNA.

2. The siRNA of claim 1 which is sufficiently complementary to a target mRNA, said target mRNA specifying the amino acid sequence of a cellular protein or the amino acid sequence of a viral protein.

3. The siRNA of claim 1, further comprising at least one additional modified nucleotide selected from the group consisting of
   (a) a sugar-modified nucleotide,
   (b) a nucleobase-modified nucleotide,
   (c) a 2'-deoxy ribonucleotide that is present within the sense strand,
   (d) a 2'-fluoro modified ribonucleotide that is present within the sense strand,
   (e) a modified nucleotide selected from the group consisting of a 2'-fluoro, 2'-amino and 2'-thio modified ribonucleotide,
   (f) modified nucleotides which are one or both of a 2'-fluoro modified ribonucleotide and a 2'-deoxy ribonucleotide that is present within the sense strand,
   (g) a modified nucleotide selected from the group consisting of 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine and 2'-amino-butyryl-pyrene-uridine,
   (h) a modified nucleotide selected from the group consisting of 5-bromo-uridine, 5-iodo-uridine, 5-methyl-cytidine, ribo-thymidine, 2-aminopurine, 5-fluoro-cytidine, and 5-fluoro-uridine, 2,6-diaminopurine, 4-thio-uridine; and 5-amino-allyl-uridine, and
   (i) a backbone-modified nucleotide.

4. The siRNA of claim 1, wherein the sense strand is crosslinked to the antisense strand, or wherein a 3' OH terminus of the sense strand or antisense strand is modified.

5. The siRNA of claim 1, comprising about 10 to 50 residues in length, between about 15 to 45 residues in length, between about 20 to 40 residues in length, or between about 18 to 25 residues in length.

6. A composition comprising the siRNA molecule of claim 1 and a pharmaceutically acceptable carrier.

7. A method of activating target-specific RNA interference (RNAi) in a cell or organism comprising introducing into said cell or organism the siRNA of claim 1, said siRNA being introduced in an amount sufficient for degradation of target mRNA to occur, thereby activating target-specific RNAi in the cell.

8. A cell or organism obtained by the method of claim 7.

9. A kit comprising reagents for activating target-specific RNA interference (RNAi) in a cell or organism, said kit comprising:
   (a) the siRNA molecule of claim 1; and
   (b) instructions for use.

10. The siRNA of claim 5, wherein the 2'-fluoro modified ribonucleotide comprises a 2'-fluoro uridine or a 2'-fluoro cytidine.

11. The siRNA of claim 3, wherein the 2'-deoxy ribonucleotide comprises at least one 2'-deoxy adenosine, at least one 2'-deoxy guanosine, or a mixture thereof.

12. The siRNA of claim 3, wherein the backbone-modified nucleotide comprises a phosphorothioate.

* * * * *